US010563188B2

(12) United States Patent
Stringer et al.

(10) Patent No.: US 10,563,188 B2
(45) Date of Patent: Feb. 18, 2020

(54) POLYPEPTIDES HAVING PROTEASE ACTIVITY

(71) Applicant: Novozymes A/S, Bagsvaerd (DK)

(72) Inventors: Mary Ann Stringer, Soeborg (DK); Tine Hoff, Holte (DK); Peter Rahbek Oestergaard, Virum (DK); Katrine Fruergaard Pontoppidan, Lynge (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 15/954,892

(22) Filed: Apr. 17, 2018

(65) Prior Publication Data

US 2018/0273927 A1 Sep. 27, 2018

Related U.S. Application Data

(62) Division of application No. 15/673,594, filed on Aug. 10, 2017, now Pat. No. 10,006,017, which is a division of application No. 14/423,546, filed as application No. PCT/EP2013/068361 on Sep. 5, 2013, now Pat. No. 9,771,570.

(60) Provisional application No. 61/697,032, filed on Sep. 5, 2012.

(30) Foreign Application Priority Data

Sep. 5, 2012 (EP) .................................... 12183079

(51) Int. Cl.

| | |
|---|---|
| ***C12N 9/48*** | (2006.01) |
| ***A23K 40/25*** | (2016.01) |
| ***A23K 40/20*** | (2016.01) |
| ***C12N 9/58*** | (2006.01) |
| ***A23K 40/10*** | (2016.01) |
| ***A23K 20/174*** | (2016.01) |
| ***A23K 20/189*** | (2016.01) |
| ***A23K 10/14*** | (2016.01) |
| ***A23K 20/20*** | (2016.01) |
| ***A23K 20/22*** | (2016.01) |
| ***A23K 20/24*** | (2016.01) |
| ***A23K 20/26*** | (2016.01) |
| ***A23K 50/00*** | (2016.01) |
| ***A23K 50/20*** | (2016.01) |
| ***A23K 50/10*** | (2016.01) |
| ***A23K 50/75*** | (2016.01) |
| ***A23K 50/30*** | (2016.01) |
| ***A23K 50/80*** | (2016.01) |
| ***A23K 50/60*** | (2016.01) |
| ***C12N 9/50*** | (2006.01) |
| ***C12P 21/06*** | (2006.01) |

(52) U.S. Cl.

CPC .............. *C12N 9/485* (2013.01); *A23K 10/14* (2016.05); *A23K 20/174* (2016.05); *A23K 20/189* (2016.05); *A23K 20/20* (2016.05); *A23K 20/22* (2016.05); *A23K 20/24* (2016.05); *A23K 20/26* (2016.05); *A23K 20/30* (2016.05); *A23K 40/10* (2016.05); *A23K 40/20* (2016.05); *A23K 40/25* (2016.05); *A23K 50/00* (2016.05); *A23K 50/10* (2016.05); *A23K 50/20* (2016.05); *A23K 50/30* (2016.05); *A23K 50/60* (2016.05); *A23K 50/75* (2016.05); *A23K 50/80* (2016.05); *C12N 9/50* (2013.01); *C12N 9/58* (2013.01); *C12P 21/06* (2013.01); *C12Y 304/14* (2013.01); *C12Y 304/21* (2013.01); *Y02A 40/818* (2018.01)

(58) Field of Classification Search

USPC ........................................................ 435/212

See application file for complete search history.

(56) References Cited

U.S. PATENT DOCUMENTS

| | | | |
|---|---|---|---|
| 5,840,509 | A | 11/1998 | Ni et al. |
| 6,329,185 | B1 | 12/2001 | Kofod |

FOREIGN PATENT DOCUMENTS

| | | | |
|---|---|---|---|
| CN | 101669584 | A | 3/2010 |
| CN | 101816378 | A | 9/2010 |
| GB | 1390542 | | 4/1975 |
| JP | 2010155788 | | 7/2010 |
| WO | 95/28850 | A1 | 11/1995 |
| WO | 01/58275 | A2 | 8/2001 |
| WO | 01/58276 | A2 | 8/2001 |
| WO | 02/068623 | A2 | 9/2002 |
| WO | 2004/034776 | A2 | 4/2004 |
| WO | 2004/072221 | A2 | 8/2004 |
| WO | 2004/072279 | A1 | 8/2004 |
| WO | 2004/077960 | A2 | 9/2004 |
| WO | 2004/111220 | A1 | 12/2004 |
| WO | 2004/111223 | A1 | 12/2004 |
| WO | 2005/035747 | A2 | 4/2005 |
| WO | 2005/123911 | A1 | 12/2005 |
| WO | 2010/008841 | A2 | 1/2010 |
| WO | 2012/048334 | A2 | 4/2012 |

OTHER PUBLICATIONS

Floudas et al., NCBI Accession No. XP_008037111 (2012).
Desantis et al., J. Am. Chem. Soc., vol. 120, pp. 8582-8566 (1988).
Fernandez et al., PNAS, vol. 109, No. 14, pp. 5458-5463 (2012).
Fernandez et al., UniProt Accession No. M2QQ01 (2013).
Fernandez et al., UniProt Accession No. M2QWH2 (2013).
Fernandez et al., UniProt Accession No. M2RD67 (2013).

(Continued)

*Primary Examiner* — Sheridan Swope
(74) *Attorney, Agent, or Firm* — Elias Lambiris

(57) ABSTRACT

The present invention relates to isolated polypeptides having protease activity and isolated nucleic acid sequences encoding the proteases. The invention also relates to nucleic acid constructs, vectors, and host cells, including plant and animal cells, comprising the nucleic acid sequences, as well as methods for producing and using the proteases, in particular the use of the proteases in animal feed.

5 Claims, 5 Drawing Sheets

Specification includes a Sequence Listing.

(56) References Cited

OTHER PUBLICATIONS

Floudas et al., Science, vol. 336, pp. 1715-1719 (2012).
Martinez et al., Proc. Natl. Acad. Sci. USA, vol. 106, pp. 1954-1959 (2009).
Martinez et al., UniProt Accession No. B8P431 (2009).
Martinez et al., UniProt Accession No. B8PMI5 (2009).
Wymelenberg et al., Fungal Genetics and Biology, vol. 43, pp. 343-356 (2006).
Wymelenberg et al., UniProt Accession No. Q281W2 (2006).
Floudas et al., GenBank Accession No. EIW61051.1 (2012).
Wymelenberg et al., GenBank Accession No. DQ242648.1 (2006).
Acamovic et al., World's Poultry Science Journal, vol. 57, pp. 225-242 (2001).

SEQUENCE LISTING

```
<160> NUMBER OF SEQ ID NOS: 25

<210> SEQ ID NO 1
<211> LENGTH: 1847
<212> TYPE: DNA
<213> ORGANISM: Meripilus giganteus
<220> FEATURE:
<221> NAME/KEY: CDS
<222> LOCATION: (11)..(1702)
<220> FEATURE:
<221> NAME/KEY: sig_peptide
<222> LOCATION: (11)..(61)
<220> FEATURE:
<221> NAME/KEY: mat_peptide
<222> LOCATION: (605)..(1702)

<400> SEQUENCE: 1

ctcgaacacg atg gtc gcc acc  agc ttg ctc gtt gcc  tcc cta ttc acg       49
           Met Val Ala Thr  Ser Leu Leu Val Ala  Ser Leu Phe Thr
                       -195                 -190

ctc  gcc ctc ggc acg ccg  acg ggt cgc aac ctc  aag ctg cac gag        94
Leu  Ala Leu Gly Thr Pro  Thr Gly Arg Asn Leu  Lys Leu His Glu
-185                -180                 -175
```

-continued

```
gcg  cgc gaa gac ctt cct  gcc ggt ttc tcg ctg  cgc ggc gcc gcc       139
Ala  Arg Glu Asp Leu Pro  Ala Gly Phe Ser Leu  Arg Gly Ala Ala
-170                -165                 -160

tcg  ccc gac acg acg ctg  aag ctc cgc atc gcg  ctc gtg cag aac       184
Ser  Pro Asp Thr Thr Leu  Lys Leu Arg Ile Ala  Leu Val Gln Asn
-155                -150                 -145

aac  ttc gcc gag ctc gaa  gac aag ctc tac gac  gtc agc aca ccg       229
Asn  Phe Ala Glu Leu Glu  Asp Lys Leu Tyr Asp  Val Ser Thr Pro
-140                -135                 -130

tcc  agc gcc aac tac ggc  aac cac ctc tcg aag  gaa gag gtt gag       274
Ser  Ser Ala Asn Tyr Gly  Asn His Leu Ser Lys  Glu Glu Val Glu
-125                -120                 -115

cag  tac att gct ccg gct  ccc gag agc gtg aaa  gcc gtg aat gcc       319
Gln  Tyr Ile Ala Pro Ala  Pro Glu Ser Val Lys  Ala Val Asn Ala
-110                -105                 -100

tgg ctc acc gag aac gga ctc gac gcg cac acc att tcg ccc gcc ggc       367
Trp Leu Thr Glu Asn Gly Leu Asp Ala His Thr Ile Ser Pro Ala Gly
-95                 -90                 -85                 -80

gac tgg ctc gca ttc gag gtc ccc gtc agc aag gcg aat gag ctc ttc       415
Asp Trp Leu Ala Phe Glu Val Pro Val Ser Lys Ala Asn Glu Leu Phe
                -75                 -70                 -65

gac gcc gac ttc tcc gtg ttt acc cac gat gag tcc ggc ctc gag gct       463
Asp Ala Asp Phe Ser Val Phe Thr His Asp Glu Ser Gly Leu Glu Ala
            -60                 -55                 -50

atc cgg acg ctg gcc tac tcc atc cct gct gag ctt cag gga cac ctc       511
Ile Arg Thr Leu Ala Tyr Ser Ile Pro Ala Glu Leu Gln Gly His Leu
        -45                 -40                 -35

gac ctt gtt cac ccc acc gtc acg ttc ccg aac ccc aat gcg cac ctg       559
Asp Leu Val His Pro Thr Val Thr Phe Pro Asn Pro Asn Ala His Leu
    -30                 -25                 -20

ccc gtc gtg cgc tcc acc cag ccc atc cgg aac ctg acc gga cgt gct       607
Pro Val Val Arg Ser Thr Gln Pro Ile Arg Asn Leu Thr Gly Arg Ala
-15                 -10                 -5                  -1  1

ata ccg gcc tct tgc gcg agc acc atc acc cct gcg tgc ttg cag gcc       655
Ile Pro Ala Ser Cys Ala Ser Thr Ile Thr Pro Ala Cys Leu Gln Ala
            5                   10                  15

atc tac ggt atc ccc acc acc aag gct act cag tcc tcg aac aag ctc       703
Ile Tyr Gly Ile Pro Thr Thr Lys Ala Thr Gln Ser Ser Asn Lys Leu
        20                  25                  30

gct gtc agc ggc ttc atc gac cag ttt gcg aac aag gct gac ctg aag       751
Ala Val Ser Gly Phe Ile Asp Gln Phe Ala Asn Lys Ala Asp Leu Lys
    35                  40                  45

tca ttc ctg gcc cag ttc cgc aaa gac atc tca tcc tcc acg act ttc       799
Ser Phe Leu Ala Gln Phe Arg Lys Asp Ile Ser Ser Ser Thr Thr Phe
50                  55                  60                  65

tcg ctt cag act ctc gat ggt gga gag aac gac cag agc cct agc gag       847
Ser Leu Gln Thr Leu Asp Gly Gly Glu Asn Asp Gln Ser Pro Ser Glu
                70                  75                  80

gcg ggt atc gag gct aac ttg gat atc cag tac acc gtc ggc ctc gcc       895
Ala Gly Ile Glu Ala Asn Leu Asp Ile Gln Tyr Thr Val Gly Leu Ala
            85                  90                  95

acg ggc gtc cct acc acg ttc atc tcc gtc ggc gac gac ttc cag gat       943
Thr Gly Val Pro Thr Thr Phe Ile Ser Val Gly Asp Asp Phe Gln Asp
        100                 105                 110

ggc aac ttg gag ggc ttc ctg gac atc atc aac ttc ttg ctc ggc gag       991
Gly Asn Leu Glu Gly Phe Leu Asp Ile Ile Asn Phe Leu Leu Gly Glu
    115                 120                 125

agc aac ccg ccg cag gtc ctc acc acc agt tac ggc cag aac gag aac      1039
Ser Asn Pro Pro Gln Val Leu Thr Thr Ser Tyr Gly Gln Asn Glu Asn
```

-continued

```
130                 135                 140                 145

acg atc tcg gcc aag ctt gct aac caa ctt tgc aat gcg tac gct cag     1087
Thr Ile Ser Ala Lys Leu Ala Asn Gln Leu Cys Asn Ala Tyr Ala Gln
                150                 155                 160

ctc ggc gcg cgc ggc acc tct atc ctc ttc gcg tcg ggt gat ggc ggt     1135
Leu Gly Ala Arg Gly Thr Ser Ile Leu Phe Ala Ser Gly Asp Gly Gly
            165                 170                 175

gtg tcc ggc tcg cag tcc gcg cac tgc agc aat ttt gtc ccg aca ttc     1183
Val Ser Gly Ser Gln Ser Ala His Cys Ser Asn Phe Val Pro Thr Phe
        180                 185                 190

ccc tcc ggc tgc ccc ttc atg act tcc gtc ggc gcg acg cag ggc gtc     1231
Pro Ser Gly Cys Pro Phe Met Thr Ser Val Gly Ala Thr Gln Gly Val
    195                 200                 205

agc ccc gag act gcc gcc gcc ttc tca tcc ggc ggc ttc tcg aac gtg     1279
Ser Pro Glu Thr Ala Ala Ala Phe Ser Ser Gly Gly Phe Ser Asn Val
210                 215                 220                 225

ttc ggc atc ccg tcg tac cag gct tcc gcg gtc agc ggc tac ctg tcc     1327
Phe Gly Ile Pro Ser Tyr Gln Ala Ser Ala Val Ser Gly Tyr Leu Ser
                230                 235                 240

gcg ctc gga agc acg aac tcg ggc aag ttc aac cgc agc gga cgc gga     1375
Ala Leu Gly Ser Thr Asn Ser Gly Lys Phe Asn Arg Ser Gly Arg Gly
            245                 250                 255

ttc ccc gac gtc tcc acg caa ggc gtg gac ttc cag atc gtc agc ggc     1423
Phe Pro Asp Val Ser Thr Gln Gly Val Asp Phe Gln Ile Val Ser Gly
        260                 265                 270

ggc cag acg atc ggc gtc gac ggc acg agc tgc gcc agc ccg acg ttc     1471
Gly Gln Thr Ile Gly Val Asp Gly Thr Ser Cys Ala Ser Pro Thr Phe
    275                 280                 285

gcg agc gtc atc tcg ctg gta aac gac cgc ctc atc gcg gcc ggc aag     1519
Ala Ser Val Ile Ser Leu Val Asn Asp Arg Leu Ile Ala Ala Gly Lys
290                 295                 300                 305

agc ccg ctc ggc ttc ctg aac ccc ttc ctg tac tcg tcg gcg ggc aag     1567
Ser Pro Leu Gly Phe Leu Asn Pro Phe Leu Tyr Ser Ser Ala Gly Lys
                310                 315                 320

gcc gcg ctc aac gac gtc acg agt ggc tcg aac cct ggc tgc agc acg     1615
Ala Ala Leu Asn Asp Val Thr Ser Gly Ser Asn Pro Gly Cys Ser Thr
            325                 330                 335

aac ggc ttc ccc gct aag gcc ggc tgg gac ccg gtc act ggt ctt ggc     1663
Asn Gly Phe Pro Ala Lys Ala Gly Trp Asp Pro Val Thr Gly Leu Gly
        340                 345                 350

acg ccc aac ttt gcc aag ctc ctc acc gcg gtc ggc ctg tgaatgtgga      1712
Thr Pro Asn Phe Ala Lys Leu Leu Thr Ala Val Gly Leu
    355                 360                 365

cgaaatacaa gaacgtggaa cgatgtgcac agtcagaagg aatgatcgcg cagtggcggt   1772

gtactattgt agatgtacgg gcaaagatgt acaccttttt agcagtcaaa atgtaaacgt   1832

gtttgcgtct ggctt                                                    1847


<210> SEQ ID NO 2
<211> LENGTH: 564
<212> TYPE: PRT
<213> ORGANISM: Meripilus giganteus

<400> SEQUENCE: 2

Met Val Ala Thr  Ser Leu Leu Val Ala  Ser Leu Phe Thr Leu  Ala
            -195                 -190                 -185

Leu Gly Thr Pro  Thr Gly Arg Asn Leu  Lys Leu His Glu Ala  Arg
            -180                 -175                 -170

Glu Asp Leu Pro  Ala Gly Phe Ser Leu  Arg Gly Ala Ala Ser  Pro
```

```
            -165                -160                -155

Asp Thr Thr Leu  Lys Leu Arg Ile Ala  Leu Val Gln Asn Asn  Phe
            -150                -145                -140

Ala Glu Leu Glu  Asp Lys Leu Tyr Asp  Val Ser Thr Pro Ser  Ser
            -135                -130                -125

Ala Asn Tyr Gly  Asn His Leu Ser Lys  Glu Glu Val Glu Gln  Tyr
            -120                -115                -110

Ile Ala Pro Ala  Pro Glu Ser Val Lys  Ala Val Asn Ala Trp Leu Thr
            -105                -100                -95

Glu Asn Gly Leu Asp Ala His Thr Ile Ser Pro Ala Gly Asp Trp Leu
        -90                 -85                 -80

Ala Phe Glu Val Pro Val Ser Lys Ala Asn Glu Leu Phe Asp Ala Asp
    -75                 -70                 -65

Phe Ser Val Phe Thr His Asp Glu Ser Gly Leu Glu Ala Ile Arg Thr
-60                 -55                 -50                 -45

Leu Ala Tyr Ser Ile Pro Ala Glu Leu Gln Gly His Leu Asp Leu Val
                -40                 -35                 -30

His Pro Thr Val Thr Phe Pro Asn Pro Asn Ala His Leu Pro Val Val
            -25                 -20                 -15

Arg Ser Thr Gln Pro Ile Arg Asn Leu Thr Gly Arg Ala Ile Pro Ala
        -10                 -5              -1  1

Ser Cys Ala Ser Thr Ile Thr Pro Ala Cys Leu Gln Ala Ile Tyr Gly
5                   10                  15                  20

Ile Pro Thr Thr Lys Ala Thr Gln Ser Ser Asn Lys Leu Ala Val Ser
                25                  30                  35

Gly Phe Ile Asp Gln Phe Ala Asn Lys Ala Asp Leu Lys Ser Phe Leu
            40                  45                  50

Ala Gln Phe Arg Lys Asp Ile Ser Ser Ser Thr Thr Phe Ser Leu Gln
        55                  60                  65

Thr Leu Asp Gly Gly Glu Asn Asp Gln Ser Pro Ser Glu Ala Gly Ile
    70                  75                  80

Glu Ala Asn Leu Asp Ile Gln Tyr Thr Val Gly Leu Ala Thr Gly Val
85                  90                  95                  100

Pro Thr Thr Phe Ile Ser Val Gly Asp Asp Phe Gln Asp Gly Asn Leu
                105                 110                 115

Glu Gly Phe Leu Asp Ile Ile Asn Phe Leu Leu Gly Glu Ser Asn Pro
            120                 125                 130

Pro Gln Val Leu Thr Thr Ser Tyr Gly Gln Asn Glu Asn Thr Ile Ser
        135                 140                 145

Ala Lys Leu Ala Asn Gln Leu Cys Asn Ala Tyr Ala Gln Leu Gly Ala
    150                 155                 160

Arg Gly Thr Ser Ile Leu Phe Ala Ser Gly Asp Gly Gly Val Ser Gly
165                 170                 175                 180

Ser Gln Ser Ala His Cys Ser Asn Phe Val Pro Thr Phe Pro Ser Gly
                185                 190                 195

Cys Pro Phe Met Thr Ser Val Gly Ala Thr Gln Gly Val Ser Pro Glu
            200                 205                 210

Thr Ala Ala Ala Phe Ser Ser Gly Gly Phe Ser Asn Val Phe Gly Ile
        215                 220                 225

Pro Ser Tyr Gln Ala Ser Ala Val Ser Gly Tyr Leu Ser Ala Leu Gly
    230                 235                 240

Ser Thr Asn Ser Gly Lys Phe Asn Arg Ser Gly Arg Gly Phe Pro Asp
245                 250                 255                 260
```

```
Val Ser Thr Gln Gly Val Asp Phe Gln Ile Val Ser Gly Gly Gln Thr
                265                 270                 275

Ile Gly Val Asp Gly Thr Ser Cys Ala Ser Pro Thr Phe Ala Ser Val
            280                 285                 290

Ile Ser Leu Val Asn Asp Arg Leu Ile Ala Ala Gly Lys Ser Pro Leu
        295                 300                 305

Gly Phe Leu Asn Pro Phe Leu Tyr Ser Ser Ala Gly Lys Ala Ala Leu
    310                 315                 320

Asn Asp Val Thr Ser Gly Ser Asn Pro Gly Cys Ser Thr Asn Gly Phe
325                 330                 335                 340

Pro Ala Lys Ala Gly Trp Asp Pro Val Thr Gly Leu Gly Thr Pro Asn
                345                 350                 355

Phe Ala Lys Leu Leu Thr Ala Val Gly Leu
            360                 365


<210> SEQ ID NO 3
<211> LENGTH: 1719
<212> TYPE: DNA
<213> ORGANISM: Artificial Sequence
<220> FEATURE:
<223> OTHER INFORMATION: Synthetic construct
<220> FEATURE:
<221> NAME/KEY: CDS
<222> LOCATION: (1)..(1716)
<220> FEATURE:
<221> NAME/KEY: mat_peptide
<222> LOCATION: (595)..(1692)
<220> FEATURE:
<221> NAME/KEY: misc_recomb
<222> LOCATION: (1693)..(1716)

<400> SEQUENCE: 3

atg gtc gcc acc  agc ttg ctc gtt gcc  tcc cta ttc acg ctc  gcc        45
Met Val Ala Thr  Ser Leu Leu Val Ala  Ser Leu Phe Thr Leu  Ala
            -195                 -190                 -185

ctc ggc acg ccg  acg ggt cgc aac ctc  aag ctg cac gag gcg  cgc        90
Leu Gly Thr Pro  Thr Gly Arg Asn Leu  Lys Leu His Glu Ala  Arg
            -180                 -175                 -170

gaa gac ctt cct  gcc ggt ttc tcg ctg  cgc ggc gcc gcc tcg  ccc       135
Glu Asp Leu Pro  Ala Gly Phe Ser Leu  Arg Gly Ala Ala Ser  Pro
            -165                 -160                 -155

gac acg acg ctg  aag ctc cgc atc gcg  ctc gtg cag aac aac  ttc       180
Asp Thr Thr Leu  Lys Leu Arg Ile Ala  Leu Val Gln Asn Asn  Phe
            -150                 -145                 -140

gcc gag ctc gaa  gac aag ctc tac gac  gtc agc aca ccg tcc  agc       225
Ala Glu Leu Glu  Asp Lys Leu Tyr Asp  Val Ser Thr Pro Ser  Ser
            -135                 -130                 -125

gcc aac tac ggc  aac cac ctc tcg aag  gaa gag gtt gag cag  tac       270
Ala Asn Tyr Gly  Asn His Leu Ser Lys  Glu Glu Val Glu Gln  Tyr
            -120                 -115                 -110

att gct ccg gct  ccc gag agc gtg aaa  gcc gtg aat gcc tgg ctc acc    318
Ile Ala Pro Ala  Pro Glu Ser Val Lys  Ala Val Asn Ala Trp Leu Thr
            -105                 -100                 -95

gag aac gga ctc gac gcg cac acc att tcg ccc gcc ggc gac tgg ctc      366
Glu Asn Gly Leu Asp Ala His Thr Ile Ser Pro Ala Gly Asp Trp Leu
        -90                 -85                 -80

gca ttc gag gtc ccc gtc agc aag gcg aat gag ctc ttc gac gcc gac      414
Ala Phe Glu Val Pro Val Ser Lys Ala Asn Glu Leu Phe Asp Ala Asp
    -75                 -70                 -65

ttc tcc gtg ttt acc cac gat gag tcc ggc ctc gag gct atc cgg acg      462
Phe Ser Val Phe Thr His Asp Glu Ser Gly Leu Glu Ala Ile Arg Thr
```

-continued

```
-60                 -55                 -50                 -45

ctg gcc tac tcc atc cct gct gag ctt cag gga cac ctc gac ctt gtt      510
Leu Ala Tyr Ser Ile Pro Ala Glu Leu Gln Gly His Leu Asp Leu Val
                -40                 -35                 -30

cac ccc acc gtc acg ttc ccg aac ccc aat gcg cac ctg ccc gtc gtg      558
His Pro Thr Val Thr Phe Pro Asn Pro Asn Ala His Leu Pro Val Val
            -25                 -20                 -15

cgc tcc acc cag ccc atc cgg aac ctg acc gga cgt gct ata ccg gcc      606
Arg Ser Thr Gln Pro Ile Arg Asn Leu Thr Gly Arg Ala Ile Pro Ala
        -10                 -5                  -1  1

tct tgc gcg agc acc atc acc cct gcg tgc ttg cag gcc atc tac ggt      654
Ser Cys Ala Ser Thr Ile Thr Pro Ala Cys Leu Gln Ala Ile Tyr Gly
5                   10                  15                  20

atc ccc acc acc aag gct act cag tcc tcg aac aag ctc gct gtc agc      702
Ile Pro Thr Thr Lys Ala Thr Gln Ser Ser Asn Lys Leu Ala Val Ser
                25                  30                  35

ggc ttc atc gac cag ttt gcg aac aag gct gac ctg aag tca ttc ctg      750
Gly Phe Ile Asp Gln Phe Ala Asn Lys Ala Asp Leu Lys Ser Phe Leu
            40                  45                  50

gcc cag ttc cgc aaa gac atc tca tcc tcc acg act ttc tcg ctt cag      798
Ala Gln Phe Arg Lys Asp Ile Ser Ser Ser Thr Thr Phe Ser Leu Gln
        55                  60                  65

act ctc gat ggt gga gag aac gac cag agc cct agc gag gcg ggt atc      846
Thr Leu Asp Gly Gly Glu Asn Asp Gln Ser Pro Ser Glu Ala Gly Ile
    70                  75                  80

gag gct aac ttg gat atc cag tac acc gtc ggc ctc gcc acg ggc gtc      894
Glu Ala Asn Leu Asp Ile Gln Tyr Thr Val Gly Leu Ala Thr Gly Val
85                  90                  95                  100

cct acc acg ttc atc tcc gtc ggc gac gac ttc cag gat ggc aac ttg      942
Pro Thr Thr Phe Ile Ser Val Gly Asp Asp Phe Gln Asp Gly Asn Leu
                105                 110                 115

gag ggc ttc ctg gac atc atc aac ttc ttg ctc ggc gag agc aac ccg      990
Glu Gly Phe Leu Asp Ile Ile Asn Phe Leu Leu Gly Glu Ser Asn Pro
            120                 125                 130

ccg cag gtc ctc acc acc agt tac ggc cag aac gag aac acg atc tcg     1038
Pro Gln Val Leu Thr Thr Ser Tyr Gly Gln Asn Glu Asn Thr Ile Ser
        135                 140                 145

gcc aag ctt gct aac caa ctt tgc aat gcg tac gct cag ctc ggc gcg     1086
Ala Lys Leu Ala Asn Gln Leu Cys Asn Ala Tyr Ala Gln Leu Gly Ala
    150                 155                 160

cgc ggc acc tct atc ctc ttc gcg tcg ggt gat ggc ggt gtg tcc ggc     1134
Arg Gly Thr Ser Ile Leu Phe Ala Ser Gly Asp Gly Gly Val Ser Gly
165                 170                 175                 180

tcg cag tcc gcg cac tgc agc aat ttt gtc ccg aca ttc ccc tcc ggc     1182
Ser Gln Ser Ala His Cys Ser Asn Phe Val Pro Thr Phe Pro Ser Gly
                185                 190                 195

tgc ccc ttc atg act tcc gtc ggc gcg acg cag ggc gtc agc ccc gag     1230
Cys Pro Phe Met Thr Ser Val Gly Ala Thr Gln Gly Val Ser Pro Glu
            200                 205                 210

act gcc gcc gcc ttc tca tcc ggc ggc ttc tcg aac gtg ttc ggc atc     1278
Thr Ala Ala Ala Phe Ser Ser Gly Gly Phe Ser Asn Val Phe Gly Ile
        215                 220                 225

ccg tcg tac cag gct tcc gcg gtc agc ggc tac ctg tcc gcg ctc gga     1326
Pro Ser Tyr Gln Ala Ser Ala Val Ser Gly Tyr Leu Ser Ala Leu Gly
    230                 235                 240

agc acg aac tcg ggc aag ttc aac cgc agc gga cgc gga ttc ccc gac     1374
Ser Thr Asn Ser Gly Lys Phe Asn Arg Ser Gly Arg Gly Phe Pro Asp
245                 250                 255                 260

gtc tcc acg caa ggc gtg gac ttc cag atc gtc agc ggc ggc cag acg     1422
```

-continued

```
Val Ser Thr Gln Gly Val Asp Phe Gln Ile Val Ser Gly Gly Gln Thr
            265                 270                 275

atc ggc gtc gac ggc acg agc tgc gcc agc ccg acg ttc gcg agc gtc     1470
Ile Gly Val Asp Gly Thr Ser Cys Ala Ser Pro Thr Phe Ala Ser Val
            280                 285                 290

atc tcg ctg gta aac gac cgc ctc atc gcg gcc ggc aag agc ccg ctc     1518
Ile Ser Leu Val Asn Asp Arg Leu Ile Ala Ala Gly Lys Ser Pro Leu
        295                 300                 305

ggc ttc ctg aac ccc ttc ctg tac tcg tcg gcg ggc aag gcc gcg ctc     1566
Gly Phe Leu Asn Pro Phe Leu Tyr Ser Ser Ala Gly Lys Ala Ala Leu
    310                 315                 320

aac gac gtc acg agt ggc tcg aac cct ggc tgc agc acg aac ggc ttc     1614
Asn Asp Val Thr Ser Gly Ser Asn Pro Gly Cys Ser Thr Asn Gly Phe
325                 330                 335                 340

ccc gct aag gcc ggc tgg gac ccg gtc act ggt ctt ggc acg ccc aac     1662
Pro Ala Lys Ala Gly Trp Asp Pro Val Thr Gly Leu Gly Thr Pro Asn
            345                 350                 355

ttt gcc aag ctc ctc acc gcg gtc ggc ctg cga cat cag cac cag cat     1710
Phe Ala Lys Leu Leu Thr Ala Val Gly Leu Arg His Gln His Gln His
            360                 365                 370

cag cac tga                                                         1719
Gln His


<210> SEQ ID NO 4
<211> LENGTH: 572
<212> TYPE: PRT
<213> ORGANISM: Artificial Sequence
<220> FEATURE:
<223> OTHER INFORMATION: Synthetic Construct

<400> SEQUENCE: 4

Met Val Ala Thr  Ser Leu Leu Val Ala  Ser Leu Phe Thr Leu  Ala
            -195                 -190                 -185

Leu Gly Thr Pro  Thr Gly Arg Asn Leu  Lys Leu His Glu Ala  Arg
            -180                 -175                 -170

Glu Asp Leu Pro  Ala Gly Phe Ser Leu  Arg Gly Ala Ala Ser  Pro
            -165                 -160                 -155

Asp Thr Thr Leu  Lys Leu Arg Ile Ala  Leu Val Gln Asn Asn  Phe
            -150                 -145                 -140

Ala Glu Leu Glu  Asp Lys Leu Tyr Asp  Val Ser Thr Pro Ser  Ser
            -135                 -130                 -125

Ala Asn Tyr Gly  Asn His Leu Ser Lys  Glu Glu Val Glu Gln  Tyr
            -120                 -115                 -110

Ile Ala Pro Ala  Pro Glu Ser Val Lys  Ala Val Asn Ala Trp Leu Thr
            -105                 -100                 -95

Glu Asn Gly Leu Asp Ala His Thr Ile Ser Pro Ala Gly Asp Trp Leu
        -90                 -85                 -80

Ala Phe Glu Val Pro Val Ser Lys Ala Asn Glu Leu Phe Asp Ala Asp
    -75                 -70                 -65

Phe Ser Val Phe Thr His Asp Glu Ser Gly Leu Glu Ala Ile Arg Thr
-60                 -55                 -50                 -45

Leu Ala Tyr Ser Ile Pro Ala Glu Leu Gln Gly His Leu Asp Leu Val
                -40                 -35                 -30

His Pro Thr Val Thr Phe Pro Asn Pro Asn Ala His Leu Pro Val Val
            -25                 -20                 -15

Arg Ser Thr Gln Pro Ile Arg Asn Leu Thr Gly Arg Ala Ile Pro Ala
        -10                 -5              -1  1
```

```
Ser Cys Ala Ser Thr Ile Thr Pro Ala Cys Leu Gln Ala Ile Tyr Gly
5                   10                  15                  20

Ile Pro Thr Thr Lys Ala Thr Gln Ser Ser Asn Lys Leu Ala Val Ser
                25                  30                  35

Gly Phe Ile Asp Gln Phe Ala Asn Lys Ala Asp Leu Lys Ser Phe Leu
            40                  45                  50

Ala Gln Phe Arg Lys Asp Ile Ser Ser Ser Thr Thr Phe Ser Leu Gln
        55                  60                  65

Thr Leu Asp Gly Gly Glu Asn Asp Gln Ser Pro Ser Glu Ala Gly Ile
    70                  75                  80

Glu Ala Asn Leu Asp Ile Gln Tyr Thr Val Gly Leu Ala Thr Gly Val
85                  90                  95                  100

Pro Thr Thr Phe Ile Ser Val Gly Asp Asp Phe Gln Asp Gly Asn Leu
                105                 110                 115

Glu Gly Phe Leu Asp Ile Ile Asn Phe Leu Leu Gly Glu Ser Asn Pro
            120                 125                 130

Pro Gln Val Leu Thr Thr Ser Tyr Gly Gln Asn Glu Asn Thr Ile Ser
        135                 140                 145

Ala Lys Leu Ala Asn Gln Leu Cys Asn Ala Tyr Ala Gln Leu Gly Ala
    150                 155                 160

Arg Gly Thr Ser Ile Leu Phe Ala Ser Gly Asp Gly Gly Val Ser Gly
165                 170                 175                 180

Ser Gln Ser Ala His Cys Ser Asn Phe Val Pro Thr Phe Pro Ser Gly
                185                 190                 195

Cys Pro Phe Met Thr Ser Val Gly Ala Thr Gln Gly Val Ser Pro Glu
            200                 205                 210

Thr Ala Ala Ala Phe Ser Ser Gly Gly Phe Ser Asn Val Phe Gly Ile
        215                 220                 225

Pro Ser Tyr Gln Ala Ser Ala Val Ser Gly Tyr Leu Ser Ala Leu Gly
    230                 235                 240

Ser Thr Asn Ser Gly Lys Phe Asn Arg Ser Gly Arg Gly Phe Pro Asp
245                 250                 255                 260

Val Ser Thr Gln Gly Val Asp Phe Gln Ile Val Ser Gly Gly Gln Thr
                265                 270                 275

Ile Gly Val Asp Gly Thr Ser Cys Ala Ser Pro Thr Phe Ala Ser Val
            280                 285                 290

Ile Ser Leu Val Asn Asp Arg Leu Ile Ala Ala Gly Lys Ser Pro Leu
        295                 300                 305

Gly Phe Leu Asn Pro Phe Leu Tyr Ser Ser Ala Gly Lys Ala Ala Leu
    310                 315                 320

Asn Asp Val Thr Ser Gly Ser Asn Pro Gly Cys Ser Thr Asn Gly Phe
325                 330                 335                 340

Pro Ala Lys Ala Gly Trp Asp Pro Val Thr Gly Leu Gly Thr Pro Asn
                345                 350                 355

Phe Ala Lys Leu Leu Thr Ala Val Gly Leu Arg His Gln His Gln His
            360                 365                 370

Gln His


<210> SEQ ID NO 5
<211> LENGTH: 366
<212> TYPE: PRT
<213> ORGANISM: Meripilus giganteus

<400> SEQUENCE: 5
```

-continued

```
Ala Ile Pro Ala Ser Cys Ala Ser Thr Ile Thr Pro Ala Cys Leu Gln
1               5                   10                  15

Ala Ile Tyr Gly Ile Pro Thr Thr Lys Ala Thr Gln Ser Ser Asn Lys
            20                  25                  30

Leu Ala Val Ser Gly Phe Ile Asp Gln Phe Ala Asn Lys Ala Asp Leu
        35                  40                  45

Lys Ser Phe Leu Ala Gln Phe Arg Lys Asp Ile Ser Ser Ser Thr Thr
    50                  55                  60

Phe Ser Leu Gln Thr Leu Asp Gly Gly Glu Asn Asp Gln Ser Pro Ser
65                  70                  75                  80

Glu Ala Gly Ile Glu Ala Asn Leu Asp Ile Gln Tyr Thr Val Gly Leu
                85                  90                  95

Ala Thr Gly Val Pro Thr Thr Phe Ile Ser Val Gly Asp Asp Phe Gln
            100                 105                 110

Asp Gly Asn Leu Glu Gly Phe Leu Asp Ile Ile Asn Phe Leu Leu Gly
        115                 120                 125

Glu Ser Asn Pro Pro Gln Val Leu Thr Thr Ser Tyr Gly Gln Asn Glu
    130                 135                 140

Asn Thr Ile Ser Ala Lys Leu Ala Asn Gln Leu Cys Asn Ala Tyr Ala
145                 150                 155                 160

Gln Leu Gly Ala Arg Gly Thr Ser Ile Leu Phe Ala Ser Gly Asp Gly
                165                 170                 175

Gly Val Ser Gly Ser Gln Ser Ala His Cys Ser Asn Phe Val Pro Thr
            180                 185                 190

Phe Pro Ser Gly Cys Pro Phe Met Thr Ser Val Gly Ala Thr Gln Gly
        195                 200                 205

Val Ser Pro Glu Thr Ala Ala Ala Phe Ser Ser Gly Gly Phe Ser Asn
    210                 215                 220

Val Phe Gly Ile Pro Ser Tyr Gln Ala Ser Ala Val Ser Gly Tyr Leu
225                 230                 235                 240

Ser Ala Leu Gly Ser Thr Asn Ser Gly Lys Phe Asn Arg Ser Gly Arg
                245                 250                 255

Gly Phe Pro Asp Val Ser Thr Gln Gly Val Asp Phe Gln Ile Val Ser
            260                 265                 270

Gly Gly Gln Thr Ile Gly Val Asp Gly Thr Ser Cys Ala Ser Pro Thr
        275                 280                 285

Phe Ala Ser Val Ile Ser Leu Val Asn Asp Arg Leu Ile Ala Ala Gly
    290                 295                 300

Lys Ser Pro Leu Gly Phe Leu Asn Pro Phe Leu Tyr Ser Ser Ala Gly
305                 310                 315                 320

Lys Ala Ala Leu Asn Asp Val Thr Ser Gly Ser Asn Pro Gly Cys Ser
                325                 330                 335

Thr Asn Gly Phe Pro Ala Lys Ala Gly Trp Asp Pro Val Thr Gly Leu
            340                 345                 350

Gly Thr Pro Asn Phe Ala Lys Leu Leu Thr Ala Val Gly Leu
        355                 360                 365
```

<210> SEQ ID NO 6
<211> LENGTH: 371
<212> TYPE: PRT
<213> ORGANISM: Artificial Sequence
<220> FEATURE:
<223> OTHER INFORMATION: mature polypeptide containing partial HQ-tag

<400> SEQUENCE: 6

-continued

```
Ala Ile Pro Ala Ser Cys Ala Ser Thr Ile Thr Pro Ala Cys Leu Gln
1               5                   10                  15

Ala Ile Tyr Gly Ile Pro Thr Thr Lys Ala Thr Gln Ser Ser Asn Lys
            20                  25                  30

Leu Ala Val Ser Gly Phe Ile Asp Gln Phe Ala Asn Lys Ala Asp Leu
        35                  40                  45

Lys Ser Phe Leu Ala Gln Phe Arg Lys Asp Ile Ser Ser Ser Thr Thr
    50                  55                  60

Phe Ser Leu Gln Thr Leu Asp Gly Gly Glu Asn Asp Gln Ser Pro Ser
65                  70                  75                  80

Glu Ala Gly Ile Glu Ala Asn Leu Asp Ile Gln Tyr Thr Val Gly Leu
                85                  90                  95

Ala Thr Gly Val Pro Thr Thr Phe Ile Ser Val Gly Asp Asp Phe Gln
            100                 105                 110

Asp Gly Asn Leu Glu Gly Phe Leu Asp Ile Ile Asn Phe Leu Leu Gly
        115                 120                 125

Glu Ser Asn Pro Pro Gln Val Leu Thr Thr Ser Tyr Gly Gln Asn Glu
    130                 135                 140

Asn Thr Ile Ser Ala Lys Leu Ala Asn Gln Leu Cys Asn Ala Tyr Ala
145                 150                 155                 160

Gln Leu Gly Ala Arg Gly Thr Ser Ile Leu Phe Ala Ser Gly Asp Gly
                165                 170                 175

Gly Val Ser Gly Ser Gln Ser Ala His Cys Ser Asn Phe Val Pro Thr
            180                 185                 190

Phe Pro Ser Gly Cys Pro Phe Met Thr Ser Val Gly Ala Thr Gln Gly
        195                 200                 205

Val Ser Pro Glu Thr Ala Ala Ala Phe Ser Ser Gly Gly Phe Ser Asn
    210                 215                 220

Val Phe Gly Ile Pro Ser Tyr Gln Ala Ser Ala Val Ser Gly Tyr Leu
225                 230                 235                 240

Ser Ala Leu Gly Ser Thr Asn Ser Gly Lys Phe Asn Arg Ser Gly Arg
                245                 250                 255

Gly Phe Pro Asp Val Ser Thr Gln Gly Val Asp Phe Gln Ile Val Ser
            260                 265                 270

Gly Gly Gln Thr Ile Gly Val Asp Gly Thr Ser Cys Ala Ser Pro Thr
        275                 280                 285

Phe Ala Ser Val Ile Ser Leu Val Asn Asp Arg Leu Ile Ala Ala Gly
    290                 295                 300

Lys Ser Pro Leu Gly Phe Leu Asn Pro Phe Leu Tyr Ser Ser Ala Gly
305                 310                 315                 320

Lys Ala Ala Leu Asn Asp Val Thr Ser Gly Ser Asn Pro Gly Cys Ser
                325                 330                 335

Thr Asn Gly Phe Pro Ala Lys Ala Gly Trp Asp Pro Val Thr Gly Leu
            340                 345                 350

Gly Thr Pro Asn Phe Ala Lys Leu Leu Thr Ala Val Gly Leu Arg His
        355                 360                 365

Gln His Gln
    370
```

<210> SEQ ID NO 7
<211> LENGTH: 1596
<212> TYPE: DNA
<213> ORGANISM: Nocardiopsis sp.
<220> FEATURE:
<221> NAME/KEY: CDS

```
<222> LOCATION: (318)..(1463)
<220> FEATURE:
<221> NAME/KEY: sig_peptide
<222> LOCATION: (318)..(404)
<220> FEATURE:
<221> NAME/KEY: mat_peptide
<222> LOCATION: (900)..(1463)

<400> SEQUENCE: 7

acgtttggta cgggtaccgg tgtccgcatg tggccagaat gccccttgc gacagggaac      60

ggattcggtc ggtagcgcat cgactccgac aaccgcgagg tggccgttcg cgtcgccacg    120

ttctgcgacc gtcatgcgac ccatcatcgg gtgaccccac cgagctctga atggtccacc    180

gttctgacgg tctttccctc accaaaacgt gcacctatgg ttaggacgtt gtttaccgaa    240

tgtctcggtg aacgacaggg gccggacggt attcggcccc gatcccccgt tgatcccccc    300

aggagagtag ggacccc atg cga ccc tcc ccc  gtt gtc tcc gcc atc  ggt     350
                   Met Arg Pro Ser Pro  Val Val Ser Ala Ile  Gly
                                   -190                 -185

acg gga gcg ctg  gcc ttc ggt ctg gcg  ctg tcc ggt acc ccg  ggt       395
Thr Gly Ala Leu  Ala Phe Gly Leu Ala  Leu Ser Gly Thr Pro  Gly
            -180                 -175                 -170

gcc ctc gcg gcc  acc gga gcg ctc ccc  cag tca ccc acc ccg  gag       440
Ala Leu Ala Ala  Thr Gly Ala Leu Pro  Gln Ser Pro Thr Pro  Glu
            -165                 -160                 -155

gcc gac gcg gtc  tcc atg cag gag gcg  ctc cag cgc gac ctc  gac       485
Ala Asp Ala Val  Ser Met Gln Glu Ala  Leu Gln Arg Asp Leu  Asp
            -150                 -145                 -140

ctg acc tcc gcc  gag gcc gag gag ctg  ctg gcc gcc cag gac  acc       530
Leu Thr Ser Ala  Glu Ala Glu Glu Leu  Leu Ala Ala Gln Asp  Thr
            -135                 -130                 -125

gcc ttc gag gtc  gac gag gcc gcg gcc  gag gcc gcc ggg gac  gcc       575
Ala Phe Glu Val  Asp Glu Ala Ala Ala  Glu Ala Ala Gly Asp  Ala
            -120                 -115                 -110

tac ggc ggc tcc  gtc ttc gac acc gag  agc ctg gaa ctg acc gtc ctg    623
Tyr Gly Gly Ser  Val Phe Asp Thr Glu  Ser Leu Glu Leu Thr Val Leu
            -105                 -100                 -95

gtc acc gat gcc gcc gcg gtc gag gcc gtg gag gcc acc ggc gcc ggg      671
Val Thr Asp Ala Ala Ala Val Glu Ala Val Glu Ala Thr Gly Ala Gly
        -90                 -85                 -80

acc gag ctg gtc tcc tac ggc atc gac ggt ctc gac gag atc gtc cag      719
Thr Glu Leu Val Ser Tyr Gly Ile Asp Gly Leu Asp Glu Ile Val Gln
    -75                 -70                 -65

gag ctc aac gcc gcc gac gcc gtt ccc ggt gtg gtc ggc tgg tac ccg      767
Glu Leu Asn Ala Ala Asp Ala Val Pro Gly Val Val Gly Trp Tyr Pro
-60                 -55                 -50                 -45

gac gtg gcg ggt gac acc gtc gtc ctg gag gtc ctg gag ggt tcc gga      815
Asp Val Ala Gly Asp Thr Val Val Leu Glu Val Leu Glu Gly Ser Gly
                -40                 -35                 -30

gcc gac gtc agc ggc ctg ctc gcg gac gcc ggc gtg gac gcc tcg gcc      863
Ala Asp Val Ser Gly Leu Leu Ala Asp Ala Gly Val Asp Ala Ser Ala
            -25                 -20                 -15

gtc gag gtg acc acg agc gac cag ccc gag ctc tac gcc gac atc atc      911
Val Glu Val Thr Thr Ser Asp Gln Pro Glu Leu Tyr Ala Asp Ile Ile
        -10                 -5              -1  1

ggt ggt ctg gcc tac acc atg ggc ggc cgc tgt tcg gtc ggc ttc gcg      959
Gly Gly Leu Ala Tyr Thr Met Gly Gly Arg Cys Ser Val Gly Phe Ala
5                   10                  15                  20

gcc acc aac gcc gcc ggt cag ccc ggg ttc gtc acc gcc ggt cac tgc     1007
Ala Thr Asn Ala Ala Gly Gln Pro Gly Phe Val Thr Ala Gly His Cys
                25                  30                  35
```

```
ggc cgc gtg ggc acc cag gtg acc atc ggc aac ggc agg ggc gtc ttc      1055
Gly Arg Val Gly Thr Gln Val Thr Ile Gly Asn Gly Arg Gly Val Phe
            40                  45                  50

gag cag tcc gtc ttc ccc ggc aac gac gcg gcc ttc gtc cgc ggt acg      1103
Glu Gln Ser Val Phe Pro Gly Asn Asp Ala Ala Phe Val Arg Gly Thr
        55                  60                  65

tcc aac ttc acg ctg acc aac ctg gtc agc cgc tac aac acc ggc ggg      1151
Ser Asn Phe Thr Leu Thr Asn Leu Val Ser Arg Tyr Asn Thr Gly Gly
    70                  75                  80

tac gcc acg gtc gcc ggt cac aac cag gcc ccc atc ggc tcc tcc gtc      1199
Tyr Ala Thr Val Ala Gly His Asn Gln Ala Pro Ile Gly Ser Ser Val
85                  90                  95                  100

tgc cgc tcc ggc tcc acc acc ggt tgg cac tgc ggc acc atc cag gcc      1247
Cys Arg Ser Gly Ser Thr Thr Gly Trp His Cys Gly Thr Ile Gln Ala
                105                 110                 115

cgc ggc cag tcg gtg agc tac ccc gag ggc acc gtc acc aac atg acc      1295
Arg Gly Gln Ser Val Ser Tyr Pro Glu Gly Thr Val Thr Asn Met Thr
            120                 125                 130

cgg acc acc gtg tgc gcc gag ccc ggc gac tcc ggc ggc tcc tac atc      1343
Arg Thr Thr Val Cys Ala Glu Pro Gly Asp Ser Gly Gly Ser Tyr Ile
        135                 140                 145

tcc ggc acc cag gcc cag ggc gtg acc tcc ggc ggc tcc ggc aac tgc      1391
Ser Gly Thr Gln Ala Gln Gly Val Thr Ser Gly Gly Ser Gly Asn Cys
    150                 155                 160

cgc acc ggc ggg acc acc ttc tac cag gag gtc acc ccc atg gtg aac      1439
Arg Thr Gly Gly Thr Thr Phe Tyr Gln Glu Val Thr Pro Met Val Asn
165                 170                 175                 180

tcc tgg ggc gtc cgt ctc cgg acc tgatccccgc ggttccaggc ggaccgacgg     1493
Ser Trp Gly Val Arg Leu Arg Thr
                185

tcgtgacctg agtaccaggc gtccccgccg cttccagcgg cgtccgcacc ggggtgggac   1553

cgggcgtggc cacggcccca cccgtgaccg gaccgcccgg cta                      1596


<210> SEQ ID NO 8
<211> LENGTH: 382
<212> TYPE: PRT
<213> ORGANISM: Nocardiopsis sp.

<400> SEQUENCE: 8

Met Arg Pro Ser Pro  Val Val Ser Ala Ile  Gly Thr Gly Ala Leu
                -190                 -185                 -180

Ala Phe Gly Leu Ala  Leu Ser Gly Thr Pro  Gly Ala Leu Ala Ala
                -175                 -170                 -165

Thr Gly Ala Leu Pro  Gln Ser Pro Thr Pro  Glu Ala Asp Ala Val
                -160                 -155                 -150

Ser Met Gln Glu Ala  Leu Gln Arg Asp Leu  Asp Leu Thr Ser Ala
                -145                 -140                 -135

Glu Ala Glu Glu Leu  Leu Ala Ala Gln Asp  Thr Ala Phe Glu Val
                -130                 -125                 -120

Asp Glu Ala Ala Ala  Glu Ala Ala Gly Asp  Ala Tyr Gly Gly Ser
                -115                 -110                 -105

Val Phe Asp Thr Glu  Ser Leu Glu Leu Thr Val Leu Val Thr Asp Ala
                -100                 -95                 -90

Ala Ala Val Glu Ala Val Glu Ala Thr Gly Ala Gly Thr Glu Leu Val
            -85                 -80                 -75

Ser Tyr Gly Ile Asp Gly Leu Asp Glu Ile Val Gln Glu Leu Asn Ala
        -70                 -65                 -60
```

```
Ala Asp Ala Val Pro Gly Val Val Gly Trp Tyr Pro Asp Val Ala Gly
    -55                 -50                 -45

Asp Thr Val Val Leu Glu Val Leu Glu Gly Ser Gly Ala Asp Val Ser
-40                 -35                 -30                 -25

Gly Leu Leu Ala Asp Ala Gly Val Asp Ala Ser Ala Val Glu Val Thr
                -20                 -15                 -10

Thr Ser Asp Gln Pro Glu Leu Tyr Ala Asp Ile Ile Gly Gly Leu Ala
            -5                  -1  1               5

Tyr Thr Met Gly Gly Arg Cys Ser Val Gly Phe Ala Ala Thr Asn Ala
    10                  15                  20

Ala Gly Gln Pro Gly Phe Val Thr Ala Gly His Cys Gly Arg Val Gly
25                  30                  35                  40

Thr Gln Val Thr Ile Gly Asn Gly Arg Gly Val Phe Glu Gln Ser Val
                45                  50                  55

Phe Pro Gly Asn Asp Ala Ala Phe Val Arg Gly Thr Ser Asn Phe Thr
            60                  65                  70

Leu Thr Asn Leu Val Ser Arg Tyr Asn Thr Gly Gly Tyr Ala Thr Val
        75                  80                  85

Ala Gly His Asn Gln Ala Pro Ile Gly Ser Ser Val Cys Arg Ser Gly
    90                  95                  100

Ser Thr Thr Gly Trp His Cys Gly Thr Ile Gln Ala Arg Gly Gln Ser
105                 110                 115                 120

Val Ser Tyr Pro Glu Gly Thr Val Thr Asn Met Thr Arg Thr Thr Val
                125                 130                 135

Cys Ala Glu Pro Gly Asp Ser Gly Gly Ser Tyr Ile Ser Gly Thr Gln
            140                 145                 150

Ala Gln Gly Val Thr Ser Gly Gly Ser Gly Asn Cys Arg Thr Gly Gly
        155                 160                 165

Thr Thr Phe Tyr Gln Glu Val Thr Pro Met Val Asn Ser Trp Gly Val
    170                 175                 180

Arg Leu Arg Thr
185


<210> SEQ ID NO 9
<211> LENGTH: 600
<212> TYPE: PRT
<213> ORGANISM: Grifola frondosa

<400> SEQUENCE: 9

Met Ser Leu Gly Arg Arg Ala Ser Ile Lys Gly Leu Leu Ser Ser Ala
1               5                   10                  15

Leu Ile Thr Pro Arg Val Pro Leu Ser Glu Gln Ser His Pro Ser Asn
            20                  25                  30

Met Ile Thr Ser Ser Phe Leu Val Val Ser Leu Phe Thr Leu Ala Leu
        35                  40                  45

Ser Lys Pro Met Ser Arg Ser Met Lys Val His Glu Thr Arg Glu Gly
    50                  55                  60

Ile Pro Asp Gly Phe Ala Leu Ala Gly Ser Pro Ser Ser Asp Thr Ser
65                  70                  75                  80

Leu Asn Leu Arg Ile Ala Leu Val Gln Asn Asp Pro Ala Gly Leu Glu
                85                  90                  95

Thr Ala Leu Tyr Asp Val Asn Thr Pro Ser Ser Ala Asn Tyr Gly Asn
            100                 105                 110

His Leu Ser Lys Ala Glu Val Glu Lys Phe Val Ala Pro Glu Pro Glu
```

-continued

```
        115                 120                 125

Ser Val Asp Ala Val Asn Ala Trp Leu Glu Glu Asn Gly Leu Thr Ala
    130                 135                 140

Thr Thr Ile Ser Pro Ala Gly Asp Trp Leu Ala Phe Glu Val Pro Val
145                 150                 155                 160

Ser Lys Ala Asn Glu Leu Phe Asp Ala Asp Phe Ser Val Tyr Thr His
                165                 170                 175

Thr Asp Thr Gly Leu Glu Ala Ile Arg Thr Leu Ser Tyr Ser Ile Pro
            180                 185                 190

Ala Glu Leu Gln Gly His Leu Asp Leu Val His Pro Thr Ile Thr Phe
        195                 200                 205

Pro Asn Pro Tyr Ser Arg Leu Pro Val Val Ala Ser Ser Ile Lys Thr
    210                 215                 220

Ala Ala Pro Thr Ser Asp Asn Leu Thr Ser Leu Ala Val Pro Ser Ser
225                 230                 235                 240

Cys Ala Ser Thr Ile Thr Pro Ala Cys Leu Gln Ala Leu Tyr Gly Ile
                245                 250                 255

Pro Thr Thr Pro Ala Thr Gln Ser Ser Asn Lys Leu Ala Val Ser Gly
            260                 265                 270

Tyr Ile Glu Gln Phe Ala Asn Gln Ala Asp Leu Lys Thr Phe Leu Thr
        275                 280                 285

Lys Phe Arg Thr Asp Ile Ser Ser Ser Thr Thr Phe Thr Thr Gln Thr
    290                 295                 300

Leu Asp Gly Gly Glu Asn Pro Gln Asn Gly Asn Glu Ala Gly Val Glu
305                 310                 315                 320

Ala Asp Leu Asp Val Gln Tyr Thr Val Gly Leu Ala Thr Asp Val Pro
                325                 330                 335

Thr Val Phe Ile Ser Val Gly Asp Asn Phe Gln Asp Gly Ala Leu Glu
            340                 345                 350

Gly Phe Leu Asp Ile Ile Asn Phe Leu Leu Asp Glu Ser Thr Pro Pro
        355                 360                 365

Gln Val Leu Thr Thr Ser Tyr Gly Gln Asn Glu Asn Thr Ile Ser Arg
    370                 375                 380

Asn Leu Ala Asn Asn Leu Cys Asn Ala Tyr Ala Gln Leu Gly Ala Arg
385                 390                 395                 400

Gly Thr Ser Ile Leu Phe Ala Ser Gly Asp Gly Gly Val Ser Gly Ser
                405                 410                 415

Gln Ser Asp Ser Cys Ser Lys Phe Val Pro Thr Phe Pro Ser Gly Cys
            420                 425                 430

Pro Phe Met Thr Ser Val Gly Ala Thr Thr Gly Ile Asn Pro Glu Thr
        435                 440                 445

Ala Ala Asp Phe Ser Ser Gly Gly Phe Ser Asn Tyr Phe Gly Thr Pro
    450                 455                 460

Ser Tyr Gln Ala Ser Ala His Ser Ala Tyr Leu Gln Ala Leu Gly Ser
465                 470                 475                 480

Thr Asn Ala Gly Lys Phe Asn Thr Ser Gly Arg Gly Phe Pro Asp Val
                485                 490                 495

Ser Thr Gln Gly Glu Asn Phe Gln Ile Val Val Asp Gly Gln Thr Gly
            500                 505                 510

Thr Val Asp Gly Thr Ser Cys Ala Ser Pro Thr Phe Ala Ser Val Val
        515                 520                 525

Ser Leu Leu Asn Asp Arg Leu Ile Ala Ala Gly Lys Ser Pro Leu Gly
    530                 535                 540
```

```
Phe Leu Asn Pro Phe Leu Tyr Ser Thr Gly Ala Ser Ala Phe Asn Ser
545                 550                 555                 560

Ile Thr Ser Gly Ser Asn Pro Gly Cys Asn Thr Asn Gly Phe Pro Ala
                565                 570                 575

Lys Thr Gly Trp Ser Pro Val Thr Gly Leu Gly Thr Pro Asn Phe Ala
            580                 585                 590

Lys Leu Leu Thr Ala Val Gly Leu
        595                 600


<210> SEQ ID NO 10
<211> LENGTH: 560
<212> TYPE: PRT
<213> ORGANISM: Postia placenta

<400> SEQUENCE: 10

Met Phe Ala His Ala Val Leu Val Ala Ala Leu Leu Pro Leu Thr Leu
1               5                   10                  15

Ala Ser Pro Leu Ala Thr Arg Asn Met His Val Leu Ala Arg Arg Ser
            20                  25                  30

Gly Pro Pro Ala Arg Phe Ser Met Ala Gly Ala Ala Ser Pro Asp Ala
        35                  40                  45

Thr Leu Asn Leu Arg Val Ala Leu Thr Gln Ser Asn Pro Ala Gly Leu
    50                  55                  60

Glu Asp Ala Leu Tyr Asp Val Ser Thr Pro Ser Ser Ala Asn Tyr Gly
65                  70                  75                  80

Asn His Leu Thr Lys Glu Glu Ala Ala Ala Phe Val Ala Pro Thr Lys
                85                  90                  95

Glu Ala Thr Ala Ala Val Thr Ser Trp Leu Asn Asn Asn Gly Val Asn
            100                 105                 110

Tyr Thr Thr Leu Thr Pro Ala Gly Asp Trp Leu Ser Leu Thr Val Pro
        115                 120                 125

Val Ser Gln Ala Asn Glu Leu Phe Gly Ala Gln Phe Asn Val Tyr Thr
    130                 135                 140

Asp Glu Thr Thr Gly Gln Gln Thr Val Arg Thr Met Ser Tyr Ala Val
145                 150                 155                 160

Pro Gln Thr Leu Ala Ala His Leu Thr Val Val Tyr Pro Thr Thr Thr
                165                 170                 175

Lys Gly Lys Thr Gly Gly Lys Ala Gly Gly Lys Ala Asn Ser Thr Ala
            180                 185                 190

Ser Ala Ser Gly Val Ala Ala Ser Cys Ala Asn Thr Ile Thr Pro Ala
        195                 200                 205

Cys Leu Gln Ser Leu Tyr Gly Ile Pro Thr Thr Pro Ala Thr Gln Ser
    210                 215                 220

Ser Asn Gln Leu Gly Val Ser Gly Phe Ile Asp Gln Phe Ala Asn Gln
225                 230                 235                 240

Ala Asp Leu Lys Thr Phe Leu Thr Thr Leu Arg Pro Asp Leu Ser Ser
                245                 250                 255

Ser Thr Thr Phe Ser Leu Gln Thr Leu Asp Gly Gly Glu Asn Ser Gln
            260                 265                 270

Thr Ala Gln Asp Ala Gly Thr Glu Ala Asn Leu Asp Thr Gln Tyr Thr
        275                 280                 285

Val Gly Leu Ala Thr Gly Val Pro Thr Thr Phe Ile Ser Val Gly Glu
    290                 295                 300

Lys Asn Gln Asp Gly Asp Leu Gly Gly Phe Leu Asp Ile Met Asn Phe
```

305 310 315 320

Leu Leu Asn Glu Asn Asp Pro Pro Ala Val Leu Thr Thr Ser Tyr Gly
325 330 335

Asp Asn Glu Asp Ala Ile Pro Val Gly Met Ala Asp Asn Leu Cys Asn
340 345 350

Ala Val Ala Gln Leu Gly Ala Arg Gly Val Ser Val Leu Phe Ala Ser
355 360 365

Gly Asp Gly Gly Val Ser Gly Ser Gln Ala Ala Gln Cys Thr Asp Phe
370 375 380

Val Pro Thr Phe Pro Ser Gly Cys Pro Tyr Leu Thr Ser Val Gly Ala
385 390 395 400

Thr Thr Gly Asn Ser Pro Glu Thr Ala Ala Ser Phe Ser Ala Gly Gly
405 410 415

Phe Ser Asn Tyr Phe Gly Thr Pro Ser Tyr Gln Ala Thr Ala Val Ser
420 425 430

Thr Tyr Leu Asn Thr Leu Gly Thr Thr Asn Lys Gly Leu Phe Asn Ala
435 440 445

Ser Gly Arg Gly Tyr Pro Asp Val Ser Thr Gln Gly Val Asn Phe Glu
450 455 460

Ile Val Val Asp Gly Ser Ala Gly Thr Val Asp Gly Thr Ser Cys Ala
465 470 475 480

Ser Pro Thr Phe Ala Ser Val Ile Ala Leu Leu Asn Asp Gln Leu Val
485 490 495

Ala Ala Gly Lys Ser Thr Leu Gly Phe Leu Asn Pro Trp Leu Tyr Ser
500 505 510

Thr Ala Ala Ser Ala Leu Thr Asp Ile Thr Ser Gly Asp Asn Pro Gly
515 520 525

Cys Asn Thr Asn Gly Phe Pro Ala Val Thr Gly Trp Asp Ala Val Thr
530 535 540

Gly Leu Gly Thr Pro Asn Phe Ala Lys Leu Gln Ala Ala Ala Gly Leu
545 550 555 560

<210> SEQ ID NO 11
<211> LENGTH: 565
<212> TYPE: PRT
<213> ORGANISM: Phanerochaete chrysosporium

<400> SEQUENCE: 11

Met Val Ser Lys Leu Leu Val Leu Ser Ala Leu Phe Ser Leu Ala Phe
1 5 10 15

Ala Lys Pro Thr Ala Arg Ser Met Lys Val Arg Glu Ala Arg Glu Ser
20 25 30

Val Pro Gly Gly Tyr Val Arg Thr Gly Pro Ala Pro Ala Asp Lys Glu
35 40 45

Leu Lys Leu Arg Ile Ala Leu Val Gln Asn Asn Pro Asp Gly Leu Ile
50 55 60

Asp Ala Leu Tyr Ala Val Ser Thr Pro Gly Ser Ala Ser Tyr Gly Glu
65 70 75 80

His Leu Ser Lys Glu Glu Val Glu Lys Phe Val Ala Pro Thr Ala Gln
85 90 95

Ser Ser Glu Ala Val Asn Ala Trp Leu Glu Gln Val Gly Leu Asn Ala
100 105 110

Thr Thr Val Ser Pro Ala Gly Asp Trp Leu Ser Val Thr Ile Pro Val
115 120 125

-continued

```
Ser Lys Ala Asn Glu Ile Phe Asp Ala Asp Phe Ala Val Tyr Thr His
    130                 135                 140

Phe Ala Thr Gly Lys Gln Ala Ile Arg Thr Met Ser Tyr Ser Ile Pro
145                 150                 155                 160

Ala Ser Leu Glu Gly His Leu Asp Phe Val His Pro Thr Ile Ser Phe
                165                 170                 175

Pro Ser Pro Asn Pro Ile Arg Pro Val Ile Ser Thr Pro Leu Gly Gly
            180                 185                 190

Leu Glu Gly Arg Ala Ile Glu Pro Leu Ala Ser Cys Ser Thr Ser Ala
        195                 200                 205

Val Thr Pro Ala Cys Ile Glu Ser Leu Tyr Gly Ile Pro Thr Thr Lys
    210                 215                 220

Ala Thr Gln Ser Ser Asn Thr Leu Gly Val Ser Gly Phe Ile Asp Gln
225                 230                 235                 240

Phe Ala Asn Gln Ala Asp Leu Thr Thr Phe Leu Asn Arg Phe Arg Pro
                245                 250                 255

Asp Leu Lys Gly Glu Thr Phe Thr Leu Gln Thr Leu Asp Gly Gly Gln
            260                 265                 270

Asn Pro Gln Ser Gly Ser Gln Ala Gly Val Glu Ala Asn Leu Asp Ile
        275                 280                 285

Gln Tyr Thr Val Gly Ile Ala Ser Gly Val Pro Val Thr Phe Ile Ser
    290                 295                 300

Val Gly Asp Asn Phe Gln Asp Gly Asp Leu Glu Gly Phe Leu Asp Ile
305                 310                 315                 320

Ile Asn Phe Leu Leu Asn Glu Ser Asn Pro Pro His Val Leu Thr Thr
                325                 330                 335

Ser Tyr Gly Asp Asn Glu Ser Asp Ile Ser Arg Ser Leu Ala Asn Asn
            340                 345                 350

Leu Cys Asn Ala Tyr Ala Gln Leu Gly Ala Arg Gly Thr Ser Ile Leu
        355                 360                 365

Phe Ala Ser Gly Asp Gly Gly Val Ser Gly Gly Gln Ser Gln Ser Cys
    370                 375                 380

Thr Lys Phe Val Pro Thr Phe Pro Ser Gly Cys Pro Phe Met Thr Ser
385                 390                 395                 400

Val Gly Ala Thr Gln Leu Thr Ser Ser Ser Gly Gly Glu Thr Ala Ala
                405                 410                 415

Ser Phe Ser Ser Gly Gly Phe Ser Asn Tyr Phe Ala Thr Pro Ser Tyr
            420                 425                 430

Gln Ala Ser Val Val Ser Ser Tyr Ile Ser Ser Ile Gly Ser Thr Asn
        435                 440                 445

Ser Gly Lys Tyr Asn Ala Ser Gly Arg Ala Phe Pro Asp Val Ala Ala
    450                 455                 460

Ile Gly Thr Asn Leu Glu Ile Val Val Asp Gly Ser Phe Gly Thr Val
465                 470                 475                 480

Asp Gly Thr Ser Cys Ser Ser Pro Val Phe Ala Ser Ala Ile Ala Leu
                485                 490                 495

Ile Asn Asp Ala Leu Val Ala Gln Gly Lys Ser Pro Leu Gly Phe Leu
            500                 505                 510

Asn Pro Phe Leu Tyr Ala Asn Pro Gly Ala Phe Asn Asp Ile Thr Ser
        515                 520                 525

Gly Ser Asn Pro Gly Cys Asn Thr Asn Gly Phe Lys Ala Ala Lys Gly
    530                 535                 540

Trp Asp Pro Val Thr Gly Leu Gly Thr Pro Asn Phe Ala Ala Leu Lys
```

```
545                 550                 555                 560

Ala Ala Ala Gly Val
                565


<210> SEQ ID NO 12
<211> LENGTH: 569
<212> TYPE: PRT
<213> ORGANISM: Postia placenta

<400> SEQUENCE: 12

Met Phe Leu Phe Pro Val Gly Leu Val Leu Ser Ala Leu Leu Thr Thr
1               5                   10                  15

Ala Ser Cys Thr Pro Ala Ser Thr Gly Leu His Val Leu Gly Arg Arg
            20                  25                  30

Asp Ser Pro Pro Ser Gly Phe Thr Phe Val Gly Ala Ala Ser Pro Asp
        35                  40                  45

Ser Val Leu Asn Leu Arg Ile Ala Leu Thr Gln Ser Asp Pro Ala Ala
    50                  55                  60

Leu Glu Glu Ala Leu Tyr Asp Val Ser Thr Pro Ser Ser Ser Asn Tyr
65                  70                  75                  80

Lys Gln Tyr Leu Ser Lys Glu Asp Val Ser Ala Phe Val Ala Pro Ser
                85                  90                  95

Pro Glu Ala Val Ser Ala Val Asn Ala Trp Leu Gln Glu Asn Asp Ile
            100                 105                 110

Thr Ala Lys Thr Leu Thr Pro Ala Gly Asp Trp Val Glu Val Gln Ile
        115                 120                 125

Pro Val Ser Lys Ala Asn Glu Ile Phe Asn Ala Asp Tyr Ser Val Phe
    130                 135                 140

Lys His Glu Ser Thr Gly Lys Gln Thr Ile Arg Thr Leu Ser Tyr Ser
145                 150                 155                 160

Ile Pro Glu Glu Leu Thr Asp His Val Ala Ile Val His Pro Thr Thr
                165                 170                 175

Thr Phe Val Phe Pro Thr Tyr Lys Ala Ser Leu Pro Ala Phe Arg Lys
            180                 185                 190

Val Ser Ser Arg Ala Ala Asn Thr Gly Val Ile Asp Thr Ala Ser Ser
        195                 200                 205

Cys Ala Asp Thr Ile Thr Pro Ala Cys Leu Gln Ser Leu Tyr Asn Leu
    210                 215                 220

Pro Ser Thr Pro Ala Thr Gln Thr Ser Asn Thr Leu Gly Val Ser Gly
225                 230                 235                 240

Phe Ser Asp Gln Tyr Ala Asn Gln Ala Asp Leu Ala Thr Phe Leu Glu
                245                 250                 255

Thr Tyr Arg Thr Asp Met Ser Ser Asp Thr Thr Phe Thr Val Glu Thr
            260                 265                 270

Leu Asp Gly Gly Ser Asp Pro Gln Asp Gly Ser Asp Ala Gly Asp Glu
        275                 280                 285

Ala Asn Leu Asp Thr Gln Tyr Thr Val Gly Leu Ala Thr Asp Val Pro
    290                 295                 300

Val Val Phe Ile Ser Val Gly Glu Asn Thr Asn Asp Gly Asp Leu Asp
305                 310                 315                 320

Gly Phe Leu Asp Ile Ile Asn Tyr Leu Leu Ala Gln Asp Ala Pro Pro
                325                 330                 335

Gln Val Leu Thr Thr Ser Tyr Gly Ser Ser Glu Ser Asp Val Pro Ile
            340                 345                 350
```

```
Ala Met Ala Glu Asn Leu Cys Asn Ala Tyr Ala Gln Leu Gly Ala Arg
        355                 360                 365

Gly Val Ser Ile Leu Phe Ala Ser Gly Asp Gly Gly Val Ser Gly Pro
    370                 375                 380

Gln Asp Ser Leu Phe Cys Trp Asp Phe Val Pro Thr Phe Pro Ser Gly
385                 390                 395                 400

Cys Pro Tyr Leu Thr Ser Val Gly Ala Thr Thr Gly Ile Ser Pro Glu
                405                 410                 415

Thr Ala Ala Asp Phe Ser Ser Gly Gly Phe Ser Asn Tyr Trp Gly Val
            420                 425                 430

Pro Ser Tyr Gln Gln Ser Ala Val Ser Gly Tyr Leu Ser Tyr Leu Gly
        435                 440                 445

Asp Thr Tyr Ser Gly Arg Tyr Asn Ala Ser Gly Arg Gly Tyr Pro Asp
    450                 455                 460

Val Ser Ala Gln Gly Glu Asn Phe Asn Ile Val Leu Asp Gln Asp Val
465                 470                 475                 480

Glu Ser Val Ser Gly Thr Ser Cys Ala Ser Pro Thr Phe Ala Ser Val
                485                 490                 495

Ile Ala Leu Leu Asn Asp Glu Leu Ile Ala Ala Gly Lys Ser Pro Leu
            500                 505                 510

Gly Phe Leu Asn Pro Trp Leu Tyr Ser Thr Ala Ala Ser Ser Leu Asn
        515                 520                 525

Asp Val Thr Ser Gly Asp Asn Pro Gly Cys Phe Ser Asp Gly Phe Ser
    530                 535                 540

Ala Thr Thr Gly Trp Asp Pro Val Thr Gly Leu Gly Thr Pro Asp Tyr
545                 550                 555                 560

Thr Ser Leu Arg Thr Ala Ala Gly Leu
                565


<210> SEQ ID NO 13
<211> LENGTH: 30
<212> TYPE: DNA
<213> ORGANISM: Artificial Sequence
<220> FEATURE:
<223> OTHER INFORMATION: Primer 597

<400> SEQUENCE: 13

tagggatcct cacgatggtc gccaccagct                                        30


<210> SEQ ID NO 14
<211> LENGTH: 18
<212> TYPE: DNA
<213> ORGANISM: Artificial Sequence
<220> FEATURE:
<223> OTHER INFORMATION: Primer 598

<400> SEQUENCE: 14

caggccgacc gcggtgag                                                     18


<210> SEQ ID NO 15
<211> LENGTH: 2087
<212> TYPE: DNA
<213> ORGANISM: Trametes cf versicolor
<220> FEATURE:
<221> NAME/KEY: CDS
<222> LOCATION: (1)..(258)
<220> FEATURE:
<221> NAME/KEY: sig_peptide
<222> LOCATION: (1)..(51)
<220> FEATURE:
<221> NAME/KEY: CDS
```

```
<222> LOCATION: (312)..(577)
<220> FEATURE:
<221> NAME/KEY: CDS
<222> LOCATION: (634)..(853)
<220> FEATURE:
<221> NAME/KEY: mat_peptide
<222> LOCATION: (707)..(2084)
<220> FEATURE:
<221> NAME/KEY: CDS
<222> LOCATION: (912)..(1022)
<220> FEATURE:
<221> NAME/KEY: CDS
<222> LOCATION: (1077)..(1276)
<220> FEATURE:
<221> NAME/KEY: CDS
<222> LOCATION: (1332)..(1469)
<220> FEATURE:
<221> NAME/KEY: CDS
<222> LOCATION: (1531)..(1978)
<220> FEATURE:
<221> NAME/KEY: CDS
<222> LOCATION: (2031)..(2084)

<400> SEQUENCE: 15

atg gtc gcc acc ggc  ttg ctc gtt gcc tcc  ctg ttc acg ctt gtc         45
Met Val Ala Thr Gly  Leu Leu Val Ala Ser  Leu Phe Thr Leu Val
                -195                 -190                 -185

ctc ggc act ccg acg  gct cgc aac ctc aag  ctg cat gag tct cgc         90
Leu Gly Thr Pro Thr  Ala Arg Asn Leu Lys  Leu His Glu Ser Arg
                -180                 -175                 -170

gag gag atc ccc gcc  ggc ttc tcg ctg agc  ggc gcc gcc tcg ccc        135
Glu Glu Ile Pro Ala  Gly Phe Ser Leu Ser  Gly Ala Ala Ser Pro
                -165                 -160                 -155

gac acg aca ctg aag  ctc cgc ctc gcg ctc  gtg cag agc aac ttc        180
Asp Thr Thr Leu Lys  Leu Arg Leu Ala Leu  Val Gln Ser Asn Phe
                -150                 -145                 -140

gcc gag ctc gag gac  aag ctc tac gac gtc  agc acc ccg tcg agc        225
Ala Glu Leu Glu Asp  Lys Leu Tyr Asp Val  Ser Thr Pro Ser Ser
                -135                 -130                 -125

gcg aac tac ggc cag  cac ctc tcc aag gag  gag gtacagctcg             268
Ala Asn Tyr Gly Gln  His Leu Ser Lys Glu  Glu
                -120                 -115

cctcccatgt ggctttgcgc agtttactca cgagcatttg cag gtt gag caa ctc      323
                                                Val Glu Gln Leu
                                                            -110

gtc gct cct agc gcc  gag tcg gtc aac gcc  gtc aac gcc tgg ctc act    371
Val Ala Pro Ser Ala  Glu Ser Val Asn Ala  Val Asn Ala Trp Leu Thr
                -105                 -100                 -95

gag aac ggt ctc act gcg cag acc atc tcg ccc gcc ggc gac tgg ttg      419
Glu Asn Gly Leu Thr Ala Gln Thr Ile Ser Pro Ala Gly Asp Trp Leu
            -90                 -85                 -80

gcg ttc gag gtg ccc gtc agc aag gcc aac gag ctc ttc gat gcc gac      467
Ala Phe Glu Val Pro Val Ser Lys Ala Asn Glu Leu Phe Asp Ala Asp
        -75                 -70                 -65

ttc tcc gtg ttc acg cac gac gag tct ggc ctc aag gct gtc cgc acc      515
Phe Ser Val Phe Thr His Asp Glu Ser Gly Leu Lys Ala Val Arg Thr
    -60                 -55                 -50

ctg gcg tac tcc atc ccc gct gag ctc cag ggg cac ctt gac ctc gtc      563
Leu Ala Tyr Ser Ile Pro Ala Glu Leu Gln Gly His Leu Asp Leu Val
-45                 -40                 -35                 -30

cac ccc acg atc ac  gtcagtcata ctgcttgcgc gcaattacca ccagtgctga      617
His Pro Thr Ile Thr
                -25

cgacttcttg tgacag g ttc ccg aac ccg aac tcg cac ctg ccc gtt gtg      667
                    Phe Pro Asn Pro Asn Ser His Leu Pro Val Val
```

-continued

```
                                    -20                 -15

cgc tcg ccc gtg aag ccc gtc cag aac ctc acc tcg cgt gcc gtt ccg      715
Arg Ser Pro Val Lys Pro Val Gln Asn Leu Thr Ser Arg Ala Val Pro
            -10                  -5              -1  1

gct tcg tgc gcc agc acc atc acg cct gcg tgc ctg cag gct ctc tac      763
Ala Ser Cys Ala Ser Thr Ile Thr Pro Ala Cys Leu Gln Ala Leu Tyr
    5                   10                  15

ggc atc ccc acc acc aag gcc act cag tca tcg aac aag ctc gcc gtc      811
Gly Ile Pro Thr Thr Lys Ala Thr Gln Ser Ser Asn Lys Leu Ala Val
20                  25                  30                  35

agc ggc ttc atc gac cag ttc gcc aac tcc gcg gac ttg aag              853
Ser Gly Phe Ile Asp Gln Phe Ala Asn Ser Ala Asp Leu Lys
                40                  45

gtgagcgtcc tagcgccccg gaaatcggat tcggtgctga tcattctgga ccttctag      911

aca ttc ctc ggc aag ttc cgc acc gac atc tcg tcc tcg acg acc ttc      959
Thr Phe Leu Gly Lys Phe Arg Thr Asp Ile Ser Ser Ser Thr Thr Phe
50                  55                  60                  65

acc ctc cag acc ctc gac ggc gga tcc aac agc cag tcc agc agc cag     1007
Thr Leu Gln Thr Leu Asp Gly Gly Ser Asn Ser Gln Ser Ser Ser Gln
                70                  75                  80

gct ggt gtt gag gct gtaagtggcg ggctatgctg ctgtacagag acaggcgctg     1062
Ala Gly Val Glu Ala
            85

acagcttgac atag aac ctg gac atc cag tac acc gtc ggc ctc gcc tcg     1112
                Asn Leu Asp Ile Gln Tyr Thr Val Gly Leu Ala Ser
                            90                  95

gcc gtc cct acc atc ttc atc tcc gtt ggc gac gac ttc cag gac ggc     1160
Ala Val Pro Thr Ile Phe Ile Ser Val Gly Asp Asp Phe Gln Asp Gly
    100                 105                 110

gac ctc gag ggc ttc ctc gac atc atc aac ttc ctc ctc aat gag agc     1208
Asp Leu Glu Gly Phe Leu Asp Ile Ile Asn Phe Leu Leu Asn Glu Ser
115                 120                 125                 130

gcg ccc ccg cag gtg ctc acg acc agc tac ggc cag aat gag aac acg     1256
Ala Pro Pro Gln Val Leu Thr Thr Ser Tyr Gly Gln Asn Glu Asn Thr
                135                 140                 145

atc tcc gcc aag ctt gcc aa  gtacgtccgc atgcgccacc cgcaatgcgc        1306
Ile Ser Ala Lys Leu Ala Asn
            150

tattcactga ccttcgtctg tgcag c caa ctg tgc aac gca tac gcc cag ctc   1359
                              Gln Leu Cys Asn Ala Tyr Ala Gln Leu
                                  155                 160

ggc gcg cgt ggc acc tcc atc ctc ttc gcc tcc ggt gac ggt ggt gtt     1407
Gly Ala Arg Gly Thr Ser Ile Leu Phe Ala Ser Gly Asp Gly Gly Val
        165                 170                 175

tcc ggc tcg cag tcc tct agc tgc tcc aag ttt gtc ccg acc ttc ccc     1455
Ser Gly Ser Gln Ser Ser Ser Cys Ser Lys Phe Val Pro Thr Phe Pro
    180                 185                 190

tcg ggc tgc ccc tt  gtacgtcact ccgcccaacc tcatccgctt gtagtactaa     1509
Ser Gly Cys Pro Phe
195

catggcgccc actcaccaca g c atg acc tcc gtc ggc gcg acg cag ggc atc   1561
                          Met Thr Ser Val Gly Ala Thr Gln Gly Ile
                          200                 205

aac ccg gag acc gcc gcc gac ttc tcc tcc ggc ggc ttc tcg aac gtc     1609
Asn Pro Glu Thr Ala Ala Asp Phe Ser Ser Gly Gly Phe Ser Asn Val
210                 215                 220                 225

ttc gcc cgc ccg tcg tac cag tcc acc gcc gtc agc agc tac ctc acc     1657
Phe Ala Arg Pro Ser Tyr Gln Ser Thr Ala Val Ser Ser Tyr Leu Thr
                230                 235                 240
```

```
gcg ctc ggc agc acc aac tcg ggc aag ttc aac acc tcc ggc cgc gca      1705
Ala Leu Gly Ser Thr Asn Ser Gly Lys Phe Asn Thr Ser Gly Arg Ala
            245                 250                 255

ttc ccc gac atc gcg acc cag ggc gtc gac ttt gag atc gtc gtc agc      1753
Phe Pro Asp Ile Ala Thr Gln Gly Val Asp Phe Glu Ile Val Val Ser
        260                 265                 270

ggc cgc acc gag ggt gtc gac ggc acg agc tgt gcc agc ccg acg ctc      1801
Gly Arg Thr Glu Gly Val Asp Gly Thr Ser Cys Ala Ser Pro Thr Leu
    275                 280                 285

gcc gcg atc atc tcg ctc ctg aac gac cgc ctc atc gcc gcc ggc aag      1849
Ala Ala Ile Ile Ser Leu Leu Asn Asp Arg Leu Ile Ala Ala Gly Lys
290                 295                 300                 305

agc ccc ctt ggc ttc ctc aac ccc ttc ttg tac tcg gcg gcg ggc act      1897
Ser Pro Leu Gly Phe Leu Asn Pro Phe Leu Tyr Ser Ala Ala Gly Thr
                310                 315                 320

gct gcg ctc act gac atc acg tcg ggc tcg aac ccg ggc tgc aac acc      1945
Ala Ala Leu Thr Asp Ile Thr Ser Gly Ser Asn Pro Gly Cys Asn Thr
            325                 330                 335

aac ggc ttc ccc gcg aag gct ggc tgg gac ccg gtgcgttcct ttctccgtgg   1998
Asn Gly Phe Pro Ala Lys Ala Gly Trp Asp Pro
        340                 345

cgcgcgcgaa acttgtactg acggcgttgc ag gtc acc ggt ctt ggc acg ccc      2051
                                    Val Thr Gly Leu Gly Thr Pro
                                        350                 355

aac ttc gcc aag ctg ctc acc gct gtt ggc ctg taa                      2087
Asn Phe Ala Lys Leu Leu Thr Ala Val Gly Leu
                360                 365


<210> SEQ ID NO 16
<211> LENGTH: 565
<212> TYPE: PRT
<213> ORGANISM: Trametes cf versicolor

<400> SEQUENCE: 16

Met Val Ala Thr Gly  Leu Leu Val Ala Ser  Leu Phe Thr Leu Val
                -195                 -190                 -185

Leu Gly Thr Pro Thr  Ala Arg Asn Leu Lys  Leu His Glu Ser Arg
                -180                 -175                 -170

Glu Glu Ile Pro Ala  Gly Phe Ser Leu Ser  Gly Ala Ala Ser Pro
                -165                 -160                 -155

Asp Thr Thr Leu Lys  Leu Arg Leu Ala Leu  Val Gln Ser Asn Phe
                -150                 -145                 -140

Ala Glu Leu Glu Asp  Lys Leu Tyr Asp Val  Ser Thr Pro Ser Ser
                -135                 -130                 -125

Ala Asn Tyr Gly Gln  His Leu Ser Lys Glu  Glu Val Glu Gln Leu
                -120                 -115                 -110

Val Ala Pro Ser Ala  Glu Ser Val Asn Ala  Val Asn Ala Trp Leu Thr
                -105                 -100                 -95

Glu Asn Gly Leu Thr Ala Gln Thr Ile Ser Pro Ala Gly Asp Trp Leu
            -90                 -85                 -80

Ala Phe Glu Val Pro Val Ser Lys Ala Asn Glu Leu Phe Asp Ala Asp
        -75                 -70                 -65

Phe Ser Val Phe Thr His Asp Glu Ser Gly Leu Lys Ala Val Arg Thr
    -60                 -55                 -50

Leu Ala Tyr Ser Ile Pro Ala Glu Leu Gln Gly His Leu Asp Leu Val
-45                 -40                 -35                 -30

His Pro Thr Ile Thr Phe Pro Asn Pro Asn Ser His Leu Pro Val Val
```

-continued

```
                -25                 -20                 -15

Arg Ser Pro Val Lys Pro Val Gln Asn Leu Thr Ser Arg Ala Val Pro
            -10                 -5              -1  1

Ala Ser Cys Ala Ser Thr Ile Thr Pro Ala Cys Leu Gln Ala Leu Tyr
    5                   10                  15

Gly Ile Pro Thr Thr Lys Ala Thr Gln Ser Ser Asn Lys Leu Ala Val
20                  25                  30                  35

Ser Gly Phe Ile Asp Gln Phe Ala Asn Ser Ala Asp Leu Lys Thr Phe
                40                  45                  50

Leu Gly Lys Phe Arg Thr Asp Ile Ser Ser Ser Thr Thr Phe Thr Leu
            55                  60                  65

Gln Thr Leu Asp Gly Gly Ser Asn Ser Gln Ser Ser Ser Gln Ala Gly
        70                  75                  80

Val Glu Ala Asn Leu Asp Ile Gln Tyr Thr Val Gly Leu Ala Ser Ala
    85                  90                  95

Val Pro Thr Ile Phe Ile Ser Val Gly Asp Asp Phe Gln Asp Gly Asp
100                 105                 110                 115

Leu Glu Gly Phe Leu Asp Ile Ile Asn Phe Leu Leu Asn Glu Ser Ala
                120                 125                 130

Pro Pro Gln Val Leu Thr Thr Ser Tyr Gly Gln Asn Glu Asn Thr Ile
            135                 140                 145

Ser Ala Lys Leu Ala Asn Gln Leu Cys Asn Ala Tyr Ala Gln Leu Gly
        150                 155                 160

Ala Arg Gly Thr Ser Ile Leu Phe Ala Ser Gly Asp Gly Gly Val Ser
    165                 170                 175

Gly Ser Gln Ser Ser Ser Cys Ser Lys Phe Val Pro Thr Phe Pro Ser
180                 185                 190                 195

Gly Cys Pro Phe Met Thr Ser Val Gly Ala Thr Gln Gly Ile Asn Pro
                200                 205                 210

Glu Thr Ala Ala Asp Phe Ser Ser Gly Gly Phe Ser Asn Val Phe Ala
            215                 220                 225

Arg Pro Ser Tyr Gln Ser Thr Ala Val Ser Ser Tyr Leu Thr Ala Leu
        230                 235                 240

Gly Ser Thr Asn Ser Gly Lys Phe Asn Thr Ser Gly Arg Ala Phe Pro
    245                 250                 255

Asp Ile Ala Thr Gln Gly Val Asp Phe Glu Ile Val Val Ser Gly Arg
260                 265                 270                 275

Thr Glu Gly Val Asp Gly Thr Ser Cys Ala Ser Pro Thr Leu Ala Ala
                280                 285                 290

Ile Ile Ser Leu Leu Asn Asp Arg Leu Ile Ala Ala Gly Lys Ser Pro
            295                 300                 305

Leu Gly Phe Leu Asn Pro Phe Leu Tyr Ser Ala Ala Gly Thr Ala Ala
        310                 315                 320

Leu Thr Asp Ile Thr Ser Gly Ser Asn Pro Gly Cys Asn Thr Asn Gly
    325                 330                 335

Phe Pro Ala Lys Ala Gly Trp Asp Pro Val Thr Gly Leu Gly Thr Pro
340                 345                 350                 355

Asn Phe Ala Lys Leu Leu Thr Ala Val Gly Leu
                360                 365
```

<210> SEQ ID NO 17
<211> LENGTH: 1698
<212> TYPE: DNA
<213> ORGANISM: Artificial Sequence

```
<220> FEATURE:
<223> OTHER INFORMATION: Synthetic construct
<220> FEATURE:
<221> NAME/KEY: CDS
<222> LOCATION: (1)..(1695)
<220> FEATURE:
<221> NAME/KEY: sig_peptide
<222> LOCATION: (1)..(51)
<220> FEATURE:
<221> NAME/KEY: mat_peptide
<222> LOCATION: (598)..(1695)

<400> SEQUENCE: 17

atg gtg gca act ggc  ttg ttg gtc gca tcc  ttg ttc act ttg gtg        45
Met Val Ala Thr Gly  Leu Leu Val Ala Ser  Leu Phe Thr Leu Val
                -195                 -190                 -185

ctc ggc act ccc acc  gca cgg aac ctc aag  ttg cac gag tcc agg        90
Leu Gly Thr Pro Thr  Ala Arg Asn Leu Lys  Leu His Glu Ser Arg
                -180                 -175                 -170

gaa gag atc cct gca  gga ttc tcg ttg tcc  gga gca gcg tcg cct       135
Glu Glu Ile Pro Ala  Gly Phe Ser Leu Ser  Gly Ala Ala Ser Pro
                -165                 -160                 -155

gat aca acc ttg aag  ttg cgg ttg gcg ttg  gtg cag tcc aac ttc       180
Asp Thr Thr Leu Lys  Leu Arg Leu Ala Leu  Val Gln Ser Asn Phe
                -150                 -145                 -140

gcg gag ctc gaa gac  aag ctc tat gat gtc  tcc acc ccg tcc tcg       225
Ala Glu Leu Glu Asp  Lys Leu Tyr Asp Val  Ser Thr Pro Ser Ser
                -135                 -130                 -125

gca aac tat gga cag  cac ctc tcc aaa gag  gag gtc gag cag ttg       270
Ala Asn Tyr Gly Gln  His Leu Ser Lys Glu  Glu Val Glu Gln Leu
                -120                 -115                 -110

gtg gca ccg tcg gca  gag tcg gtg aac gcg  gtc aac gcc tgg ttg acc   318
Val Ala Pro Ser Ala  Glu Ser Val Asn Ala  Val Asn Ala Trp Leu Thr
                -105                 -100                 -95

gaa aac gga ttg aca gca cag acc att tcg cct gca ggc gat tgg ttg     366
Glu Asn Gly Leu Thr Ala Gln Thr Ile Ser Pro Ala Gly Asp Trp Leu
            -90                 -85                 -80

gcg ttc gag gtc cct gtc tcg aag gcc aac gaa ctc ttc gac gca gac     414
Ala Phe Glu Val Pro Val Ser Lys Ala Asn Glu Leu Phe Asp Ala Asp
        -75                 -70                 -65

ttc tcg gtc ttc acc cac gac gag tcc gga ctc aag gcg gtc cga act     462
Phe Ser Val Phe Thr His Asp Glu Ser Gly Leu Lys Ala Val Arg Thr
    -60                 -55                 -50

ctc gcg tat tcg att cct gcg gag ttg cag ggt cat ctc gat ttg gtc     510
Leu Ala Tyr Ser Ile Pro Ala Glu Leu Gln Gly His Leu Asp Leu Val
-45                 -40                 -35                 -30

cac ccc acc atc acg ttc ccc aac ccc aac tcc cat ttg cct gtc gtg     558
His Pro Thr Ile Thr Phe Pro Asn Pro Asn Ser His Leu Pro Val Val
                -25                 -20                 -15

cgg tcc cct gtc aaa ccg gtc cag aac ctc aca tcc cgt gcc gtc cct     606
Arg Ser Pro Val Lys Pro Val Gln Asn Leu Thr Ser Arg Ala Val Pro
            -10                 -5              -1  1

gcc tcc tgt gcg tcg acg atc acc cct gca tgt ttg cag gca ctc tac     654
Ala Ser Cys Ala Ser Thr Ile Thr Pro Ala Cys Leu Gln Ala Leu Tyr
    5                   10                  15

ggt atc ccc act acc aag gca acc cag tcg tcg aac aag ttg gcc gtc     702
Gly Ile Pro Thr Thr Lys Ala Thr Gln Ser Ser Asn Lys Leu Ala Val
20                  25                  30                  35

tcc ggt ttc atc gat cag ttc gcg aac tcc gca gat ttg aaa aca ttc     750
Ser Gly Phe Ile Asp Gln Phe Ala Asn Ser Ala Asp Leu Lys Thr Phe
                40                  45                  50

ttg gga aag ttc cgg acc gat atc tcg tcg tcg acg acc ttc acc ctc     798
```

```
Leu Gly Lys Phe Arg Thr Asp Ile Ser Ser Ser Thr Thr Phe Thr Leu
            55                  60                  65

cag aca ctc gat gga ggc tcc aac tcg cag tcg tcc tcg cag gca ggt      846
Gln Thr Leu Asp Gly Gly Ser Asn Ser Gln Ser Ser Ser Gln Ala Gly
        70                  75                  80

gtg gag gcg aac ttg gac att cag tat aca gtc ggc ctc gca tcg gca      894
Val Glu Ala Asn Leu Asp Ile Gln Tyr Thr Val Gly Leu Ala Ser Ala
    85                  90                  95

gtg ccc act atc ttc atc tcc gtg ggt gac gat ttc cag gac gga gac      942
Val Pro Thr Ile Phe Ile Ser Val Gly Asp Asp Phe Gln Asp Gly Asp
100                 105                 110                 115

ctc gaa ggt ttc ctc gac att atc aac ttc ctc ctc aac gaa tcc gca      990
Leu Glu Gly Phe Leu Asp Ile Ile Asn Phe Leu Leu Asn Glu Ser Ala
                120                 125                 130

ccc cct cag gtc ttg acg act tcc tat ggc cag aac gag aac aca atc     1038
Pro Pro Gln Val Leu Thr Thr Ser Tyr Gly Gln Asn Glu Asn Thr Ile
            135                 140                 145

tcc gcg aag ctc gcc aac cag ctc tgt aac gca tac gcc cag ctc gga     1086
Ser Ala Lys Leu Ala Asn Gln Leu Cys Asn Ala Tyr Ala Gln Leu Gly
        150                 155                 160

gca cgt gga acg tcc atc ttg ttc gca tcc gga gat gga ggc gtg tcg     1134
Ala Arg Gly Thr Ser Ile Leu Phe Ala Ser Gly Asp Gly Gly Val Ser
    165                 170                 175

ggc tcg cag tcc tcg tcg tgt tcc aaa ttc gtc ccc aca ttc cct tcg     1182
Gly Ser Gln Ser Ser Ser Cys Ser Lys Phe Val Pro Thr Phe Pro Ser
180                 185                 190                 195

ggt tgt ccg ttc atg acc tcg gtc gga gcc aca cag ggc att aac ccg     1230
Gly Cys Pro Phe Met Thr Ser Val Gly Ala Thr Gln Gly Ile Asn Pro
                200                 205                 210

gag acc gca gcc gat ttc tcg tcc gga gga ttc tcc aac gtg ttc gca     1278
Glu Thr Ala Ala Asp Phe Ser Ser Gly Gly Phe Ser Asn Val Phe Ala
            215                 220                 225

cgg cct tcg tac cag tcc act gca gtc tcg tcg tac ctc act gcc ctc     1326
Arg Pro Ser Tyr Gln Ser Thr Ala Val Ser Ser Tyr Leu Thr Ala Leu
        230                 235                 240

ggc tcc acc aac tcg ggc aaa ttc aac acc tcg ggc agg gcc ttc ccg     1374
Gly Ser Thr Asn Ser Gly Lys Phe Asn Thr Ser Gly Arg Ala Phe Pro
    245                 250                 255

gat atc gcg acg cag ggc gtc gat ttc gag atc gtc gtc tcc ggt agg     1422
Asp Ile Ala Thr Gln Gly Val Asp Phe Glu Ile Val Val Ser Gly Arg
260                 265                 270                 275

act gag ggc gtc gac gga acg tcg tgt gcc tcc ccc acg ctc gca gca     1470
Thr Glu Gly Val Asp Gly Thr Ser Cys Ala Ser Pro Thr Leu Ala Ala
                280                 285                 290

atc atc tcg ctc ctc aac gac agg ctc att gca gca ggc aaa tcc cct     1518
Ile Ile Ser Leu Leu Asn Asp Arg Leu Ile Ala Ala Gly Lys Ser Pro
            295                 300                 305

ttg ggc ttc ctc aac ccc ttc ttg tac tcg gca gcg gga aca gcc gca     1566
Leu Gly Phe Leu Asn Pro Phe Leu Tyr Ser Ala Ala Gly Thr Ala Ala
        310                 315                 320

ttg acc gac atc acg tcc ggc tcg aac cct gga tgt aac acg aac gga     1614
Leu Thr Asp Ile Thr Ser Gly Ser Asn Pro Gly Cys Asn Thr Asn Gly
    325                 330                 335

ttc cct gca aag gca ggt tgg gac ccc gtc aca ggc ctc ggc act ccc     1662
Phe Pro Ala Lys Ala Gly Trp Asp Pro Val Thr Gly Leu Gly Thr Pro
340                 345                 350                 355

aac ttc gcc aag ctc ctc aca gcg gtc ggc ttg taa                     1698
Asn Phe Ala Lys Leu Leu Thr Ala Val Gly Leu
                360                 365
```

```
<210> SEQ ID NO 18
<211> LENGTH: 565
<212> TYPE: PRT
<213> ORGANISM: Artificial Sequence
<220> FEATURE:
<223> OTHER INFORMATION: Synthetic Construct

<400> SEQUENCE: 18

Met Val Ala Thr Gly  Leu Leu Val Ala Ser  Leu Phe Thr Leu Val
                -195                -190                -185

Leu Gly Thr Pro Thr  Ala Arg Asn Leu Lys  Leu His Glu Ser Arg
                -180                -175                -170

Glu Glu Ile Pro Ala  Gly Phe Ser Leu Ser  Gly Ala Ala Ser Pro
                -165                -160                -155

Asp Thr Thr Leu Lys  Leu Arg Leu Ala Leu  Val Gln Ser Asn Phe
                -150                -145                -140

Ala Glu Leu Glu Asp  Lys Leu Tyr Asp Val  Ser Thr Pro Ser Ser
                -135                -130                -125

Ala Asn Tyr Gly Gln  His Leu Ser Lys Glu  Glu Val Glu Gln Leu
                -120                -115                -110

Val Ala Pro Ser Ala  Glu Ser Val Asn Ala  Val Asn Ala Trp Leu Thr
                -105                -100                -95

Glu Asn Gly Leu Thr Ala Gln Thr Ile Ser Pro Ala Gly Asp Trp Leu
            -90                 -85                 -80

Ala Phe Glu Val Pro Val Ser Lys Ala Asn Glu Leu Phe Asp Ala Asp
        -75                 -70                 -65

Phe Ser Val Phe Thr His Asp Glu Ser Gly Leu Lys Ala Val Arg Thr
    -60                 -55                 -50

Leu Ala Tyr Ser Ile Pro Ala Glu Leu Gln Gly His Leu Asp Leu Val
-45                 -40                 -35                 -30

His Pro Thr Ile Thr Phe Pro Asn Pro Asn Ser His Leu Pro Val Val
                -25                 -20                 -15

Arg Ser Pro Val Lys Pro Val Gln Asn Leu Thr Ser Arg Ala Val Pro
            -10                 -5              -1  1

Ala Ser Cys Ala Ser Thr Ile Thr Pro Ala Cys Leu Gln Ala Leu Tyr
    5                   10                  15

Gly Ile Pro Thr Thr Lys Ala Thr Gln Ser Ser Asn Lys Leu Ala Val
20                  25                  30                  35

Ser Gly Phe Ile Asp Gln Phe Ala Asn Ser Ala Asp Leu Lys Thr Phe
                40                  45                  50

Leu Gly Lys Phe Arg Thr Asp Ile Ser Ser Ser Thr Thr Phe Thr Leu
            55                  60                  65

Gln Thr Leu Asp Gly Gly Ser Asn Ser Gln Ser Ser Ser Gln Ala Gly
        70                  75                  80

Val Glu Ala Asn Leu Asp Ile Gln Tyr Thr Val Gly Leu Ala Ser Ala
    85                  90                  95

Val Pro Thr Ile Phe Ile Ser Val Gly Asp Asp Phe Gln Asp Gly Asp
100                 105                 110                 115

Leu Glu Gly Phe Leu Asp Ile Ile Asn Phe Leu Leu Asn Glu Ser Ala
                120                 125                 130

Pro Pro Gln Val Leu Thr Thr Ser Tyr Gly Gln Asn Glu Asn Thr Ile
            135                 140                 145

Ser Ala Lys Leu Ala Asn Gln Leu Cys Asn Ala Tyr Ala Gln Leu Gly
        150                 155                 160
```

```
Ala Arg Gly Thr Ser Ile Leu Phe Ala Ser Gly Asp Gly Gly Val Ser
    165                 170                 175

Gly Ser Gln Ser Ser Ser Cys Ser Lys Phe Val Pro Thr Phe Pro Ser
180                 185                 190                 195

Gly Cys Pro Phe Met Thr Ser Val Gly Ala Thr Gln Gly Ile Asn Pro
                200                 205                 210

Glu Thr Ala Ala Asp Phe Ser Ser Gly Gly Phe Ser Asn Val Phe Ala
            215                 220                 225

Arg Pro Ser Tyr Gln Ser Thr Ala Val Ser Ser Tyr Leu Thr Ala Leu
        230                 235                 240

Gly Ser Thr Asn Ser Gly Lys Phe Asn Thr Ser Gly Arg Ala Phe Pro
    245                 250                 255

Asp Ile Ala Thr Gln Gly Val Asp Phe Glu Ile Val Val Ser Gly Arg
260                 265                 270                 275

Thr Glu Gly Val Asp Gly Thr Ser Cys Ala Ser Pro Thr Leu Ala Ala
                280                 285                 290

Ile Ile Ser Leu Leu Asn Asp Arg Leu Ile Ala Ala Gly Lys Ser Pro
            295                 300                 305

Leu Gly Phe Leu Asn Pro Phe Leu Tyr Ser Ala Ala Gly Thr Ala Ala
        310                 315                 320

Leu Thr Asp Ile Thr Ser Gly Ser Asn Pro Gly Cys Asn Thr Asn Gly
    325                 330                 335

Phe Pro Ala Lys Ala Gly Trp Asp Pro Val Thr Gly Leu Gly Thr Pro
340                 345                 350                 355

Asn Phe Ala Lys Leu Leu Thr Ala Val Gly Leu
                360                 365


<210> SEQ ID NO 19
<211> LENGTH: 366
<212> TYPE: PRT
<213> ORGANISM: Trametes cf versicolor
<220> FEATURE:
<221> NAME/KEY: mat_peptide
<222> LOCATION: (1)..(366)

<400> SEQUENCE: 19

Ala Val Pro Ala Ser Cys Ala Ser Thr Ile Thr Pro Ala Cys Leu Gln
1               5                   10                  15

Ala Leu Tyr Gly Ile Pro Thr Thr Lys Ala Thr Gln Ser Ser Asn Lys
            20                  25                  30

Leu Ala Val Ser Gly Phe Ile Asp Gln Phe Ala Asn Ser Ala Asp Leu
        35                  40                  45

Lys Thr Phe Leu Gly Lys Phe Arg Thr Asp Ile Ser Ser Ser Thr Thr
    50                  55                  60

Phe Thr Leu Gln Thr Leu Asp Gly Gly Ser Asn Ser Gln Ser Ser Ser
65                  70                  75                  80

Gln Ala Gly Val Glu Ala Asn Leu Asp Ile Gln Tyr Thr Val Gly Leu
                85                  90                  95

Ala Ser Ala Val Pro Thr Ile Phe Ile Ser Val Gly Asp Asp Phe Gln
            100                 105                 110

Asp Gly Asp Leu Glu Gly Phe Leu Asp Ile Ile Asn Phe Leu Leu Asn
        115                 120                 125

Glu Ser Ala Pro Pro Gln Val Leu Thr Thr Ser Tyr Gly Gln Asn Glu
    130                 135                 140

Asn Thr Ile Ser Ala Lys Leu Ala Asn Gln Leu Cys Asn Ala Tyr Ala
145                 150                 155                 160
```

```
Gln Leu Gly Ala Arg Gly Thr Ser Ile Leu Phe Ala Ser Gly Asp Gly
                165                 170                 175

Gly Val Ser Gly Ser Gln Ser Ser Ser Cys Ser Lys Phe Val Pro Thr
            180                 185                 190

Phe Pro Ser Gly Cys Pro Phe Met Thr Ser Val Gly Ala Thr Gln Gly
        195                 200                 205

Ile Asn Pro Glu Thr Ala Ala Asp Phe Ser Ser Gly Gly Phe Ser Asn
    210                 215                 220

Val Phe Ala Arg Pro Ser Tyr Gln Ser Thr Ala Val Ser Ser Tyr Leu
225                 230                 235                 240

Thr Ala Leu Gly Ser Thr Asn Ser Gly Lys Phe Asn Thr Ser Gly Arg
                245                 250                 255

Ala Phe Pro Asp Ile Ala Thr Gln Gly Val Asp Phe Glu Ile Val Val
            260                 265                 270

Ser Gly Arg Thr Glu Gly Val Asp Gly Thr Ser Cys Ala Ser Pro Thr
        275                 280                 285

Leu Ala Ala Ile Ile Ser Leu Leu Asn Asp Arg Leu Ile Ala Ala Gly
    290                 295                 300

Lys Ser Pro Leu Gly Phe Leu Asn Pro Phe Leu Tyr Ser Ala Ala Gly
305                 310                 315                 320

Thr Ala Ala Leu Thr Asp Ile Thr Ser Gly Ser Asn Pro Gly Cys Asn
                325                 330                 335

Thr Asn Gly Phe Pro Ala Lys Ala Gly Trp Asp Pro Val Thr Gly Leu
            340                 345                 350

Gly Thr Pro Asn Phe Ala Lys Leu Leu Thr Ala Val Gly Leu
        355                 360                 365
```

```
<210> SEQ ID NO 20
<211> LENGTH: 2088
<212> TYPE: DNA
<213> ORGANISM: Trametes versicolor
<220> FEATURE:
<221> NAME/KEY: CDS
<222> LOCATION: (1)..(258)
<220> FEATURE:
<221> NAME/KEY: sig_peptide
<222> LOCATION: (1)..(51)
<220> FEATURE:
<221> NAME/KEY: CDS
<222> LOCATION: (311)..(576)
<220> FEATURE:
<221> NAME/KEY: CDS
<222> LOCATION: (633)..(852)
<220> FEATURE:
<221> NAME/KEY: mat_peptide
<222> LOCATION: (706)..(2085)
<220> FEATURE:
<221> NAME/KEY: CDS
<222> LOCATION: (914)..(1024)
<220> FEATURE:
<221> NAME/KEY: CDS
<222> LOCATION: (1080)..(1279)
<220> FEATURE:
<221> NAME/KEY: CDS
<222> LOCATION: (1333)..(1470)
<220> FEATURE:
<221> NAME/KEY: CDS
<222> LOCATION: (1532)..(1979)
<220> FEATURE:
<221> NAME/KEY: CDS
<222> LOCATION: (2032)..(2085)

<400> SEQUENCE: 20

atg gtc gcc acc agc  ttg ctc gtt gcc tcc  ctg ttc acg ctt gtc        45
```

-continued

```
Met Val Ala Thr Ser  Leu Leu Val Ala Ser  Leu Phe Thr Leu Val
                -195                 -190                 -185

ctc ggc acc ccg acg  gct cgc aac ctc aag  ctg cat gag tct cgc        90
Leu Gly Thr Pro Thr  Ala Arg Asn Leu Lys  Leu His Glu Ser Arg
                -180                 -175                 -170

gag gag atc ccc gcc  ggc ttc tcg ctg agc  ggc gcc gcc tcg ccc       135
Glu Glu Ile Pro Ala  Gly Phe Ser Leu Ser  Gly Ala Ala Ser Pro
                -165                 -160                 -155

gac acg acg ctg aag  ctc cgc ctc gcg ctc  gtt cag agc aac ttc       180
Asp Thr Thr Leu Lys  Leu Arg Leu Ala Leu  Val Gln Ser Asn Phe
                -150                 -145                 -140

gcc gag ctt gag gac  aag ctc tac gac gtc  agc acc ccg tcg agc       225
Ala Glu Leu Glu Asp  Lys Leu Tyr Asp Val  Ser Thr Pro Ser Ser
                -135                 -130                 -125

gcg aac tac ggc cag  cac ctc tcc aag gag  gag gtacgtatgc            268
Ala Asn Tyr Gly Gln  His Leu Ser Lys Glu  Glu
                -120                 -115

ctcccatgtc gctttgcgca gttcactcac gatcgtgtgc ag gtc gag caa ctc      322
                                               Val Glu Gln Leu
                                                           -110

gtc gct ccc agt gcc  gcg tct gtc gcc gct  gtc aac gcc tgg ctc acc   370
Val Ala Pro Ser Ala  Ala Ser Val Ala Ala  Val Asn Ala Trp Leu Thr
                -105                 -100                 -95

gag aac ggt ctc act gcg cag acc atc tcg ccg gcc ggc gat tgg ttg     418
Glu Asn Gly Leu Thr Ala Gln Thr Ile Ser Pro Ala Gly Asp Trp Leu
            -90                 -85                 -80

gcg ttc gag gtg ccc gtc agc cag gcc aac gag ctc ttc gac gcc gac     466
Ala Phe Glu Val Pro Val Ser Gln Ala Asn Glu Leu Phe Asp Ala Asp
        -75                 -70                 -65

ttc tcc gtg ttc acc cac gac gaa tcc ggt ctc cag gct gtc cgg act     514
Phe Ser Val Phe Thr His Asp Glu Ser Gly Leu Gln Ala Val Arg Thr
    -60                 -55                 -50

ctc gcg tac tcc atc ccc gct gag ctg cag ggt cac ctg gac ctc gtc     562
Leu Ala Tyr Ser Ile Pro Ala Glu Leu Gln Gly His Leu Asp Leu Val
-45                 -40                 -35                 -30

cac ccc acg atc ac  gtcagtttcg ctgttccagt ccgattatag cgggtcctga     616
His Pro Thr Ile Thr
                -25

ccacttgctc caatag g ttc ccg aac cct aac tcg cac ctt ccc gtc gtg     666
                    Phe Pro Asn Pro Asn Ser His Leu Pro Val Val
                                    -20                 -15

cgc tcg ccc gtg aag ccc att cag aac ctc acc tcg cgc gcc gtc ccg     714
Arg Ser Pro Val Lys Pro Ile Gln Asn Leu Thr Ser Arg Ala Val Pro
            -10                 -5              -1   1

gct tcg tgc gct agc acc atc acc cct gcg tgc ctg cag gcg ctc tac     762
Ala Ser Cys Ala Ser Thr Ile Thr Pro Ala Cys Leu Gln Ala Leu Tyr
    5                   10                  15

ggc atc ccc acc acc aag gcc acc cag tcc tcg aac aag ctc gct gtc     810
Gly Ile Pro Thr Thr Lys Ala Thr Gln Ser Ser Asn Lys Leu Ala Val
20                  25                  30                  35

agc ggc ttc atc gac cag ttc gcc aac tcc gcc gac ttg aag             852
Ser Gly Phe Ile Asp Gln Phe Ala Asn Ser Ala Asp Leu Lys
                40                  45

gtgagtattc tggcgccctg gaggccatct tcggtgctga cgatcatgat gaaccttcca    912

g acc ttc ctc ggc aag ttc cgc acc gac atc tcg tcg tcg acg acc ttc    961
  Thr Phe Leu Gly Lys Phe Arg Thr Asp Ile Ser Ser Ser Thr Thr Phe
  50                  55                  60                  65

acc ctc cag acc ctc gac ggt gga tcc aac agc cag tcc agc agc cag    1009
Thr Leu Gln Thr Leu Asp Gly Gly Ser Asn Ser Gln Ser Ser Ser Gln
```

```
                70                  75                  80

gct ggt gtt gag gct gtaagtggcc ggcgatgctg ttacatggag actgggtgct     1064
Ala Gly Val Glu Ala
            85

gacagcttga cgtag aac ttg gac gtc cag tac gct atc ggc atc gcc acg     1115
                 Asn Leu Asp Val Gln Tyr Ala Ile Gly Ile Ala Thr
                             90                  95

ggc gtc cct acc acc ttc atc tcc gtc ggt gac gac ttc cag gac ggt     1163
Gly Val Pro Thr Thr Phe Ile Ser Val Gly Asp Asp Phe Gln Asp Gly
    100                 105                 110

gac ctc gag ggc ttc ctc gac atc atc aac ttc ctc ctc aac gaa agc     1211
Asp Leu Glu Gly Phe Leu Asp Ile Ile Asn Phe Leu Leu Asn Glu Ser
115                 120                 125                 130

gcg ccc ccg cag gtg ctc acg acc agc tac ggc cag aac gag aac acc     1259
Ala Pro Pro Gln Val Leu Thr Thr Ser Tyr Gly Gln Asn Glu Asn Thr
                135                 140                 145

atc tcc gcc aag ctt gcc aa  gtacgtgtga gcgcgctact gggaatactg        1309
Ile Ser Ala Lys Leu Ala Asn
            150

tacactgacc ttcgtcttta cag c caa ctc tgc aac gca tac gct cag ctc     1360
                            Gln Leu Cys Asn Ala Tyr Ala Gln Leu
                                155                 160

ggc gcg cgt ggc acc tcc atc ctc ttc gcg tcc ggc gac ggt ggt gtt     1408
Gly Ala Arg Gly Thr Ser Ile Leu Phe Ala Ser Gly Asp Gly Gly Val
        165                 170                 175

gcc ggc tcg cag acc tcc agc tgc acc aag ttc ctg ccg acc ttc ccc     1456
Ala Gly Ser Gln Thr Ser Ser Cys Thr Lys Phe Leu Pro Thr Phe Pro
    180                 185                 190

tcg ggc tgc ccc tt  gtacgtcatt acgttcaacc ctctccgttc gaaacgctaa     1510
Ser Gly Cys Pro Phe
195

cacagtaccc gcttatcgca g c atg acc tcc gtc ggc gcg acg cag ggc atc   1562
                          Met Thr Ser Val Gly Ala Thr Gln Gly Ile
                          200                 205

aac ccg gag acc gcc gcc gac ttc tcc tcc ggc ggc ttc tca aac gtc     1610
Asn Pro Glu Thr Ala Ala Asp Phe Ser Ser Gly Gly Phe Ser Asn Val
210                 215                 220                 225

ttc gcc cgc ccc tcg tac cag tct acc gcc gtc agc agc tac ctg acc     1658
Phe Ala Arg Pro Ser Tyr Gln Ser Thr Ala Val Ser Ser Tyr Leu Thr
                230                 235                 240

gcg ctc ggc agc acc aac tcg ggc aag ttc aac acc tcc ggc cgc gcg     1706
Ala Leu Gly Ser Thr Asn Ser Gly Lys Phe Asn Thr Ser Gly Arg Ala
            245                 250                 255

ttc ccc gac atc gcc acc cag ggt gtc gac ttc gag atc gtc gtt ggc     1754
Phe Pro Asp Ile Ala Thr Gln Gly Val Asp Phe Glu Ile Val Val Gly
        260                 265                 270

ggc cgc act gag ggc gtc gac ggc act agc tgc gcc agc ccg acg ctt     1802
Gly Arg Thr Glu Gly Val Asp Gly Thr Ser Cys Ala Ser Pro Thr Leu
    275                 280                 285

gcc gcg atc atc tcg ctc ctg aac gac cgc ctc atc gcg gcc ggc aag     1850
Ala Ala Ile Ile Ser Leu Leu Asn Asp Arg Leu Ile Ala Ala Gly Lys
290                 295                 300                 305

agc ccc ctt ggc ttc ctc aac ccc ttc ctg tac tcg gcg gcg ggc gcc     1898
Ser Pro Leu Gly Phe Leu Asn Pro Phe Leu Tyr Ser Ala Ala Gly Ala
                310                 315                 320

gcg gca ctc acc gac atc acg tct ggc tcg aac ccc ggt tgc ggc acc     1946
Ala Ala Leu Thr Asp Ile Thr Ser Gly Ser Asn Pro Gly Cys Gly Thr
            325                 330                 335

aac ggc ttc ccc gcg aag gct ggc tgg gac ccg gtacgtttct gtctccgtag   1999
```

-continued

```
Asn Gly Phe Pro Ala Lys Ala Gly Trp Asp Pro
        340                 345

cgcgcccgaa acataaactg acggctttgc ag gtc acc ggt ctt ggc acg ccc     2052
                                    Val Thr Gly Leu Gly Thr Pro
                                        350                 355

aac ttc gcc aag ctg ctc act gct gtt ggc ctg taa                     2088
Asn Phe Ala Lys Leu Leu Thr Ala Val Gly Leu
                360                 365


<210> SEQ ID NO 21
<211> LENGTH: 565
<212> TYPE: PRT
<213> ORGANISM: Trametes versicolor

<400> SEQUENCE: 21

Met Val Ala Thr Ser  Leu Leu Val Ala Ser  Leu Phe Thr Leu Val
              -195                 -190                 -185

Leu Gly Thr Pro Thr  Ala Arg Asn Leu Lys  Leu His Glu Ser Arg
              -180                 -175                 -170

Glu Glu Ile Pro Ala  Gly Phe Ser Leu Ser  Gly Ala Ala Ser Pro
              -165                 -160                 -155

Asp Thr Thr Leu Lys  Leu Arg Leu Ala Leu  Val Gln Ser Asn Phe
              -150                 -145                 -140

Ala Glu Leu Glu Asp  Lys Leu Tyr Asp Val  Ser Thr Pro Ser Ser
              -135                 -130                 -125

Ala Asn Tyr Gly Gln  His Leu Ser Lys Glu  Glu Val Glu Gln Leu
              -120                 -115                 -110

Val Ala Pro Ser Ala  Ala Ser Val Ala Ala  Val Asn Ala Trp Leu Thr
              -105                 -100                 -95

Glu Asn Gly Leu Thr Ala Gln Thr Ile Ser Pro Ala Gly Asp Trp Leu
            -90                 -85                 -80

Ala Phe Glu Val Pro Val Ser Gln Ala Asn Glu Leu Phe Asp Ala Asp
        -75                 -70                 -65

Phe Ser Val Phe Thr His Asp Glu Ser Gly Leu Gln Ala Val Arg Thr
    -60                 -55                 -50

Leu Ala Tyr Ser Ile Pro Ala Glu Leu Gln Gly His Leu Asp Leu Val
-45                 -40                 -35                 -30

His Pro Thr Ile Thr Phe Pro Asn Pro Asn Ser His Leu Pro Val Val
              -25                 -20                 -15

Arg Ser Pro Val Lys Pro Ile Gln Asn Leu Thr Ser Arg Ala Val Pro
            -10                 -5              -1  1

Ala Ser Cys Ala Ser Thr Ile Thr Pro Ala Cys Leu Gln Ala Leu Tyr
    5                   10                  15

Gly Ile Pro Thr Thr Lys Ala Thr Gln Ser Ser Asn Lys Leu Ala Val
20                  25                  30                  35

Ser Gly Phe Ile Asp Gln Phe Ala Asn Ser Ala Asp Leu Lys Thr Phe
              40                  45                  50

Leu Gly Lys Phe Arg Thr Asp Ile Ser Ser Ser Thr Thr Phe Thr Leu
            55                  60                  65

Gln Thr Leu Asp Gly Gly Ser Asn Ser Gln Ser Ser Ser Gln Ala Gly
        70                  75                  80

Val Glu Ala Asn Leu Asp Val Gln Tyr Ala Ile Gly Ile Ala Thr Gly
    85                  90                  95

Val Pro Thr Thr Phe Ile Ser Val Gly Asp Asp Phe Gln Asp Gly Asp
100                 105                 110                 115
```

```
Leu Glu Gly Phe Leu Asp Ile Ile Asn Phe Leu Leu Asn Glu Ser Ala
                120                 125                 130

Pro Pro Gln Val Leu Thr Thr Ser Tyr Gly Gln Asn Glu Asn Thr Ile
            135                 140                 145

Ser Ala Lys Leu Ala Asn Gln Leu Cys Asn Ala Tyr Ala Gln Leu Gly
        150                 155                 160

Ala Arg Gly Thr Ser Ile Leu Phe Ala Ser Gly Asp Gly Gly Val Ala
    165                 170                 175

Gly Ser Gln Thr Ser Ser Cys Thr Lys Phe Leu Pro Thr Phe Pro Ser
180                 185                 190                 195

Gly Cys Pro Phe Met Thr Ser Val Gly Ala Thr Gln Gly Ile Asn Pro
                200                 205                 210

Glu Thr Ala Ala Asp Phe Ser Ser Gly Gly Phe Ser Asn Val Phe Ala
            215                 220                 225

Arg Pro Ser Tyr Gln Ser Thr Ala Val Ser Ser Tyr Leu Thr Ala Leu
        230                 235                 240

Gly Ser Thr Asn Ser Gly Lys Phe Asn Thr Ser Gly Arg Ala Phe Pro
    245                 250                 255

Asp Ile Ala Thr Gln Gly Val Asp Phe Glu Ile Val Val Gly Gly Arg
260                 265                 270                 275

Thr Glu Gly Val Asp Gly Thr Ser Cys Ala Ser Pro Thr Leu Ala Ala
                280                 285                 290

Ile Ile Ser Leu Leu Asn Asp Arg Leu Ile Ala Ala Gly Lys Ser Pro
            295                 300                 305

Leu Gly Phe Leu Asn Pro Phe Leu Tyr Ser Ala Ala Gly Ala Ala Ala
        310                 315                 320

Leu Thr Asp Ile Thr Ser Gly Ser Asn Pro Gly Cys Gly Thr Asn Gly
    325                 330                 335

Phe Pro Ala Lys Ala Gly Trp Asp Pro Val Thr Gly Leu Gly Thr Pro
340                 345                 350                 355

Asn Phe Ala Lys Leu Leu Thr Ala Val Gly Leu
                360                 365


<210> SEQ ID NO 22
<211> LENGTH: 1698
<212> TYPE: DNA
<213> ORGANISM: Artificial Sequence
<220> FEATURE:
<223> OTHER INFORMATION: Synthetic construct
<220> FEATURE:
<221> NAME/KEY: CDS
<222> LOCATION: (1)..(1695)
<220> FEATURE:
<221> NAME/KEY: sig_peptide
<222> LOCATION: (1)..(51)
<220> FEATURE:
<221> NAME/KEY: mat_peptide
<222> LOCATION: (598)..(1695)

<400> SEQUENCE: 22

atg gtc gca aca tcg  ttg ttg gtg gca tcg  ttg ttc aca ttg gtc        45
Met Val Ala Thr Ser  Leu Leu Val Ala Ser  Leu Phe Thr Leu Val
                -195                 -190                 -185

ttg gga aca ccg aca  gca cgc aac ttg aaa  ttg cat gaa tcc cga        90
Leu Gly Thr Pro Thr  Ala Arg Asn Leu Lys  Leu His Glu Ser Arg
                -180                 -175                 -170

gag gaa att cct gca  gga ttc tcg ttg tcg  gga gca gca tcg cct       135
Glu Glu Ile Pro Ala  Gly Phe Ser Leu Ser  Gly Ala Ala Ser Pro
                -165                 -160                 -155
```

-continued

```
gat aca aca ttg aaa  ttg cgg ttg gca ttg  gtc cag tcg aac ttc        180
Asp Thr Thr Leu Lys  Leu Arg Leu Ala Leu  Val Gln Ser Asn Phe
                -150                 -145                 -140

gca gag ttg gag gac  aaa ttg tat gat gtc  tcg aca cct tcg tcg        225
Ala Glu Leu Glu Asp  Lys Leu Tyr Asp Val  Ser Thr Pro Ser Ser
                -135                 -130                 -125

gca aac tat gga cag  cac ttg tcc aaa gag  gag gtc gag cag ttg        270
Ala Asn Tyr Gly Gln  His Leu Ser Lys Glu  Glu Val Glu Gln Leu
                -120                 -115                 -110

gtc gca ccc tcg gca  gca tcg gtg gca gca  gtc aac gca tgg ttg aca    318
Val Ala Pro Ser Ala  Ala Ser Val Ala Ala  Val Asn Ala Trp Leu Thr
                -105                 -100                 -95

gaa aac gga ttg aca gca cag aca att tcg cct gca gga gat tgg ttg      366
Glu Asn Gly Leu Thr Ala Gln Thr Ile Ser Pro Ala Gly Asp Trp Leu
            -90                 -85                 -80

gca ttc gag gtg cct gtc tcg cag gca aac gag ttg ttc gat gca gat      414
Ala Phe Glu Val Pro Val Ser Gln Ala Asn Glu Leu Phe Asp Ala Asp
        -75                 -70                 -65

ttc tcg gtg ttc aca cat gat gag tcg gga ttg cag gca gtc cga aca      462
Phe Ser Val Phe Thr His Asp Glu Ser Gly Leu Gln Ala Val Arg Thr
    -60                 -55                 -50

ttg gca tat tcg att ccc gca gaa ttg cag gga cac ttg gat ttg gtg      510
Leu Ala Tyr Ser Ile Pro Ala Glu Leu Gln Gly His Leu Asp Leu Val
-45                 -40                 -35                 -30

cat ccc aca att aca ttc ccc aac ccc aac tcg cat ttg ccc gtc gtg      558
His Pro Thr Ile Thr Phe Pro Asn Pro Asn Ser His Leu Pro Val Val
                -25                 -20                 -15

cgg tcg cct gtc aaa cct att cag aac ttg aca tcc cga gca gtg cct      606
Arg Ser Pro Val Lys Pro Ile Gln Asn Leu Thr Ser Arg Ala Val Pro
            -10                 -5                  -1  1

gca tcc tgt gca tcg aca att aca ccg gca tgt ttg cag gca ttg tat      654
Ala Ser Cys Ala Ser Thr Ile Thr Pro Ala Cys Leu Gln Ala Leu Tyr
    5                   10                  15

gga att cct aca aca aaa gca aca cag tcg tcc aac aaa ttg gca gtc      702
Gly Ile Pro Thr Thr Lys Ala Thr Gln Ser Ser Asn Lys Leu Ala Val
20                  25                  30                  35

tcg gga ttc att gat cag ttc gca aac tcc gca gat ttg aaa aca ttc      750
Ser Gly Phe Ile Asp Gln Phe Ala Asn Ser Ala Asp Leu Lys Thr Phe
                40                  45                  50

ttg ggc aaa ttc cgc aca gac att tcg tcg tcg aca aca ttc aca ttg      798
Leu Gly Lys Phe Arg Thr Asp Ile Ser Ser Ser Thr Thr Phe Thr Leu
            55                  60                  65

cag aca ttg gat gga ggc tcc aac tcg cag tcg tcg tcg cag gca gga      846
Gln Thr Leu Asp Gly Gly Ser Asn Ser Gln Ser Ser Ser Gln Ala Gly
        70                  75                  80

gtg gaa gca aac ttg gat gtc cag tat gca atc gga att gca aca gga      894
Val Glu Ala Asn Leu Asp Val Gln Tyr Ala Ile Gly Ile Ala Thr Gly
    85                  90                  95

gtc cct aca aca ttc att tcg gtc gga gat gat ttc cag gat gga gat      942
Val Pro Thr Thr Phe Ile Ser Val Gly Asp Asp Phe Gln Asp Gly Asp
100                 105                 110                 115

ttg gaa gga ttc ttg gac atc att aac ttc ttg ttg aac gaa tcg gca      990
Leu Glu Gly Phe Leu Asp Ile Ile Asn Phe Leu Leu Asn Glu Ser Ala
                120                 125                 130

ccc cct cag gtc ttg aca aca tcc tat gga cag aac gaa aac aca att     1038
Pro Pro Gln Val Leu Thr Thr Ser Tyr Gly Gln Asn Glu Asn Thr Ile
            135                 140                 145

tcc gcc aaa ttg gca aac cag ttg tgt aac gca tat gca cag ttg gga     1086
Ser Ala Lys Leu Ala Asn Gln Leu Cys Asn Ala Tyr Ala Gln Leu Gly
        150                 155                 160
```

```
gca cgg gga aca tcg atc ttg ttc gca tcc ggc gat gga gga gtc gca     1134
Ala Arg Gly Thr Ser Ile Leu Phe Ala Ser Gly Asp Gly Gly Val Ala
    165                 170                 175

gga tcg cag aca tcg tcg tgt aca aag ttc ttg ccc aca ttc ccc tcc     1182
Gly Ser Gln Thr Ser Ser Cys Thr Lys Phe Leu Pro Thr Phe Pro Ser
180                 185                 190                 195

gga tgt ccc ttc atg aca tcc gtc ggc gca aca cag ggc att aac cct     1230
Gly Cys Pro Phe Met Thr Ser Val Gly Ala Thr Gln Gly Ile Asn Pro
                200                 205                 210

gaa aca gcc gcc gat ttc tcg tcg ggc gga ttc tcg aac gtg ttc gca     1278
Glu Thr Ala Ala Asp Phe Ser Ser Gly Gly Phe Ser Asn Val Phe Ala
            215                 220                 225

agg ccg tcg tat cag tcg aca gca gtc tcg tcg tat ttg aca gca ttg     1326
Arg Pro Ser Tyr Gln Ser Thr Ala Val Ser Ser Tyr Leu Thr Ala Leu
        230                 235                 240

gga tcg aca aac tcg ggc aaa ttc aac aca tcc gga cga gca ttc ccg     1374
Gly Ser Thr Asn Ser Gly Lys Phe Asn Thr Ser Gly Arg Ala Phe Pro
    245                 250                 255

gat att gca aca cag gga gtc gat ttc gag att gtc gtc gga gga agg     1422
Asp Ile Ala Thr Gln Gly Val Asp Phe Glu Ile Val Val Gly Gly Arg
260                 265                 270                 275

aca gaa gga gtg gat gga aca tcc tgt gca tcc ccg aca ttg gca gcc     1470
Thr Glu Gly Val Asp Gly Thr Ser Cys Ala Ser Pro Thr Leu Ala Ala
                280                 285                 290

atc att tcc ttg ttg aac gat cga ttg att gca gca gga aaa tcc ccc     1518
Ile Ile Ser Leu Leu Asn Asp Arg Leu Ile Ala Ala Gly Lys Ser Pro
            295                 300                 305

ttg gga ttc ttg aac cct ttc ttg tat tcc gcc gca ggc gcc gcc gca     1566
Leu Gly Phe Leu Asn Pro Phe Leu Tyr Ser Ala Ala Gly Ala Ala Ala
        310                 315                 320

ttg aca gac att aca tcg ggc tcc aac cct gga tgt gga aca aac gga     1614
Leu Thr Asp Ile Thr Ser Gly Ser Asn Pro Gly Cys Gly Thr Asn Gly
    325                 330                 335

ttc cct gca aaa gca gga tgg gac cct gtc aca gga ttg gga aca ccc     1662
Phe Pro Ala Lys Ala Gly Trp Asp Pro Val Thr Gly Leu Gly Thr Pro
340                 345                 350                 355

aac ttc gcc aaa ttg ttg aca gca gtg gga ttg taa                     1698
Asn Phe Ala Lys Leu Leu Thr Ala Val Gly Leu
                360                 365


<210> SEQ ID NO 23
<211> LENGTH: 565
<212> TYPE: PRT
<213> ORGANISM: Artificial Sequence
<220> FEATURE:
<223> OTHER INFORMATION: Synthetic Construct

<400> SEQUENCE: 23

Met Val Ala Thr Ser  Leu Leu Val Ala Ser  Leu Phe Thr Leu Val
                -195                 -190                 -185

Leu Gly Thr Pro Thr  Ala Arg Asn Leu Lys  Leu His Glu Ser Arg
                -180                 -175                 -170

Glu Glu Ile Pro Ala  Gly Phe Ser Leu Ser  Gly Ala Ala Ser Pro
                -165                 -160                 -155

Asp Thr Thr Leu Lys  Leu Arg Leu Ala Leu  Val Gln Ser Asn Phe
                -150                 -145                 -140

Ala Glu Leu Glu Asp  Lys Leu Tyr Asp Val  Ser Thr Pro Ser Ser
                -135                 -130                 -125

Ala Asn Tyr Gly Gln  His Leu Ser Lys Glu  Glu Val Glu Gln Leu
```

-continued

```
                -120                -115                -110

Val Ala Pro Ser Ala  Ala Ser Val Ala Ala  Val Asn Ala Trp Leu Thr
                -105                -100                -95

Glu Asn Gly Leu Thr Ala Gln Thr Ile Ser Pro Ala Gly Asp Trp Leu
            -90                 -85                 -80

Ala Phe Glu Val Pro Val Ser Gln Ala Asn Glu Leu Phe Asp Ala Asp
        -75                 -70                 -65

Phe Ser Val Phe Thr His Asp Glu Ser Gly Leu Gln Ala Val Arg Thr
    -60                 -55                 -50

Leu Ala Tyr Ser Ile Pro Ala Glu Leu Gln Gly His Leu Asp Leu Val
-45                 -40                 -35                 -30

His Pro Thr Ile Thr Phe Pro Asn Pro Asn Ser His Leu Pro Val Val
                -25                 -20                 -15

Arg Ser Pro Val Lys Pro Ile Gln Asn Leu Thr Ser Arg Ala Val Pro
            -10                 -5                  -1  1

Ala Ser Cys Ala Ser Thr Ile Thr Pro Ala Cys Leu Gln Ala Leu Tyr
    5                   10                  15

Gly Ile Pro Thr Thr Lys Ala Thr Gln Ser Ser Asn Lys Leu Ala Val
20                  25                  30                  35

Ser Gly Phe Ile Asp Gln Phe Ala Asn Ser Ala Asp Leu Lys Thr Phe
                40                  45                  50

Leu Gly Lys Phe Arg Thr Asp Ile Ser Ser Ser Thr Thr Phe Thr Leu
            55                  60                  65

Gln Thr Leu Asp Gly Gly Ser Asn Ser Gln Ser Ser Ser Gln Ala Gly
        70                  75                  80

Val Glu Ala Asn Leu Asp Val Gln Tyr Ala Ile Gly Ile Ala Thr Gly
    85                  90                  95

Val Pro Thr Thr Phe Ile Ser Val Gly Asp Asp Phe Gln Asp Gly Asp
100                 105                 110                 115

Leu Glu Gly Phe Leu Asp Ile Ile Asn Phe Leu Leu Asn Glu Ser Ala
                120                 125                 130

Pro Pro Gln Val Leu Thr Thr Ser Tyr Gly Gln Asn Glu Asn Thr Ile
            135                 140                 145

Ser Ala Lys Leu Ala Asn Gln Leu Cys Asn Ala Tyr Ala Gln Leu Gly
        150                 155                 160

Ala Arg Gly Thr Ser Ile Leu Phe Ala Ser Gly Asp Gly Gly Val Ala
    165                 170                 175

Gly Ser Gln Thr Ser Ser Cys Thr Lys Phe Leu Pro Thr Phe Pro Ser
180                 185                 190                 195

Gly Cys Pro Phe Met Thr Ser Val Gly Ala Thr Gln Gly Ile Asn Pro
                200                 205                 210

Glu Thr Ala Ala Asp Phe Ser Ser Gly Gly Phe Ser Asn Val Phe Ala
            215                 220                 225

Arg Pro Ser Tyr Gln Ser Thr Ala Val Ser Ser Tyr Leu Thr Ala Leu
        230                 235                 240

Gly Ser Thr Asn Ser Gly Lys Phe Asn Thr Ser Gly Arg Ala Phe Pro
    245                 250                 255

Asp Ile Ala Thr Gln Gly Val Asp Phe Glu Ile Val Val Gly Gly Arg
260                 265                 270                 275

Thr Glu Gly Val Asp Gly Thr Ser Cys Ala Ser Pro Thr Leu Ala Ala
                280                 285                 290

Ile Ile Ser Leu Leu Asn Asp Arg Leu Ile Ala Ala Gly Lys Ser Pro
            295                 300                 305
```

```
Leu Gly Phe Leu Asn Pro Phe Leu Tyr Ser Ala Ala Gly Ala Ala Ala
        310                 315                 320

Leu Thr Asp Ile Thr Ser Gly Ser Asn Pro Gly Cys Gly Thr Asn Gly
    325                 330                 335

Phe Pro Ala Lys Ala Gly Trp Asp Pro Val Thr Gly Leu Gly Thr Pro
340                 345                 350                 355

Asn Phe Ala Lys Leu Leu Thr Ala Val Gly Leu
                360                 365


<210> SEQ ID NO 24
<211> LENGTH: 366
<212> TYPE: PRT
<213> ORGANISM: Trametes versicolor
<220> FEATURE:
<221> NAME/KEY: mat_polypepitde
<222> LOCATION: (1)..(366)

<400> SEQUENCE: 24

Ala Val Pro Ala Ser Cys Ala Ser Thr Ile Thr Pro Ala Cys Leu Gln
1               5                   10                  15

Ala Leu Tyr Gly Ile Pro Thr Thr Lys Ala Thr Gln Ser Ser Asn Lys
            20                  25                  30

Leu Ala Val Ser Gly Phe Ile Asp Gln Phe Ala Asn Ser Ala Asp Leu
        35                  40                  45

Lys Thr Phe Leu Gly Lys Phe Arg Thr Asp Ile Ser Ser Ser Thr Thr
    50                  55                  60

Phe Thr Leu Gln Thr Leu Asp Gly Gly Ser Asn Ser Gln Ser Ser Ser
65                  70                  75                  80

Gln Ala Gly Val Glu Ala Asn Leu Asp Val Gln Tyr Ala Ile Gly Ile
                85                  90                  95

Ala Thr Gly Val Pro Thr Thr Phe Ile Ser Val Gly Asp Asp Phe Gln
            100                 105                 110

Asp Gly Asp Leu Glu Gly Phe Leu Asp Ile Ile Asn Phe Leu Leu Asn
        115                 120                 125

Glu Ser Ala Pro Pro Gln Val Leu Thr Thr Ser Tyr Gly Gln Asn Glu
    130                 135                 140

Asn Thr Ile Ser Ala Lys Leu Ala Asn Gln Leu Cys Asn Ala Tyr Ala
145                 150                 155                 160

Gln Leu Gly Ala Arg Gly Thr Ser Ile Leu Phe Ala Ser Gly Asp Gly
                165                 170                 175

Gly Val Ala Gly Ser Gln Thr Ser Ser Cys Thr Lys Phe Leu Pro Thr
            180                 185                 190

Phe Pro Ser Gly Cys Pro Phe Met Thr Ser Val Gly Ala Thr Gln Gly
        195                 200                 205

Ile Asn Pro Glu Thr Ala Ala Asp Phe Ser Ser Gly Gly Phe Ser Asn
    210                 215                 220

Val Phe Ala Arg Pro Ser Tyr Gln Ser Thr Ala Val Ser Ser Tyr Leu
225                 230                 235                 240

Thr Ala Leu Gly Ser Thr Asn Ser Gly Lys Phe Asn Thr Ser Gly Arg
                245                 250                 255

Ala Phe Pro Asp Ile Ala Thr Gln Gly Val Asp Phe Glu Ile Val Val
            260                 265                 270

Gly Gly Arg Thr Glu Gly Val Asp Gly Thr Ser Cys Ala Ser Pro Thr
        275                 280                 285

Leu Ala Ala Ile Ile Ser Leu Leu Asn Asp Arg Leu Ile Ala Ala Gly
```

```
    290                 295                 300

Lys Ser Pro Leu Gly Phe Leu Asn Pro Phe Leu Tyr Ser Ala Ala Gly
305                 310                 315                 320

Ala Ala Ala Leu Thr Asp Ile Thr Ser Gly Ser Asn Pro Gly Cys Gly
                325                 330                 335

Thr Asn Gly Phe Pro Ala Lys Ala Gly Trp Asp Pro Val Thr Gly Leu
            340                 345                 350

Gly Thr Pro Asn Phe Ala Lys Leu Leu Thr Ala Val Gly Leu
        355                 360                 365


<210> SEQ ID NO 25
<211> LENGTH: 567
<212> TYPE: PRT
<213> ORGANISM: Dichomitus squalens

<400> SEQUENCE: 25

Met Val Ala Ser Gly Leu Phe Leu Ala Ser Leu Ile Ala Leu Ala Leu
1               5                   10                  15

Gly Lys Pro Thr Ala Arg Asn Leu Lys Leu His Glu Ser Arg Pro Ser
            20                  25                  30

Ala Pro Asn Gly Phe Ser Leu Val Gly Ser Ala Asp Ser Asn Arg Thr
        35                  40                  45

Leu Lys Leu Arg Leu Ala Leu Ala Glu Ser Asn Phe Ser Glu Leu Glu
    50                  55                  60

Arg Lys Leu Tyr Asp Val Ser Thr Pro Lys Ser Ala Asn Tyr Gly Lys
65                  70                  75                  80

His Leu Ser Lys Ala Glu Val Gln Gln Leu Val Ala Pro Gly Gln Asp
                85                  90                  95

Ser Ile Asp Ala Val Asn Ser Trp Leu Lys Glu Asn Asp Ile Thr Ala
            100                 105                 110

Lys Thr Ile Ser Ser Thr Gly Glu Trp Ile Ser Phe Glu Val Pro Val
        115                 120                 125

Ser Lys Ala Asn Asp Leu Phe Asp Ala Asp Phe Ser Val Phe Lys His
    130                 135                 140

Asp Asp Thr Gly Val Glu Ala Ile Arg Thr Leu Ser Tyr Ser Ile Pro
145                 150                 155                 160

Ala Glu Leu Gln Gly His Leu Asp Leu Val His Pro Thr Val Thr Phe
                165                 170                 175

Pro Asn Pro Tyr Ser His Leu Pro Val Phe Gln Ser Pro Val Lys Lys
            180                 185                 190

Thr Ala Glu Ile Gln Asn Phe Thr Ala Gly Ala Ile Pro Ser Ser Cys
        195                 200                 205

Ser Ser Thr Ile Thr Pro Ala Cys Leu Gln Ala Ile Tyr Asn Ile Pro
    210                 215                 220

Thr Thr Ala Ala Thr Glu Ser Ser Asn Gln Leu Gly Val Thr Gly Phe
225                 230                 235                 240

Ile Asp Gln Tyr Ala Asn Lys Lys Asp Leu Lys Thr Phe Leu Lys Lys
                245                 250                 255

Tyr Arg Thr Asp Ile Ser Ser Ser Thr Thr Phe Thr Leu Gln Thr Leu
            260                 265                 270

Asp Gly Gly Ser Asn Ser Gln Thr Gly Ser Lys Ala Gly Val Glu Ala
        275                 280                 285

Asn Leu Asp Ile Gln Tyr Thr Val Gly Val Ala Thr Gly Val Pro Thr
    290                 295                 300
```

-continued

```
Thr Phe Ile Ser Val Gly Asp Asp Phe Gln Asp Gly Asp Leu Glu Gly
305                 310                 315                 320

Phe Leu Asp Val Ile Asn Ala Leu Leu Asp Glu Asp Ala Pro Pro Ser
                325                 330                 335

Val Leu Thr Thr Ser Tyr Gly Gln Asp Glu Ser Thr Ile Ser Arg Ala
            340                 345                 350

Leu Ala Val Lys Leu Cys Asn Ala Tyr Ala Gln Leu Gly Ala Arg Gly
        355                 360                 365

Val Ser Ile Leu Phe Ala Ser Gly Asp Gly Gly Val Ser Gly Ser Gln
    370                 375                 380

Ser Ala Ser Cys Ser Lys Phe Val Pro Thr Phe Pro Ser Gly Cys Pro
385                 390                 395                 400

Tyr Met Thr Ser Val Gly Ala Thr Gln Gly Val Asn Pro Glu Thr Ala
                405                 410                 415

Ala Asp Phe Ser Ser Gly Gly Phe Ser Asn Tyr Trp Gly Val Pro Asp
            420                 425                 430

Tyr Gln Ser Asp Ala Val Ser Thr Tyr Leu Ser Ala Leu Gly Lys Thr
        435                 440                 445

Asn Ser Gly Lys Tyr Asn Ala Ser Gly Arg Gly Phe Pro Asp Val Ser
    450                 455                 460

Thr Gln Gly Val Ser Phe Glu Val Val Val Asp Gly Ser Val Glu Ala
465                 470                 475                 480

Val Asp Gly Thr Ser Cys Ala Ser Pro Thr Phe Ala Ser Ile Ile Ser
                485                 490                 495

Leu Val Asn Asp Lys Leu Val Ala Ala Gly Lys Ser Pro Leu Gly Phe
            500                 505                 510

Leu Asn Pro Phe Leu Tyr Ser Asp Gly Val Ala Ala Leu Asn Asp Ile
        515                 520                 525

Thr Ser Gly Ser Asn Pro Gly Cys Asn Thr Asn Gly Phe Pro Ala Lys
    530                 535                 540

Lys Gly Trp Asp Pro Val Thr Gly Leu Gly Thr Pro Asp Phe Lys Lys
545                 550                 555                 560

Leu Leu Thr Ala Val Gly Leu
                565
```

POLYPEPTIDES HAVING PROTEASE ACTIVITY

CROSS-REFERENCE TO RELATED APPLICATIONS

This application is a divisional of U.S. application Ser. No. 15/673,594 filed on Aug. 10, 2017, now U.S. Pat. No. 10,006,017, which is a divisional of U.S. application Ser. No. 14/423,546 filed on Feb. 24, 2015, now U.S. Pat. No. 9,771,570, which is a 35 U.S.C. 371 national application of international application no. PCT/EP2013/068361 filed on Sep. 5, 2013, which claims priority or the benefit under 35 U.S.C. 119 of European application no. 12183079.8 filed on Sep. 5, 2012 and U.S. provisional application No. 61/697,032 filed Sep. 5, 2012. The content of these applications is fully incorporated herein by reference.

REFERENCE TO A SEQUENCE LISTING

This application contains a Sequence Listing in computer readable form, which is incorporated herein by reference.

BACKGROUND OF THE INVENTION

Field of the Invention

The present invention relates to isolated polypeptides having protease activity and isolated nucleic acid sequences encoding the proteases. The invention also relates to nucleic acid constructs, vectors, and host cells, including plant and animal cells, comprising the nucleic acid sequences, as well as methods for producing and using the proteases, in particular, the use of the proteases in animal feed.

Background of the Invention

In the use of proteases in animal feed (in vivo), and/or the use of such proteases for treating vegetable proteins (in vitro) it is noted that proteins are essential nutritional factors for animals and humans. Humans and livestock usually get the necessary proteins from vegetable protein sources. Important vegetable protein sources are, e.g., oilseed crops, legumes and cereals.

When, e.g., soybean meal is included in the feed of mono-gastric animals such as pigs and poultry, a significant proportion of the soybean meal is not digested efficiently (the apparent ileal protein digestibility in piglets, growing pigs and poultry such as broilers, laying hens and roosters is only around 80%).

The gastrointestinal tract of animals consists of a series of segments each representing different pH environments. In mono-gastric animals such as pigs and poultry and many types of fish, the stomach is strongly acidic with a pH potentially as low as 1-2, while the intestine has a more neutral pH of around 6-7.5. Apart from the stomach and intestine, poultry also have a crop preceding the stomach. The pH in the crop is mostly determined by the feed ingested and hence typically lies in the range of pH 4-6. Protein digestion by a protease may occur along the entire digestive tract, provided that the protease is active and survives the conditions in the digestive tract. Hence, proteases which are highly acid stable and so can survive in the gastric environment and at the same time are efficiently active at the broad range of physiological pH of the digestive tract in the target animal are especially desirable. The novel S53 proteases of the invention are useful for these purposes.

Since animal feed is often formulated in pelleted form, in which steam is applied in the pelleting process, it is also desirable that proteases used in animal feed are capable of remaining active after exposure to said steam treatment.

In order to produce a protease for industrial use, it is important that the protease is produced in high yields making the product available in sufficient quantities in order to be able to provide the protease at a favourable price.

DESCRIPTION OF THE RELATED ART

S53 proteases are known in the art. An S53 peptide from *Grifola frondosa* with accession number MER078639 (SEQ ID NO: 9) has 83.6% sequence identity to SEQ ID NO: 5. An S53 protease from *Postia placenta* (UniProt: B8PMI5, SEQ ID NO: 10) was isolated by Martinez et al. having 74.5% sequence identity to SEQ ID NO: 5 in "Genome, transcriptome, and secretome analysis of wood decay fungus *Postia placenta* supports unique mechanisms of lignocellulose conversion", 2009, *Proc. Natl. Acad. Sci. USA* 106: 1954-1959.

Wymelenberg et al. have isolated an S53 protease (UniProt: Q281W2, SEQ ID NO: 11) in "Computational analysis of the *Phanerochaete chrysosporium* v2.0 genome database and mass spectrometry identification of peptides in ligninolytic cultures reveal complex mixtures of secreted proteins", 2006, Fungal Genet. Biol. 43:343-356 having 74.1% sequence identity to SEQ ID NO: 5. Another S53 polypeptide from *Postia placenta* (UniProt:B8P431, SEQ ID NO: 12) has been identified by Martinez et al. in "Genome, transcriptome, and secretome analysis of wood decay fungus *Postia placenta* supports unique mechanisms of lignocellulose conversion", 2009, *Proc. Natl. Acad. Sci. U.S.A.* 106: 1954-1959 having 68.2% sequence identity to SEQ ID NO: 5. Other peptides, including S53 proteases, have less than 70% sequence identity to SEQ ID NO: 5.

Floudas et al. have published the sequence of an S53 protease in "The Paleozoic origin of enzymatic lignin decomposition reconstructed from 31 fungal genomes", 2012, *Science,* 336:1715-1719 having 80.6% identity to SEQ ID NO: 5. Fernandez-Fueyo et al have published the sequences of three serine proteases in "Comparative genomics of *Ceriporiopsis subvermispora* and *Phanerochaete chrysosporium* provide insight into selective ligninolysis", 2012, *Proc Natl Acad Sci USA.* 109:5458-5463 (UniProt: M2QQ01, SEQ ID NO: 26, UniProt:M2QWH2, SEQ ID NO: 27, UniProt:M2RD67, SEQ ID NO: 28) having 80.8%, 79.1% and 78.6% identity, respectively, to SEQ ID NO: 5.

WO 02/068623 describes a protease from *Aspergillus niger* with 49.2% sequence identity to SEQ ID NO: 5 for use in feed and food applications. WO 2012/048334 describes serine-type endopeptidases from *Myceliophthora thermophila* as a feed additive or for feedstuff with 47.9% sequence identity to SEQ ID NO: 5.

WO 95/28850 discloses the combination of a phytase and one or more microbial proteolytic enzymes to improve the solubility of vegetable proteins. WO 01/58275 discloses the use of acid stable proteases of the subtilisin family in animal feed. WO 01/58276 discloses the use of acid-stable proteases derived from *Nocardiopsis* sp. NRRL 18262 (the 10R protease), as well as a protease derived from *Nocardiopsis alba* DSM 14010 in animal feed. WO 2004/072221, WO 2004/111220, WO 2004/111223, WO 2005/035747, and WO 2005/123911 disclose proteases related to the 10R protease and their use in animal feed. WO 2004/072279 discloses the use of other proteases in animal feed. WO 2004/034776 discloses the use of a subtilisin/keratinase, PWD-1 from *B. licheniformis*, in the feed of poultry. WO 2004/077960 discloses a method for increasing the digestibility of forage or grain in ruminants by applying a bacterial or fungal protease.

Commercial products comprising a protease and marketed for use in animal feed include RONOZYME® ProAct (DSM NP/Novozymes), Axtra® (Danisco), Avizyme® (Danisco), Porzyme® (Danisco), Allzyme™ (Alltech), Versazyme® (BioResources, Int.), Poultrygrow™ (Jefo) and Cibenza® DP100 (Novus).

SUMMARY OF THE INVENTION

The present invention relates to isolated polypeptides having protease activity selected from the group consisting of:

(a) a polypeptide having at least 84% sequence identity to the polypeptide of SEQ ID NO: 5, SEQ ID NO: 6, or the mature polypeptide of SEQ ID NO: 2 or SEQ ID NO: 4;

(b) a polypeptide having at least 83% sequence identity to the polypeptide of SEQ ID NO: 19, or the mature polypeptide of SEQ ID NO: 16 or SEQ ID NO: 18;

(c) a polypeptide having at least 85% sequence identity to the polypeptide of SEQ ID NO: 24, or the mature polypeptide of SEQ ID NO: 21 or SEQ ID NO: 23;

(d) a polypeptide encoded by a polynucleotide that hybridizes under high stringency conditions, or very high stringency conditions with (i) the mature polypeptide coding sequence of SEQ ID NO: 1, (ii) the mature polypeptide coding sequence of SEQ ID NO: 3, (iii) the mature polypeptide coding sequence of SEQ ID NO: 15, (iv) the mature polypeptide coding sequence of SEQ ID NO: 17, (v) the mature polypeptide coding sequence of SEQ ID NO: 20, (vi) the mature polypeptide coding sequence of SEQ ID NO: 22, (vii) the full-length complementary strand of (i), (ii), (iii), (iv), (v) or (vi);

(e) a polypeptide encoded by a polynucleotide having at least 84% sequence identity to the mature polypeptide coding sequence of SEQ ID NO: 1 or SEQ ID NO: 3;

(f) a polypeptide encoded by a polynucleotide having at least 83% sequence identity to the mature polypeptide coding sequence of SEQ ID NO: 15 or SEQ ID NO: 17;

(g) a polypeptide encoded by a polynucleotide having at least 85% sequence identity to the mature polypeptide coding sequence of SEQ ID NO: 20 or SEQ ID NO: 22;

(h) a variant of the polypeptide of SEQ ID NO: 5, SEQ ID NO: 6, SEQ ID NO: 19 or SEQ ID NO: 24, or the mature polypeptide of SEQ ID NO: 2, SEQ ID NO: 4, SEQ ID NO: 16, SEQ ID NO: 18, SEQ ID NO: 21 or SEQ ID NO: 23 comprising a substitution, deletion, and/or insertion at one or more (several) positions; and (i) a fragment of a polypeptide of (a), (b), (c), (d), (e), (f), (g) or (h) having protease activity.

The present invention also relates to the use of isolated polypeptides in animal feed having protease activity selected from the group consisting of:

(a) a polypeptide having at least 60% sequence identity to the polypeptide of SEQ ID NO: 5, SEQ ID NO: 6, or the mature polypeptide of SEQ ID NO: 2 or SEQ ID NO: 4;

(b) a polypeptide having at least 60% sequence identity to the polypeptide of SEQ ID NO: 19, or the mature polypeptide of SEQ ID NO: 16 or SEQ ID NO: 18;

(c) a polypeptide having at least 60% sequence identity to the polypeptide of SEQ ID NO: 24, or the mature polypeptide of SEQ ID NO: 21 or SEQ ID NO: 23;

(d) a polypeptide encoded by a polynucleotide that hybridizes under high stringency conditions, or very high stringency conditions with (i) the mature polypeptide coding sequence of SEQ ID NO: 1, (ii) the mature polypeptide coding sequence of SEQ ID NO: 3, (iii) the mature polypeptide coding sequence of SEQ ID NO: 15, (iv) the mature polypeptide coding sequence of SEQ ID NO: 17, (v) the mature polypeptide coding sequence of SEQ ID NO: 20, (vi) the mature polypeptide coding sequence of SEQ ID NO: 22, (vii) the full-length complementary strand of (i), (ii), (iii), (iv), (v) or (vi);

(e) a polypeptide encoded by a polynucleotide having at least 60% sequence identity to the mature polypeptide coding sequence of SEQ ID NO: 1 or SEQ ID NO: 3;

(f) a polypeptide encoded by a polynucleotide having at least 60% sequence identity to the mature polypeptide coding sequence of SEQ ID NO: 15 or SEQ ID NO: 17;

(g) a polypeptide encoded by a polynucleotide having at least 60% sequence identity to the mature polypeptide coding sequence of SEQ ID NO: 20 or SEQ ID NO: 22;

(h) a variant of the polypeptide of SEQ ID NO: 5, SEQ ID NO: 6, SEQ ID NO: 19 or SEQ ID NO: 24, or the mature polypeptide of SEQ ID NO: 2, SEQ ID NO: 4, SEQ ID NO: 16, SEQ ID NO: 18, SEQ ID NO: 21 or SEQ ID NO: 23 comprising a substitution, deletion, and/or insertion at one or more (several) positions; and (i) a fragment of a polypeptide of (a), (b), (c), (d), (e), (f), (g) or (h) having protease activity.

The present invention relates to isolated polynucleotides encoding the polypeptides of the present invention, nucleic acid constructs, recombinant expression vectors, and recombinant host cells comprising the polynucleotides, and to methods of producing the polypeptides.

The present invention also relates to compositions, preferably animal feed compositions, comprising the polypeptides of the invention; use of the polypeptides of the invention in animal feed or as animal feed additives; methods for preparing a composition for use in animal feed, for improving the nutritional value of an animal feed, and methods of treating proteins to be used in animal feed compositions.

Overview of Sequence Listing

SEQ ID NO: 1 is the cDNA sequence of S53 protease 3 as isolated from *Meripilus giganteus.*

SEQ ID NO: 2 is the amino acid sequence as deduced from SEQ ID NO: 1.

SEQ ID NO: 3 is the DNA sequence of the recombinant expressed DNA sequence from SEQ ID NO: 1 with HQ-tag.

SEQ ID NO: 4 is the amino acid sequence as deduced from SEQ ID NO: 3.

SEQ ID NO: 5 is the amino acid sequence of the mature S53 protease 3 from *Meripilus giganteus.*

SEQ ID NO: 6 is the amino acid sequence of the mature S53 protease obtained from SEQ ID NO. 3.

SEQ ID NO: 7 is the DNA sequence of protease 10R (WO 2005/035747, SEQ ID NO: 1).

SEQ ID NO: 8 is the amino acid sequence of protease 10R (WO 2005/035747, SEQ ID NO: 2).

SEQ ID NO: 9 is the amino acid sequence of an S53 peptide from *Grifola frondosa* (MER078639).

SEQ ID NO: 10 is the amino acid sequence of an S53 peptide from *Postia placenta* (UniProt: B8PMI5).

SEQ ID NO: 27 is the amino acid sequence of an S53 peptide from *Ceriporiopsis subvermispora* (UniProt: M2QWH2).

SEQ ID NO: 28 is the amino acid sequence of an S53 peptide from *Ceriporiopsis subvermispora* (UniProt: M2RD67).

Identity Matrix of sequences:

| | SEQ ID: 2 | SEQ ID: 5 | SEQ ID: 9 | SEQ ID: 18 | SEQ ID: 19 | SEQ ID: 23 | SEQ ID: 24 | SEQ ID: 25 | SEQ ID: 26 | SEQ ID: 27 | SEQ ID: 28 |
|---|---|---|---|---|---|---|---|---|---|---|---|
| SEQ ID: 2 | 100 | 100 | 79.8 | 86.7 | 86.6 | 86.0 | 85.5 | 76.2 | 75.0 | 73.1 | 72.8 |
| SEQ ID: 5 | 100 | 100 | 83.6 | 86.6 | 86.6 | 85.5 | 85.5 | 80.6 | 80.8 | 79.1 | 78.6 |
| SEQ ID: 9 | 79.8 | 83.6 | 100 | 79.6 | 84.1 | 78.6 | 82.7 | 72.7 | 78.0 | 75.8 | 76.4 |
| SEQ ID: 18 | 86.7 | 86.6 | 79.6 | 100 | 100 | 96.5 | 96.2 | 77.8 | 77.0 | 75.0 | 74.8 |
| SEQ ID: 19 | 86.6 | 86.6 | 84.1 | 100 | 100 | 96.2 | 96.2 | 81.4 | 82.5 | 79.4 | 79.7 |
| SEQ ID: 23 | 86.0 | 85.5 | 78.6 | 96.5 | 96.2 | 100 | 100 | 76.8 | 77.1 | 75.0 | 74.7 |
| SEQ ID: 24 | 85.5 | 85.5 | 82.7 | 96.2 | 96.2 | 100 | 100 | 80.0 | 82.2 | 79.1 | 79.5 |
| SEQ ID: 25 | 76.2 | 80.6 | 72.7 | 77.8 | 81.4 | 76.8 | 80.0 | 100 | 70.4 | 68.9 | 69.4 |
| SEQ ID: 26 | 75.0 | 80.8 | 78.0 | 77.0 | 82.5 | 77.1 | 82.2 | 70.4 | 100 | 93.0 | 94.2 |
| SEQ ID: 27 | 73.1 | 79.1 | 75.8 | 75.0 | 79.4 | 75.0 | 79.1 | 68.9 | 93.0 | 100 | 94.4 |
| SEQ ID: 28 | 72.8 | 78.6 | 76.4 | 74.8 | 79.7 | 74.7 | 79.5 | 69.4 | 94.2 | 94.4 | 100 |

SEQ ID NO: 11 is the amino acid sequence of an S53 peptide from *Phanerochaete chrysosporium* (UniProt: Q281W2).

SEQ ID NO: 12 is the amino acid sequence of an S53 peptide from *Postia placenta* (UniProt: B8P431).

SEQ ID NO: 13 is primer 597.

SEQ ID NO: 14 is primer 598.

SEQ ID NO: 15 is the cDNA sequence of S53 protease 1 isolated from *Trametes* cf. *versicolor.*

SEQ ID NO: 16 is the amino acid sequence as deduced from SEQ ID NO: 15.

SEQ ID NO: 17 is the DNA sequence of the recombinant expressed DNA sequence from SEQ ID NO: 15.

SEQ ID NO: 18 is the amino acid sequence as deduced from SEQ ID NO: 17.

SEQ ID NO: 19 is the amino acid sequence of the mature S53 protease obtained from SEQ ID NO. 15 and SEQ ID NO: 17.

SEQ ID NO: 20 is the cDNA sequence of S53 protease 2 isolated from *Trametes versicolor.*

SEQ ID NO: 21 is the amino acid sequence as deduced from SEQ ID NO: 20.

SEQ ID NO: 22 is the DNA sequence of the recombinant expressed DNA sequence from SEQ ID NO: 20.

SEQ ID NO: 23 is the amino acid sequence as deduced from SEQ ID NO: 22.

SEQ ID NO: 24 is the amino acid sequence of the mature S53 protease obtained from SEQ ID NO. 20 and SEQ ID NO: 22.

SEQ ID NO: 25 is the amino acid sequence of an S53 peptide from Dichomitus squalens (UniProt: R7SPH9).

SEQ ID NO: 26 is the amino acid sequence of an S53 peptide from *Ceriporiopsis subvermispora* (UniProt: M2QQ01).

compared to the S53 protease 3 from *Meripilus giganteus* (SEQ ID NO: 3) (from example 2) (residual activity after 2 hours at 37° C.).

Figure 9:
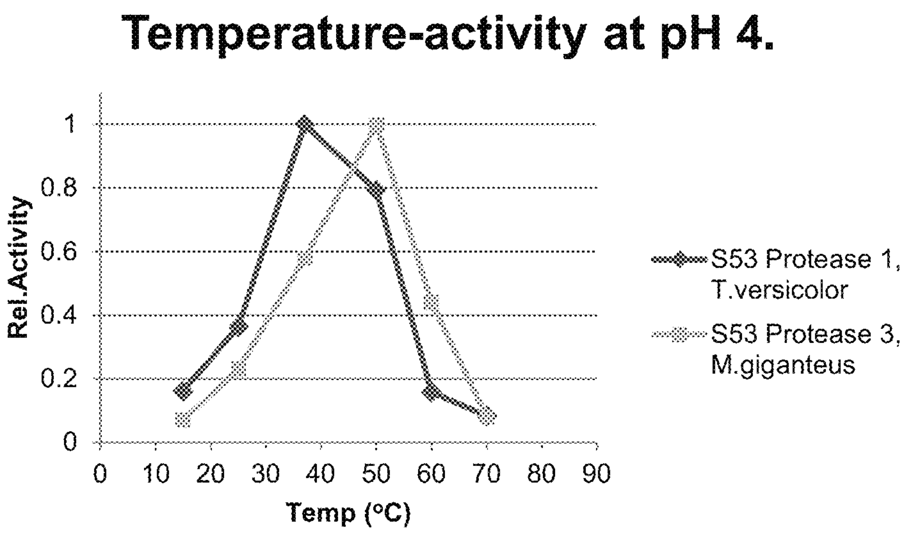

FIG. 9 shows the temperature activity profile of the S53 protease 1 isolated from *Trametes* cf. *versicolor* SEQ ID NO: 16) compared to the S53 protease 3 from *Meripilus giganteus* (SEQ ID NO: 3) (from example 2) on Protazyme AK at pH 4.

Figure 10:
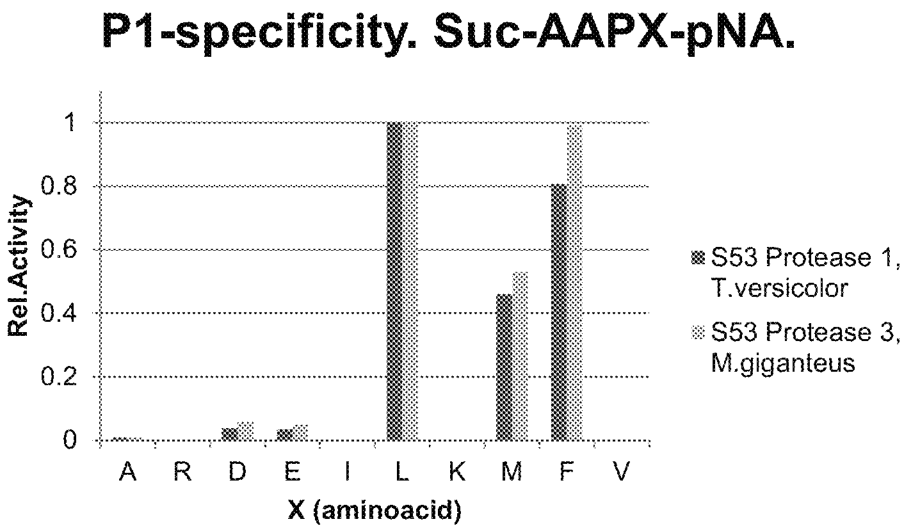

FIG. 10 shows the P1-specificity of the S53 protease 1 isolated from *Trametes* cf. *versicolor* SEQ ID NO: 16) compared to the S53 protease 3 from *Meripilus giganteus* (SEQ ID NO: 3) (from example 2) at pH 4 on 10 Suc-AAPX-pNA substrates, 25° C.

DEFINITIONS

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

cDNA: The term "cDNA" means a DNA molecule that can be prepared by reverse transcription from a mature, spliced, mRNA molecule obtained from a eukaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Coding sequence: The term "coding sequence" means a polynucleotide, which directly specifies the amino acid sequence of a polypeptide. The boundaries of the coding sequence are generally determined by an open reading frame, which usually begins with the ATG start codon or alternative start codons such as GTG and TTG and ends with a stop codon such as TAA, TAG, and TGA. The coding sequence may be a DNA, cDNA, synthetic, or recombinant polynucleotide.

Control sequences: The term "control sequences" means nucleic acid sequences necessary for expression of a polynucleotide encoding a mature polypeptide of the present invention. Each control sequence may be native (i.e., from the same gene) or foreign (i.e., from a different gene) to the polynucleotide encoding the polypeptide or native or foreign to each other.

Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

Expression: The term "expression" includes any step involved in the production of the polypeptide including, but not limited to, transcription, post-transcriptional modification, translation, post-translational modification, and secretion.

Expression vector: The term "expression vector" means a linear or circular DNA molecule that comprises a polynucleotide encoding a polypeptide and is operably linked to additional nucleotides that provide for its expression.

Fragment: The term "fragment" means a polypeptide having one or more (e.g., several) amino acids deleted from the amino and/or carboxyl terminus of a mature polypeptide; wherein the fragment has protease activity. In one aspect, a fragment contains at least 330 amino acid residues (e.g., amino acids 20 to 349 of SEQ ID NO: 2 or SEQ ID NO: 5); in another aspect, a fragment contains at least 345 amino acid residues (e.g., amino acids 10 to 354 of SEQ ID NO: 2 or SEQ ID NO: 5); in a further aspect, a fragment contains at least 355 amino acid residues (e.g., amino acids 5 to 359 of SEQ ID NO: 2 or SEQ ID NO: 5). In one aspect, a fragment contains at least 330 amino acid residues (e.g., amino acids 20 to 349 of SEQ ID NO: 16 or SEQ ID NO: 20); in another aspect, a fragment contains at least 345 amino acid residues (e.g., amino acids 10 to 354 of SEQ ID NO: 16 or SEQ ID NO: 20); in a further aspect, a fragment contains at least 355 amino acid residues (e.g., amino acids 5 to 359 of SEQ ID NO: 16 or SEQ ID NO: 20). In one aspect, a fragment contains at least 330 amino acid residues (e.g., amino acids 20 to 349 of SEQ ID NO: 21 or SEQ ID NO: 24); in another aspect, a fragment contains at least 345 amino acid residues (e.g., amino acids 10 to 354 of SEQ ID NO: 21 or SEQ ID NO: 24); in a further aspect, a fragment contains at least 355 amino acid residues (e.g., amino acids 5 to 359 of SEQ ID NO: 21 or SEQ ID NO: 24).

Host cell: The term "host cell" means any cell type that is susceptible to transformation, transfection, transduction, and the like with a nucleic acid construct or expression vector comprising a polynucleotide of the present invention. The term "host cell" encompasses any progeny of a parent cell that is not identical to the parent cell due to mutations that occur during replication.

Isolated polynucleotide: The term "isolated polynucleotide" means a polynucleotide that is in a form or environment that does not occur in nature, such as (1) any non-naturally occurring polynucleotide, (2) any polynucleotide that is at least partially removed from one or more or all of the naturally occurring constituents with which it is associated in nature; (3) any polynucleotide that is modified by the hand of man relative to that polynucleotide as found in nature or (4) any polynucleotide modified by increasing the amount of the polynucleotide relative to other components with which it is naturally associated (e.g., recombinant production in a host cell; multiple copies of a gene encoding the substance; and use of a stronger promoter than the promoter naturally associated with the gene encoding the substance). In one aspect, the isolated polynucleotide is at least 1% pure, e.g., at least 5% pure, more at least 10% pure, at least 20% pure, at least 40% pure, at least 60% pure, at least 80% pure, at least 90% pure, and at least 95% pure, as determined by agarose electrophoresis. The polynucleotides may be of genomic, cDNA, RNA, semisynthetic, synthetic origin, or any combinations thereof.

Isolated polypeptide: The term "isolated polypeptide" means a polypeptide that is in a form or environment that does not occur in nature, such as (1) any non-naturally occurring polypeptide, (2) any polypeptide that is at least partially removed from one or more or all of the naturally occurring constituents with which it is associated in nature; (3) any polypeptide that is modified by the hand of man relative to that polypeptide as found in nature in admixture with other components, such as other polypeptides, secondary metabolites, salts, et alia or (4) any polypeptide modified by increasing the amount of the polypeptide relative to other components with which it is naturally associated. In one aspect, the polypeptide is at least 1% pure, e.g., at least 5% pure, at least 10% pure, at least 20% pure, at least 40% pure, at least 60% pure, at least 80% pure, and at least 90% pure, as determined by SDS-PAGE.

Mature polypeptide: The term "mature polypeptide" means a polypeptide in its final form following translation and any post-translational modifications, such as N-terminal processing, C-terminal truncation, glycosylation, phosphorylation, etc. In one aspect, the mature polypeptide is amino acids 1 to 366 in the numbering of SEQ ID NO: 2 based on sequencing using Edman degradation and intact molecular weight analysis of the mature polypeptide with C-terminal HQ-tag. Using the prediction program SignalP (Nielsen et al., 1997, *Protein Engineering* 10: 1-6), amino acids −198 to −182 in the numbering of SEQ ID NO: 2 are predicted to be the signal peptide.

In another aspect, the mature polypeptide is amino acids 1 to 366 in the numbering of SEQ ID NO: 17 based on sequencing using Edman degradation and intact molecular weight analysis of the mature polypeptide. Using the prediction program SignalP (Nielsen et al., 1997, *Protein Engineering* 10: 1-6), amino acids −199 to −183 in the numbering of SEQ ID NO: 17 are predicted to be the signal peptide.

In a further aspect, the mature polypeptide in the numbering of SEQ ID NO: 23 is predicted to be amino acids 1 to 366 and the signal peptide is predicted to be amino acids −199 to −183 based on the prediction program SignalP (Nielsen et al., 1997, *Protein Engineering* 10: 1-6). It is known in the art that a host cell may produce a mixture of two of more different mature polypeptides (i.e., with a different C-terminal and/or N-terminal amino acid) expressed by the same polynucleotide.

Mature polypeptide coding sequence: The term "mature polypeptide coding sequence" means a polynucleotide that encodes a mature polypeptide having protease activity. In one aspect, the mature polypeptide coding sequence is nucleotides 605 to 1702 in the numbering of SEQ ID NO: 1 based on the determination of the mature polypeptide by Edman degradation and intact molecular weight analysis of the mature polypeptide with C-terminal HQ-tag. Furthermore, nucleotides 11 to 61 in the numbering of SEQ ID NO: 1 are predicted to encode a signal peptide based on the prediction program SignalP (Nielsen et al., 1997, *Protein Engineering* 10: 1-6).

In another aspect, the mature polypeptide coding sequence is the joined sequence of nucleotides 707 to 853, nucleotides 912 to 1022, nucleotides 1077 to 1276, nucleotides 1332 to 1469, nucleotides 1531 to 1978 and nucleotides 2031 to 2084 of SEQ ID NO: 15 or the cDNA sequence thereof based on the determination of the mature polypeptide by Edman degradation and intact molecular weight analysis of the mature polypeptide. Nucleotides 1 to 51 in the numbering of SEQ ID NO: 15 are predicted to encode a signal peptide based on the prediction program SignalP (Nielsen et al., 1997, *Protein Engineering* 10: 1-6). In a further aspect, the mature polypeptide coding sequence is nucleotides 598 to 1695 of SEQ ID NO: 17 or the cDNA sequence thereof based on the determination of the mature polypeptide by Edman degradation and intact molecular weight analysis of the mature polypeptide. Nucleotides 1 to 51 in the numbering of SEQ ID NO: 22 are predicted to encode a signal peptide based on the prediction program SignalP (Nielsen et al., 1997, *Protein Engineering* 10: 1-6).

In another aspect, the mature polypeptide coding sequence is predicted to be the joined sequence of nucleotides 706 to 852, nucleotides 914 to 1024, nucleotides 1080 to 1279, nucleotides 1333 to 1470, nucleotides 1532 to 1979 and nucleotides 2032 to 2085 of SEQ ID NO: 20 or the cDNA sequence thereof based on the SignalP program (Nielsen et al., 1997, supra) that predicts nucleotides 1 to 51 of SEQ ID NO: 20 encode a signal peptide. In another aspect, the mature polypeptide coding sequence is predicted to be nucleotides 598 to 1695 of SEQ ID NO: 22 or the cDNA sequence thereof based on the SignalP program (Nielsen et al., 1997, supra) that predicts nucleotides 1 to 51 of SEQ ID NO: 22 encode a signal peptide.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic. The term nucleic acid construct is synonymous with the term "expression cassette" when the nucleic acid construct contains the control sequences required for expression of a coding sequence of the present invention.

Operably linked: The term "operably linked" means a configuration in which a control sequence is placed at an appropriate position relative to the coding sequence of a polynucleotide such that the control sequence directs the expression of the coding sequence.

Protease activity: The term "protease activity" means proteolytic activity (EC 3.4). There are several protease activity types such as trypsin-like proteases cleaving at the carboxy-terminal side of Arg and Lys residues and chymotrypsin-like proteases cleaving at the carboxy-terminal side of hydrophobic amino acid residues. Proteases of the invention are serine endopeptidases (EC 3.4.21) with acidic pH-optimum (pH optimum <pH 7).

Protease activity can be measured using any assay, in which a substrate is employed, that includes peptide bonds relevant for the specificity of the protease in question. Assay-pH and assay-temperature are likewise to be adapted to the protease in question. Examples of assay-pH-values are pH 2, 3, 4, 5, 6, 7, 8, 9, 10, 11, or 12. Examples of assay-temperatures are 15, 20, 25, 30, 35, 37, 40, 45, 50, 55, 60, 65, 70, 80, 90, or 95° C. Examples of general protease substrates are casein, bovine serum albumin and haemoglobin. In the classical Anson and Mirsky method, denatured haemoglobin is used as substrate and after the assay incubation with the protease in question, the amount of trichloroacetic acid soluble haemoglobin is determined as a measurement of protease activity (Anson and Mirsky, 1932, *J. Gen. Physiol.* 16: 59 and Anson, 1938, *J. Gen. Physiol.* 22: 79).

For the purpose of the present invention, protease activity was determined using assays which are described in "Materials and Methods", such as the Kinetic Suc-AAPF-pNA assay, Protazyme AK assay, Kinetic Suc-AAPX-pNA assay and o-Phthaldialdehyde (OPA). For the Protazyme AK assay, insoluble Protazyme AK (Azurine-Crosslinked Casein) substrate liberates a blue colour when incubated with the protease and the colour is determined as a measurement of protease activity. For the Suc-AAPF-pNA assay, the colorless Suc-AAPF-pNA substrate liberates yellow paranitroaniline when incubated with the protease and the yellow color is determined as a measurement of protease activity.

The polypeptides of the present invention have at least 20%, e.g., at least 40%, at least 50%, at least 60%, at least 70%, at least 80%, at least 90%, at least 95%, and at least 100% of the protease activity of the polypeptide of SEQ ID NO: 6, SEQ ID NO: 19 and/or SEQ D NO: 24.

Sequence Identity: The relatedness between two amino acid sequences or between two nucleotide sequences is described by the parameter "sequence identity".

For purposes of the present invention, the degree of sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 3.0.0 or later. Version 6.1.0 was used. The optional parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

(Identical Residues×100)/(Length of Alignment−Total Number of Gaps in Alignment)

For purposes of the present invention, the degree of sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 3.0.0 or later. Version 6.1.0 was used. The optional parameters used are gap open penalty of 10, gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows:

(Identical Deoxyribonucleotides×100)/(Length of Alignment−Total Number of Gaps in Alignment)

Stringency conditions: The different strigency conditions are defined as follows.

The term "very low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 45° C.

The term "low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 50° C.

The term "medium stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 55° C.

The term "medium-high stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 60° C.

The term "high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 65° C.

The term "very high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 70° C.

Subsequence: The term "subsequence" means a polynucleotide having one or more (several) nucleotides deleted from the 5' and/or 3' end of a mature polypeptide coding sequence; wherein the subsequence encodes a fragment having protease activity. In one aspect, a subsequence contains at least 990 nucleotides (e.g., nucleotides 662 to 1651 of SEQ ID NO: 1), e.g., at least 1035 nucleotides (e.g., nucleotides 632 to 1666 of SEQ ID NO: 1); e.g., at least 1065 nucleotides (e.g., nucleotides 617 to 1681 of SEQ ID NO: 1).

Substantially pure polynucleotide: The term "substantially pure polynucleotide" means a polynucleotide preparation free of other extraneous or unwanted nucleotides and in a form suitable for use within genetically engineered polypeptide production systems. Thus, a substantially pure polynucleotide contains at most 10%, at most 8%, at most 6%, at most 5%, at most 4%, at most 3%, at most 2%, at most 1%, and at most 0.5% by weight of other polynucleotide material with which it is natively or recombinantly associated. A substantially pure polynucleotide may, however, include naturally occurring 5' and 3' untranslated regions, such as promoters and terminators. Preferably, the polynucleotide is at least 90% pure, e.g., at least 92% pure, at least 94% pure, at least 95% pure, at least 96% pure, at least 97% pure, at least 98% pure, at least 99% pure, and at least 99.5% pure or 100% pure by weight. The polynucleotides of the present invention are preferably in a substantially pure form.

Substantially pure polypeptide: The term "substantially pure polypeptide" means a preparation that contains at most 10%, at most 8%, at most 6%, at most 5%, at most 4%, at most 3%, at most 2%, at most 1%, and at most 0.5% by weight of other polypeptide material with which it is natively or recombinantly associated. Preferably, the polypeptide is at least 92% pure, e.g., at least 94% pure, at least 95% pure, at least 96% pure, at least 97% pure, at least 98% pure, at least 99%, at least 99.5% pure, and 100% pure by weight of the total polypeptide material present in the preparation. The polypeptides of the present invention are preferably in a substantially pure form. This can be accomplished, for example, by preparing the polypeptide by well-known recombinant methods or by classical purification methods.

Variant: The term "variant" means a polypeptide having protease activity comprising an alteration, i.e., a substitution, insertion, and/or deletion of one or more (several) amino acid residues at one or more (several) positions. A substitution means a replacement of an amino acid occupying a position with a different amino acid; a deletion means removal of an amino acid occupying a position; and an insertion means adding 1-3 amino acids adjacent to an amino acid occupying a position. The variants of the present invention have at least 20%, e.g., at least 40%, at least 50%, at least 60%, at least 70%, at least 80%, at least 90%, at least 95%, or at least 100% of the protease activity of the polypeptide of SEQ ID NO: 5, SEQ ID NO: 6, or the mature polypeptide of SEQ ID NO: 2 or SEQ ID NO: 4.

DETAILED DESCRIPTION OF THE INVENTION

Polypeptides Having Protease Activity

Polypeptides having protease activity, or proteases, are sometimes also designated peptidases, proteinases, peptide hydrolases, or proteolytic enzymes. Proteases may be of the exo-type that hydrolyse peptides starting at either end thereof, or of the endo-type that act internally in polypeptide chains (endopeptidases). Endopeptidases show activity on N- and C-terminally blocked peptide substrates that are relevant for the specificity of the protease in question.

The term "protease" is defined herein as an enzyme that hydrolyses peptide bonds. This definition of protease also applies to the protease-part of the terms "parent protease" and "protease variant," as used herein. The term "protease" includes any enzyme belonging to the EC 3.4 enzyme group (including each of the eighteen subclasses thereof). The EC number refers to Enzyme Nomenclature 1992 from NC-IUBMB, Academic Press, San Diego, Calif., including supplements 1-5 published in 1994, *Eur. J. Biochem.* 223: 1-5; 1995, *Eur. J. Biochem.* 232: 1-6; 1996, *Eur. J. Biochem.* 237: 1-5; 1997, *Eur. J. Biochem.* 250: 1-6; and 1999, *Eur. J. Biochem.* 264: 610-650 respectively. The nomenclature is regularly supplemented and updated; see, e.g., the World Wide Web (WWW) at chem.qmw.ac.uk/iubmb/enzyme/index.html.

The proteases of the invention and for use according to the invention are selected from the group consisting of:

(a) proteases belonging to the EC 3.4.21. enzyme group; and/or (b) proteases belonging to the EC 3.4.14. enzyme group; and/or (c) Serine proteases of the peptidase family S53 that comprises two different types of peptidases: tripeptidyl aminopeptidases (exo-type) and endo-peptidases; as described in 1993, *Biochem. J.* 290:205-218 and in MEROPS protease database, release 9.4 (31 Jan. 2011) (merops.ac.uk). The database is described in Rawlings et al., 2010, "MEROPS: the peptidase database", *Nucl. Acids Res.* 38: D227-D233.

For determining whether a given protease is a Serine protease, and a family S53 protease, reference is made to the above Handbook and the principles indicated therein. Such determination can be carried out for all types of proteases, be it naturally occurring or wild-type proteases; or genetically engineered or synthetic proteases.

Peptidase family S53 contains acid-acting endopeptidases and tripeptidyl-peptidases. The residues of the catalytic triad are Glu, Asp, Ser, and there is an additional acidic residue, Asp, in the oxyanion hole. The order of the residues is Glu, Asp, Asp, Ser. The Ser residue is the nucleophile equivalent to Ser in the Asp, His, Ser triad of subtilisin, and the Glu of the triad is a substitute for the general base, His, in subtilisin.

Mutation of any of the amino acids of the catalytic triad or oxyanion hole will result in a change or loss of enzyme activity. The amino acids of the catalytic triad and oxyanion hole of the S53 protease 3 from *Meripilus giganteus* (SEQ ID NO: 5) are probably positions Glu-85, Asp-89, Asp-175 and Ser-283. The amino acids of the catalytic triad and oxyanion hole of the S53 protease 1 from *Trametes versicolor* (SEQ ID NO: 19) are probably positions Glu-85, Asp-89, Asp-175 and Ser-283. The amino acids of the catalytic triad and oxyanion hole of the S53 protease 2 from *Trametes versicolor* (SEQ ID NO: 24) are probably positions Glu-85, Asp-89, Asp-175 and Ser-283.

The peptidases of the S53 family tend to be most active at acidic pH (unlike the homologous subtilisins), and this can be attributed to the functional importance of carboxylic residues, notably Asp in the oxyanion hole. The amino acid sequences are not closely similar to those in family S8 (i.e., serine endopeptidase subtilisins and homologues), and this, taken together with the quite different active site residues and the resulting lower pH for maximal activity, provides for a substantial difference to that family. Protein folding of the peptidase unit for members of this family resembles that of subtilisin, having the clan type SB.

A new S53 protease from *Meripilus giganteus* with high activity at low pH (3-4) on soybean-maize meal was identified and cloned in relation to the present invention. For determining whether a given protease is a Serine protease, and a family S53 protease, reference is made to the above Handbook and the principles indicated therein. Such determination can be carried out for all types of proteases, be it naturally occurring or wild-type proteases; or genetically engineered or synthetic proteases.

The present invention provides polypeptides having protease activity and polynucleotides encoding the polypeptides. The proteases of the invention are serine proteases of the peptidase family S53. The proteases of the invention exhibit pH properties, especially pH stability properties, which make them of substantial interest as candidates for use in animal feed, and other applications.

The proteases of the invention are acidic proteases with a preference for hydrophibic amino acid residues such as Leu, Tyr, Phe and Met in the P1 position. The proteases have high activity on Suc-Ala-Ala-Pro-Leu-pNA and Suc-Ala-Ala-Pro-Phe-pNA with a broad pH range from 2-5 and retain more than 95% activity after being subjected for 2 hours to pH as low as 3.

The present invention relates to isolated polypeptides having protease activity selected from the group consisting of:

(a) a polypeptide having at least 84% sequence identity to the polypeptide of SEQ ID NO: 5, SEQ ID NO: 6, or the mature polypeptide of SEQ ID NO: 2 or SEQ ID NO: 4;

(b) a polypeptide having at least 83% sequence identity to the polypeptide of SEQ ID NO: 19, or the mature polypeptide of SEQ ID NO: 16 or SEQ ID NO: 18;

(c) a polypeptide having at least 85% sequence identity to the polypeptide of SEQ ID NO: 24, or the mature polypeptide of SEQ ID NO: 21 or SEQ ID NO: 23;

(d) a polypeptide encoded by a polynucleotide that hybridizes under high stringency conditions, or very high stringency conditions with (i) the mature polypeptide coding sequence of SEQ ID NO: 1, (ii) the mature polypeptide coding sequence of SEQ ID NO: 3, (iii) the mature polypeptide coding sequence of SEQ ID NO: 15, (iv) the mature polypeptide coding sequence of SEQ ID NO: 17, (v) the mature polypeptide coding sequence of SEQ ID NO: 20, (vi) the mature polypeptide coding sequence of SEQ ID NO: 22, (vii) the full-length complementary strand of (i), (ii), (iii), (iv), (v) or (vi);

(e) a polypeptide encoded by a polynucleotide having at least 84% sequence identity to the mature polypeptide coding sequence of SEQ ID NO: 1 or SEQ ID NO: 3;

(f) a polypeptide encoded by a polynucleotide having at least 83% sequence identity to the mature polypeptide coding sequence of SEQ ID NO: 15 or SEQ ID NO: 17;

(g) a polypeptide encoded by a polynucleotide having at least 85% sequence identity to the mature polypeptide coding sequence of SEQ ID NO: 20 or SEQ ID NO: 22;

(h) a variant of the polypeptide of SEQ ID NO: 5, SEQ ID NO: 6, SEQ ID NO: 19 or SEQ ID NO: 24, or the mature polypeptide of SEQ ID NO: 2, SEQ ID NO: 4, SEQ ID NO: 16, SEQ ID NO: 18, SEQ ID NO: 21 or SEQ ID NO: 23 comprising a substitution, deletion, and/or insertion at one or more (several) positions; and (i) a fragment of a polypeptide of (a), (b), (c), (d), (e), (f), (g) or (h) having protease activity.

An embodiment of the invention is a polypeptide having at least 85% sequence identity to the polypeptide of SEQ ID NO: 5, SEQ ID NO: 6, or the mature polypeptide of SEQ ID NO: 2 or SEQ ID NO: 4.

An embodiment of the invention is a polypeptide having at least 86% sequence identity to the polypeptide of SEQ ID NO: 5, SEQ ID NO: 6, or the mature polypeptide of SEQ ID NO: 2 or SEQ ID NO: 4.

An embodiment of the invention is a polypeptide having at least 87% sequence identity to the polypeptide of SEQ ID NO: 5, SEQ ID NO: 6, or the mature polypeptide of SEQ ID NO: 2 or SEQ ID NO: 4.

An embodiment of the invention is a polypeptide having at least 88% sequence identity to the polypeptide of SEQ ID NO: 5, SEQ ID NO: 6, or the mature polypeptide of SEQ ID NO: 2 or SEQ ID NO: 4.

An embodiment of the invention is a polypeptide having at least 89% sequence identity to the polypeptide of SEQ ID NO: 5, SEQ ID NO: 6, or the mature polypeptide of SEQ ID NO: 2 or SEQ ID NO: 4.

An embodiment of the invention is a polypeptide having at least 90% sequence identity to the polypeptide of SEQ ID NO: 5, SEQ ID NO: 6, or the mature polypeptide of SEQ ID NO: 2 or SEQ ID NO: 4.

An embodiment of the invention is a polypeptide having at least 91% sequence identity to the polypeptide of SEQ ID NO: 5, SEQ ID NO: 6, or the mature polypeptide of SEQ ID NO: 2 or SEQ ID NO: 4.

An embodiment of the invention is a polypeptide having at least 92% sequence identity to the polypeptide of SEQ ID NO: 5, SEQ ID NO: 6, or the mature polypeptide of SEQ ID NO: 2 or SEQ ID NO: 4.

An embodiment of the invention is a polypeptide having at least 93% sequence identity to the polypeptide of SEQ ID NO: 5, SEQ ID NO: 6, or the mature polypeptide of SEQ ID NO: 2 or SEQ ID NO: 4.

An embodiment of the invention is a polypeptide having at least 94% sequence identity to the polypeptide of SEQ ID NO: 5, SEQ ID NO: 6, or the mature polypeptide of SEQ ID NO: 2 or SEQ ID NO: 4.

An embodiment of the invention is a polypeptide having at least 95% sequence identity to the polypeptide of SEQ ID NO: 5, SEQ ID NO: 6, or the mature polypeptide of SEQ ID NO: 2 or SEQ ID NO: 4.

An embodiment of the invention is a polypeptide having at least 96% sequence identity to the polypeptide of SEQ ID NO: 5, SEQ ID NO: 6, or the mature polypeptide of SEQ ID NO: 2 or SEQ ID NO: 4.

An embodiment of the invention is a polypeptide having at least 97% sequence identity to the polypeptide of SEQ ID NO: 5, SEQ ID NO: 6, or the mature polypeptide of SEQ ID NO: 2 or SEQ ID NO: 4.

An embodiment of the invention is a polypeptide having at least 98% sequence identity to the polypeptide of SEQ ID NO: 5, SEQ ID NO: 6, or the mature polypeptide of SEQ ID NO: 2 or SEQ ID NO: 4.

An embodiment of the invention is a polypeptide having at least 99% sequence identity to the polypeptide of SEQ ID NO: 5, SEQ ID NO: 6, or the mature polypeptide of SEQ ID NO: 2 or SEQ ID NO: 4.

An embodiment of the invention is a polypeptide having 100% sequence identity to the polypeptide of SEQ ID NO: 5, SEQ ID NO: 6, or the mature polypeptide of SEQ ID NO: 2 or SEQ ID NO: 4.

The present invention relates to isolated polypeptides having a sequence identity to the polypeptide of SEQ ID NO: 5, SEQ ID NO: 6, or the mature polypeptide of SEQ ID NO: 2 or SEQ ID NO: 4 of at least 84%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, which have protease activity. In one aspect, the polypeptides differ by no more than thirty amino acids, e.g., by twenty five amino acids, by twenty amino acids, by fifteen amino acids, by twelve amino acids, by ten amino acids, by nine amino acids, by eight amino acids, by seven amino acids, by six amino acids, by five amino acids, by four amino acids, by three amino acids, by two amino acids, and by one amino acid from the polypeptide of SEQ ID NO: 5, SEQ ID NO: 6, or the mature polypeptide of SEQ ID NO: 2 or SEQ ID NO: 4.

An embodiment of the invention is a polypeptide having at least 84% sequence identity to the polypeptide of SEQ ID NO: 19, or the mature polypeptide of SEQ ID NO: 16 or SEQ ID NO: 18.

An embodiment of the invention is a polypeptide having at least 85% sequence identity to the polypeptide of SEQ ID NO: 19, or the mature polypeptide of SEQ ID NO: 16 or SEQ ID NO: 18.

An embodiment of the invention is a polypeptide having at least 86% sequence identity to the polypeptide of SEQ ID NO: 19, or the mature polypeptide of SEQ ID NO: 16 or SEQ ID NO: 18.

An embodiment of the invention is a polypeptide having at least 87% sequence identity to the polypeptide of SEQ ID NO: 19, or the mature polypeptide of SEQ ID NO: 16 or SEQ ID NO: 18.

An embodiment of the invention is a polypeptide having at least 88% sequence identity to the polypeptide of SEQ ID NO: 19, or the mature polypeptide of SEQ ID NO: 16 or SEQ ID NO: 18.

An embodiment of the invention is a polypeptide having at least 89% sequence identity to the polypeptide of SEQ ID NO: 19, or the mature polypeptide of SEQ ID NO: 16 or SEQ ID NO: 18.

An embodiment of the invention is a polypeptide having at least 90% sequence identity to the polypeptide of SEQ ID NO: 19, or the mature polypeptide of SEQ ID NO: 16 or SEQ ID NO: 18.

An embodiment of the invention is a polypeptide having at least 91% sequence identity to the polypeptide of SEQ ID NO: 19, or the mature polypeptide of SEQ ID NO: 16 or SEQ ID NO: 18.

An embodiment of the invention is a polypeptide having at least 92% sequence identity to the polypeptide of SEQ ID NO: 19, or the mature polypeptide of SEQ ID NO: 16 or SEQ ID NO: 18.

An embodiment of the invention is a polypeptide having at least 93% sequence identity to the polypeptide of SEQ ID NO: 19, or the mature polypeptide of SEQ ID NO: 16 or SEQ ID NO: 18.

An embodiment of the invention is a polypeptide having at least 94% sequence identity to the polypeptide of SEQ ID NO: 19, or the mature polypeptide of SEQ ID NO: 16 or SEQ ID NO: 18.

An embodiment of the invention is a polypeptide having at least 95% sequence identity to the polypeptide of SEQ ID NO: 19, or the mature polypeptide of SEQ ID NO: 16 or SEQ ID NO: 18.

An embodiment of the invention is a polypeptide having at least 96% sequence identity to the polypeptide of SEQ ID NO: 19, or the mature polypeptide of SEQ ID NO: 16 or SEQ ID NO: 18.

An embodiment of the invention is a polypeptide having at least 97% sequence identity to the polypeptide of SEQ ID NO: 19, or the mature polypeptide of SEQ ID NO: 16 or SEQ ID NO: 18.

An embodiment of the invention is a polypeptide having at least 98% sequence identity to the polypeptide of SEQ ID NO: 19, or the mature polypeptide of SEQ ID NO: 16 or SEQ ID NO: 18.

An embodiment of the invention is a polypeptide having at least 99% sequence identity to the polypeptide of SEQ ID NO: 19, or the mature polypeptide of SEQ ID NO: 16 or SEQ ID NO: 18.

An embodiment of the invention is a polypeptide having 100% sequence identity to the polypeptide of SEQ ID NO: 19, or the mature polypeptide of SEQ ID NO: 16 or SEQ ID NO: 18.

The present invention relates to isolated polypeptides having a sequence identity to the polypeptide of SEQ ID NO: 19, or the mature polypeptide of SEQ ID NO: 16 or SEQ ID NO: 18 of at least 83%, e.g., at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, which have protease activity. In one aspect, the polypeptides differ by no more than thirty amino acids, e.g., by twenty five amino acids, by twenty amino acids, by fifteen amino acids, by twelve amino acids, by ten amino acids, by nine amino acids, by eight amino acids, by seven amino acids, by six amino acids, by five amino acids, by four amino acids, by three amino acids, by two amino acids, and by one amino acid from the polypeptide of SEQ ID NO: 19, or the mature polypeptide of SEQ ID NO: 16 or SEQ ID NO: 18.

An embodiment of the invention is a polypeptide having at least 86% sequence identity to the polypeptide of SEQ ID NO: 24, or the mature polypeptide of SEQ ID NO: 21 or SEQ ID NO: 23.

An embodiment of the invention is a polypeptide having at least 87% sequence identity to the polypeptide of SEQ ID NO: 24, or the mature polypeptide of SEQ ID NO: 21 or SEQ ID NO: 23.

An embodiment of the invention is a polypeptide having at least 88% sequence identity to the polypeptide of SEQ ID NO: 24, or the mature polypeptide of SEQ ID NO: 21 or SEQ ID NO: 23.

An embodiment of the invention is a polypeptide having at least 89% sequence identity to the polypeptide of SEQ ID NO: 24, or the mature polypeptide of SEQ ID NO: 21 or SEQ ID NO: 23.

An embodiment of the invention is a polypeptide having at least 90% sequence identity to the polypeptide of SEQ ID NO: 24, or the mature polypeptide of SEQ ID NO: 21 or SEQ ID NO: 23.

An embodiment of the invention is a polypeptide having at least 91% sequence identity to the polypeptide of SEQ ID NO: 24, or the mature polypeptide of SEQ ID NO: 21 or SEQ ID NO: 23.

An embodiment of the invention is a polypeptide having at least 92% sequence identity to the polypeptide of SEQ ID NO: 24, or the mature polypeptide of SEQ ID NO: 21 or SEQ ID NO: 23.

An embodiment of the invention is a polypeptide having at least 93% sequence identity to the polypeptide of SEQ ID NO: 24, or the mature polypeptide of SEQ ID NO: 21 or SEQ ID NO: 23.

An embodiment of the invention is a polypeptide having at least 94% sequence identity to the polypeptide of SEQ ID NO: 24, or the mature polypeptide of SEQ ID NO: 21 or SEQ ID NO: 23.

An embodiment of the invention is a polypeptide having at least 95% sequence identity to the polypeptide of SEQ ID NO: 24, or the mature polypeptide of SEQ ID NO: 21 or SEQ ID NO: 23.

An embodiment of the invention is a polypeptide having at least 96% sequence identity to the polypeptide of SEQ ID NO: 24, or the mature polypeptide of SEQ ID NO: 21 or SEQ ID NO: 23.

An embodiment of the invention is a polypeptide having at least 97% sequence identity to the polypeptide of SEQ ID NO: 24, or the mature polypeptide of SEQ ID NO: 21 or SEQ ID NO: 23.

An embodiment of the invention is a polypeptide having at least 98% sequence identity to the polypeptide of SEQ ID NO: 24, or the mature polypeptide of SEQ ID NO: 21 or SEQ ID NO: 23.

An embodiment of the invention is a polypeptide having at least 99% sequence identity to the polypeptide of SEQ ID NO: 24, or the mature polypeptide of SEQ ID NO: 21 or SEQ ID NO: 23.

An embodiment of the invention is a polypeptide having 100% sequence identity to the polypeptide of SEQ ID NO: 24, or the mature polypeptide of SEQ ID NO: 21 or SEQ ID NO: 23.

The present invention relates to isolated polypeptides having a sequence identity to the polypeptide of SEQ ID NO: 24, or the mature polypeptide of SEQ ID NO: 21 or SEQ ID NO: 23 of at least 85%, e.g., at least 86%, at least 87%, at least 88%, at least 89%, at least 90%, at least 91%, at least 92%, at least 93%, at least 94%, at least 95%, at least 96%, at least 97%, at least 98%, at least 99%, or 100%, which have protease activity. In one aspect, the polypeptides differ by no more than thirty amino acids, e.g., by twenty five amino acids, by twenty amino acids, by fifteen amino acids, by twelve amino acids, by ten amino acids, by nine amino acids, by eight amino acids, by seven amino acids, by six amino acids, by five amino acids, by four amino acids, by three amino acids, by two amino acids, and by one amino acid from the polypeptide of SEQ ID NO: 24, or the mature polypeptide of SEQ ID NO: 21 or SEQ ID NO: 23.

The present invention also relates to the use of isolated polypeptides in animal feed having protease activity selected from the group consisting of:

(a) a polypeptide having at least 60% sequence identity to the polypeptide of SEQ ID NO: 5, SEQ ID NO: 6, or the mature polypeptide of SEQ ID NO: 2 or SEQ ID NO: 4;

(b) a polypeptide having at least 60% sequence identity to the polypeptide of SEQ ID NO: 19, or the mature polypeptide of SEQ ID NO: 16 or SEQ ID NO: 18;

(c) a polypeptide having at least 60% sequence identity to the polypeptide of SEQ ID NO: 24, or the mature polypeptide of SEQ ID NO: 21 or SEQ ID NO: 23;

(d) a polypeptide encoded by a polynucleotide that hybridizes under medium stringency conditions, medium-high stringency conditions, high stringency conditions, or very high stringency conditions with (i) the mature polypeptide coding sequence of SEQ ID NO: 1, (ii) the mature polypeptide coding sequence of SEQ ID NO: 3, (iii) the mature polypeptide coding sequence of SEQ ID NO: 15, (iv) the mature polypeptide coding sequence of SEQ ID NO: 17, (v) the mature polypeptide coding sequence of SEQ ID NO: 20, (vi) the mature polypeptide coding sequence of SEQ ID NO: 22, (vii) the full-length complementary strand of (i), (ii), (iii), (iv), (v) or (vi);

(e) a polypeptide encoded by a polynucleotide having at least 60% sequence identity to the mature polypeptide coding sequence of SEQ ID NO: 1 or SEQ ID NO: 3;

(f) a polypeptide encoded by a polynucleotide having at least 60% sequence identity to the mature polypeptide coding sequence of SEQ ID NO: 15 or SEQ ID NO: 17;

(g) a polypeptide encoded by a polynucleotide having at least 60% sequence identity to the mature polypeptide coding sequence of SEQ ID NO: 20 or SEQ ID NO: 22;

(h) a variant of the polypeptide of SEQ ID NO: 5, SEQ ID NO: 6, SEQ ID NO: 19 or SEQ ID NO: 24, or the mature polypeptide of SEQ ID NO: 2, SEQ ID NO: 4, SEQ ID NO: 16, SEQ ID NO: 18, SEQ ID NO: 21 or SEQ ID NO: 23 comprising a substitution, deletion, and/or insertion at one or more (several) positions; and (i) a fragment of a polypeptide of (a), (b), (c), (d), (e), (f), (g) or (h) having protease activity.

An embodiment of the invention is a polypeptide for use in animal feed having at least 70% sequence identity to the polypeptide of SEQ ID NO: 5, SEQ ID NO: 6, or the mature polypeptide of SEQ ID NO: 2 or SEQ ID NO: 4.

An embodiment of the invention is a polypeptide for use in animal feed having at least 75% sequence identity to the polypeptide of SEQ ID NO: 5, SEQ ID NO: 6, or the mature polypeptide of SEQ ID NO: 2 or SEQ ID NO: 4.

An embodiment of the invention is a polypeptide for use in animal feed having at least 80% sequence identity to the polypeptide of SEQ ID NO: 5, SEQ ID NO: 6, or the mature polypeptide of SEQ ID NO: 2 or SEQ ID NO: 4.

An embodiment of the invention is a polypeptide for use in animal feed having at least 85% sequence identity to the polypeptide of SEQ ID NO: 5, SEQ ID NO: 6, or the mature polypeptide of SEQ ID NO: 2 or SEQ ID NO: 4.

An embodiment of the invention is a polypeptide for use in animal feed having at least 87% sequence identity to the polypeptide of SEQ ID NO: 5, SEQ ID NO: 6, or the mature polypeptide of SEQ ID NO: 2 or SEQ ID NO: 4.

An embodiment of the invention is a polypeptide for use in animal feed having at least 90% sequence identity to the polypeptide of SEQ ID NO: 5, SEQ ID NO: 6, or the mature polypeptide of SEQ ID NO: 2 or SEQ ID NO: 4.

An embodiment of the invention is a polypeptide for use in animal feed having at least 91% sequence identity to the polypeptide of SEQ ID NO: 5, SEQ ID NO: 6, or the mature polypeptide of SEQ ID NO: 2 or SEQ ID NO: 4.

An embodiment of the invention is a polypeptide for use in animal feed having at least 92% sequence identity to the polypeptide of SEQ ID NO: 5, SEQ ID NO: 6, or the mature polypeptide of SEQ ID NO: 2 or SEQ ID NO: 4.

An embodiment of the invention is a polypeptide for use in animal feed having at least 93% sequence identity to the polypeptide of SEQ ID NO: 5, SEQ ID NO: 6, or the mature polypeptide of SEQ ID NO: 2 or SEQ ID NO: 4.

An embodiment of the invention is a polypeptide for use in animal feed having at least 94% sequence identity to the polypeptide of SEQ ID NO: 5, SEQ ID NO: 6, or the mature polypeptide of SEQ ID NO: 2 or SEQ ID NO: 4.

An embodiment of the invention is a polypeptide for use in animal feed having at least 95% sequence identity to the polypeptide of SEQ ID NO: 5, SEQ ID NO: 6, or the mature polypeptide of SEQ ID NO: 2 or SEQ ID NO: 4.

An embodiment of the invention is a polypeptide for use in animal feed having at least 96% sequence identity to the polypeptide of SEQ ID NO: 5, SEQ ID NO: 6, or the mature polypeptide of SEQ ID NO: 2 or SEQ ID NO: 4.

An embodiment of the invention is a polypeptide for use in animal feed having at least 97% sequence identity to the polypeptide of SEQ ID NO: 5, SEQ ID NO: 6, or the mature polypeptide of SEQ ID NO: 2 or SEQ ID NO: 4.

An embodiment of the invention is a polypeptide for use in animal feed having at least 98% sequence identity to the polypeptide of SEQ ID NO: 5, SEQ ID NO: 6, or the mature polypeptide of SEQ ID NO: 2 or SEQ ID NO: 4.

An embodiment of the invention is a polypeptide for use in animal feed having at least 99% sequence identity to the polypeptide of SEQ ID NO: 5, SEQ ID NO: 6, or the mature polypeptide of SEQ ID NO: 2 or SEQ ID NO: 4.

An embodiment of the invention is a polypeptide for use in animal feed having 100% sequence identity to the polypeptide of SEQ ID NO: 5, SEQ ID NO: 6, or the mature polypeptide of SEQ ID NO: 2 or SEQ ID NO: 4.

The present invention relates to the use in animal feed of isolated polypeptides having a sequence identity to the polypeptide of SEQ ID NO: 5, SEQ ID NO: 6, or the mature polypeptide of SEQ ID NO: 2 or SEQ ID NO: 4 of at least 60%, e.g., at least 70%, at least 80%, at least 85%, at least 87%, at least 90%, at least 91%, at least 92%, at least 93%, at least 94%, at least 95%, at least 96%, at least 97%, at least 98%, at least 99%, or 100%, which have protease activity. In one aspect, the polypeptides differ by no more than twenty amino acids, e.g., by fifteen amino acids, by ten amino acids, by eight amino acids, by seven amino acids, by six amino acids, by five amino acids, by four amino acids, by three amino acids, by two amino acids, and by one amino acid from the polypeptide of SEQ ID NO: 5, SEQ ID NO: 6, or the mature polypeptide of SEQ ID NO: 2 or SEQ ID NO: 4.

An embodiment of the invention is a polypeptide for use in animal feed having at least 70% sequence identity to the polypeptide of SEQ ID NO: 19, or the mature polypeptide of SEQ ID NO: 16 or SEQ ID NO: 18.

An embodiment of the invention is a polypeptide for use in animal feed having at least 75% sequence identity to the polypeptide of SEQ ID NO: 19, or the mature polypeptide of SEQ ID NO: 16 or SEQ ID NO: 18.

An embodiment of the invention is a polypeptide for use in animal feed having at least 80% sequence identity to the polypeptide of SEQ ID NO: 19, or the mature polypeptide of SEQ ID NO: 16 or SEQ ID NO: 18.

An embodiment of the invention is a polypeptide for use in animal feed having at least 85% sequence identity to the polypeptide of SEQ ID NO: 19, or the mature polypeptide of SEQ ID NO: 16 or SEQ ID NO: 18.

An embodiment of the invention is a polypeptide for use in animal feed having at least 87% sequence identity to the polypeptide of SEQ ID NO: 19, or the mature polypeptide of SEQ ID NO: 16 or SEQ ID NO: 18.

An embodiment of the invention is a polypeptide for use in animal feed having at least 90% sequence identity to the polypeptide of SEQ ID NO: 19, or the mature polypeptide of SEQ ID NO: 16 or SEQ ID NO: 18.

An embodiment of the invention is a polypeptide for use in animal feed having at least 91% sequence identity to the polypeptide of SEQ ID NO: 19, or the mature polypeptide of SEQ ID NO: 16 or SEQ ID NO: 18.

An embodiment of the invention is a polypeptide for use in animal feed having at least 92% sequence identity to the polypeptide of SEQ ID NO: 19, or the mature polypeptide of SEQ ID NO: 16 or SEQ ID NO: 18.

An embodiment of the invention is a polypeptide for use in animal feed having at least 93% sequence identity to the polypeptide of SEQ ID NO: 19, or the mature polypeptide of SEQ ID NO: 16 or SEQ ID NO: 18.

An embodiment of the invention is a polypeptide for use in animal feed having at least 94% sequence identity to the polypeptide of SEQ ID NO: 19, or the mature polypeptide of SEQ ID NO: 16 or SEQ ID NO: 18.

An embodiment of the invention is a polypeptide for use in animal feed having at least 95% sequence identity to the polypeptide of SEQ ID NO: 19, or the mature polypeptide of SEQ ID NO: 16 or SEQ ID NO: 18.

An embodiment of the invention is a polypeptide for use in animal feed having at least 96% sequence identity to the polypeptide of SEQ ID NO: 19, or the mature polypeptide of SEQ ID NO: 16 or SEQ ID NO: 18.

An embodiment of the invention is a polypeptide for use in animal feed having at least 97% sequence identity to the polypeptide of SEQ ID NO: 19, or the mature polypeptide of SEQ ID NO: 16 or SEQ ID NO: 18.

An embodiment of the invention is a polypeptide for use in animal feed having at least 98% sequence identity to the polypeptide of SEQ ID NO: 19, or the mature polypeptide of SEQ ID NO: 16 or SEQ ID NO: 18.

An embodiment of the invention is a polypeptide for use in animal feed having at least 99% sequence identity to the polypeptide of SEQ ID NO: 19, or the mature polypeptide of SEQ ID NO: 16 or SEQ ID NO: 18.

An embodiment of the invention is a polypeptide for use in animal feed having 100% sequence identity to the polypeptide of SEQ ID NO: 19, or the mature polypeptide of SEQ ID NO: 16 or SEQ ID NO: 18.

The present invention relates to the use in animal feed of isolated polypeptides having a sequence identity to the polypeptide of SEQ ID NO: 19, or the mature polypeptide of SEQ ID NO: 16 or SEQ ID NO: 18 of at least 60%, e.g., at least 70%, at least 80%, at least 85%, at least 87%, at least 90%, at least 91%, at least 92%, at least 93%, at least 94%, at least 95%, at least 96%, at least 97%, at least 98%, at least 99%, or 100%, which have protease activity. In one aspect, the polypeptides differ by no more than twenty amino acids, e.g., by fifteen amino acids, by ten amino acids, by eight amino acids, by seven amino acids, by six amino acids, by five amino acids, by four amino acids, by three amino acids, by two amino acids, and by one amino acid from the polypeptide of SEQ ID NO: 19, or the mature polypeptide of SEQ ID NO: 16 or SEQ ID NO: 18.

An embodiment of the invention is a polypeptide for use in animal feed having at least 70% sequence identity to the polypeptide of SEQ ID NO: 24, or the mature polypeptide of SEQ ID NO: 21 or SEQ ID NO: 23.

An embodiment of the invention is a polypeptide for use in animal feed having at least 75% sequence identity to the polypeptide of SEQ ID NO: 24, or the mature polypeptide of SEQ ID NO: 21 or SEQ ID NO: 23.

An embodiment of the invention is a polypeptide for use in animal feed having at least 80% sequence identity to the polypeptide of SEQ ID NO: 24, or the mature polypeptide of SEQ ID NO: 21 or SEQ ID NO: 23.

An embodiment of the invention is a polypeptide for use in animal feed having at least 85% sequence identity to the polypeptide of SEQ ID NO: 24, or the mature polypeptide of SEQ ID NO: 21 or SEQ ID NO: 23.

An embodiment of the invention is a polypeptide for use in animal feed having at least 87% sequence identity to the polypeptide of SEQ ID NO: 24, or the mature polypeptide of SEQ ID NO: 21 or SEQ ID NO: 23.

An embodiment of the invention is a polypeptide for use in animal feed having at least 90% sequence identity to the polypeptide of SEQ ID NO: 24, or the mature polypeptide of SEQ ID NO: 21 or SEQ ID NO: 23.

An embodiment of the invention is a polypeptide for use in animal feed having at least 91% sequence identity to the polypeptide of SEQ ID NO: 24, or the mature polypeptide of SEQ ID NO: 21 or SEQ ID NO: 23.

An embodiment of the invention is a polypeptide for use in animal feed having at least 92% sequence identity to the polypeptide of SEQ ID NO: 24, or the mature polypeptide of SEQ ID NO: 21 or SEQ ID NO: 23.

An embodiment of the invention is a polypeptide for use in animal feed having at least 93% sequence identity to the polypeptide of SEQ ID NO: 24, or the mature polypeptide of SEQ ID NO: 21 or SEQ ID NO: 23.

An embodiment of the invention is a polypeptide for use in animal feed having at least 94% sequence identity to the polypeptide of SEQ ID NO: 24, or the mature polypeptide of SEQ ID NO: 21 or SEQ ID NO: 23.

An embodiment of the invention is a polypeptide for use in animal feed having at least 95% sequence identity to the polypeptide of SEQ ID NO: 24, or the mature polypeptide of SEQ ID NO: 21 or SEQ ID NO: 23.

An embodiment of the invention is a polypeptide for use in animal feed having at least 96% sequence identity to the polypeptide of SEQ ID NO: 24, or the mature polypeptide of SEQ ID NO: 21 or SEQ ID NO: 23.

An embodiment of the invention is a polypeptide for use in animal feed having at least 97% sequence identity to the polypeptide of SEQ ID NO: 24, or the mature polypeptide of SEQ ID NO: 21 or SEQ ID NO: 23.

An embodiment of the invention is a polypeptide for use in animal feed having at least 98% sequence identity to the polypeptide of SEQ ID NO: 24, or the mature polypeptide of SEQ ID NO: 21 or SEQ ID NO: 23.

An embodiment of the invention is a polypeptide for use in animal feed having at least 99% sequence identity to the polypeptide of SEQ ID NO: 24, or the mature polypeptide of SEQ ID NO: 21 or SEQ ID NO: 23.

An embodiment of the invention is a polypeptide for use in animal feed having 100% sequence identity to the polypeptide of SEQ ID NO: 24, or the mature polypeptide of SEQ ID NO: 21 or SEQ ID NO: 23.

The present invention relates to the use in animal feed of isolated polypeptides having a sequence identity to the polypeptide of SEQ ID NO: 24, or the mature polypeptide of SEQ ID NO: 21 or SEQ ID NO: 23 of at least 60%, e.g., at least 70%, at least 80%, at least 85%, at least 87%, at least 90%, at least 91%, at least 92%, at least 93%, at least 94%, at least 95%, at least 96%, at least 97%, at least 98%, at least 99%, or 100%, which have protease activity. In one aspect, the polypeptides differ by no more than twenty amino acids, e.g., by fifteen amino acids, by ten amino acids, by eight amino acids, by seven amino acids, by six amino acids, by five amino acids, by four amino acids, by three amino acids, by two amino acids, and by one amino acid from the polypeptide of SEQ ID NO: 24, or the mature polypeptide of SEQ ID NO: 21 or SEQ ID NO: 23.

In a particular embodiment, the present invention also relates to a method for preparing an animal feed or feed additive, comprising preparing an animal feed or feed additive composition comprising an animal feed and a protease of selected from the group consisting of:

(a) a polypeptide of SEQ ID NO: 5, SEQ ID NO: 6, or the mature polypeptide of SEQ ID NO: 2 or SEQ ID NO: 4;

(b) a polypeptide of SEQ ID NO: 19, or the mature polypeptide of SEQ ID NO: 16 or SEQ ID NO: 18;

(c) a polypeptide of SEQ ID NO: 24, or the mature polypeptide of SEQ ID NO: 21 or SEQ ID NO: 23;

(d) a polypeptide having at least 60%, e.g., at least 70%, at least 80%, at least 85%, at least 87%, at least 90%, at least 91%, at least 92%, at least 93%, at least 94%, at least 95%, at least 96%, at least 97%, at least 98%, at least 99%, or 100% sequence identity to the polypeptide of SEQ ID NO: 5, SEQ ID NO: 6, or the mature polypeptide of SEQ ID NO: 2 or SEQ ID NO: 4;

(e) a polypeptide having at least 60%, e.g., at least 70%, at least 80%, at least 85%, at least 87%, at least 90%, at least 91%, at least 92%, at least 93%, at least 94%, at least 95%, at least 96%, at least 97%, at least 98%, at least 99%, or 100% sequence identity to the polypeptide of SEQ ID NO: 19, or the mature polypeptide of SEQ ID NO: 16 or SEQ ID NO: 18; and (f) a polypeptide having at least 60%, e.g., at least 70%, at least 80%, at least 85%, at least 87%, at least 90%, at least 91%, at least 92%, at least 93%, at least 94%, at least 95%, at least 96%, at least 97%, at least 98%, at least 99%, or 100% sequence identity to the polypeptide of SEQ ID NO: 24, or the mature polypeptide of SEQ ID NO: 21 or SEQ ID NO: 23.

The present invention also relates to an animal feed or feed additive composition comprising an animal feed and a protease of selected from the group consisting of:

(a) a polypeptide of SEQ ID NO: 5, SEQ ID NO: 6, or the mature polypeptide of SEQ ID NO: 2 or SEQ ID NO: 4;

(b) a polypeptide of SEQ ID NO: 19, or the mature polypeptide of SEQ ID NO: 16 or SEQ ID NO: 18;

(c) a polypeptide of SEQ ID NO: 24, or the mature polypeptide of SEQ ID NO: 21 or SEQ ID NO: 23;

(d) a polypeptide having at least 60%, e.g., at least 70%, at least 80%, at least 85%, at least 87%, at least 90%, at least 91%, at least 92%, at least 93%, at least 94%, at least 95%, at least 96%, at least 97%, at least 98%, at least 99%, or 100% sequence identity to the polypeptide of SEQ ID NO: 5, SEQ ID NO: 6, or the mature polypeptide of SEQ ID NO: 2 or SEQ ID NO: 4;

(e) a polypeptide having at least 60%, e.g., at least 70%, at least 80%, at least 85%, at least 87%, at least 90%, at least 91%, at least 92%, at least 93%, at least 94%, at least 95%, at least 96%, at least 97%, at least 98%, at least 99%, or 100% sequence identity to the polypeptide of SEQ ID NO: 19, or the mature polypeptide of SEQ ID NO: 16 or SEQ ID NO: 18; and (f) a polypeptide having at least 60%, e.g., at least 70%, at least 80%, at least 85%, at least 87%, at least 90%, at least 91%, at least 92%, at least 93%, at least 94%, at least 95%, at least 96%, at least 97%, at least 98%, at least 99%, or 100% sequence identity to the polypeptide of SEQ ID NO: 24, or the mature polypeptide of SEQ ID NO: 21 or SEQ ID NO: 23.

In one aspect, the polypeptides differ by no more than twenty amino acids, e.g., by fifteen amino acids, by ten amino acids, by eight amino acids, by seven amino acids, by six amino acids, by five amino acids, by four amino acids, by three amino acids, by two amino acids, and by one amino acid from the polypeptide of SEQ ID NO: 5, SEQ ID NO: 6, or the mature polypeptide of SEQ ID NO: 2 or SEQ ID NO: 4.

The animal feed compositions may in particular embodiments be in the form of a pellet, a mash or liquid composition, as further described herein.

A polypeptide of the present invention preferably comprises or consists of the amino acid sequence of SEQ ID NO: 5, SEQ ID NO: 6, or the mature polypeptide of SEQ ID NO: 2 or SEQ ID NO: 4, an allelic variant thereof; or is a fragment missing, e.g., 30, 25, 20, 15, 10 or 5 amino acids from the N- and/or C-terminal and having protease activity. In another aspect, the polypeptide comprises or consists of the polypeptide of SEQ ID NO: 5. In another preferred aspect, the polypeptide comprises or consists of amino acids 1 to 366 of SEQ ID NO: 2.

A polypeptide of the present invention preferably comprises or consists of the amino acid sequence of SEQ ID NO: 19, or the mature polypeptide of SEQ ID NO: 16 or SEQ ID NO: 18, an allelic variant thereof; or is a fragment missing, e.g., 30, 25, 20, 15, 10 or 5 amino acids from the N- and/or C-terminal and having protease activity. In another aspect, the polypeptide comprises or consists of the polypeptide of SEQ ID NO: 19. In another preferred aspect, the polypeptide comprises or consists of amino acids 1 to 366 of SEQ ID NO: 16.

A polypeptide of the present invention preferably comprises or consists of the amino acid sequence of SEQ ID NO: 24, or the mature polypeptide of SEQ ID NO: 21 or SEQ ID NO: 23, an allelic variant thereof; or is a fragment missing, e.g., 30, 25, 20, 15, 10 or 5 amino acids from the N- and/or C-terminal and having protease activity. In another aspect, the polypeptide comprises or consists of the polypeptide of SEQ ID NO: 24. In another preferred aspect, the polypeptide comprises or consists of amino acids 1 to 366 of SEQ ID NO: 21.

The present invention also relates to isolated polypeptides having protease activity that are encoded by polynucleotides that hybridize under low stringency conditions, medium stringency conditions, medium-high stringency conditions, high stringency conditions, or very high stringency conditions with (i) the mature polypeptide coding sequence of SEQ ID NO: 1, or (ii) the full-length complementary strand of (i) (J. Sambrook, E. F. Fritsch, and T. Maniatis, 1989, *Molecular Cloning, A Laboratory Manual,* 2d edition, Cold Spring Harbor, N.Y.).

The polynucleotide of SEQ ID NO: 1, SEQ ID NO: 15 or SEQ ID NO: 20 or a subsequence thereof, as well as the amino acid sequence of SEQ ID NO: 5, SEQ ID NO: 6, SEQ ID NO: 19, SEQ ID NO: 24, or the mature polypeptide of SEQ ID NO: 2, SEQ ID NO: 4, SEQ ID NO: 16, SEQ ID NO: 18, SEQ ID NO: 21 or SEQ ID NO: 23, or a fragment thereof, may be used to design nucleic acid probes to identify and clone DNA encoding polypeptides having protease activity from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 14, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

A genomic DNA or cDNA library prepared from such other strains may be screened for DNA that hybridizes with the probes described above and encodes a polypeptide having protease activity. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that is homologous with SEQ ID NO: 1, SEQ ID NO: 15 or SEQ ID NO: 20 or a subsequence thereof, the carrier material is preferably used in a Southern blot.

For purposes of the present invention, hybridization indicates that the polynucleotide hybridizes to a labelled nucleic acid probe corresponding to the mature polypeptide coding sequence of SEQ ID NO: 1, SEQ ID NO: 15 or SEQ ID NO: 20, its full-length complementary strand or a subsequence thereof under very low to very high stringency conditions. Molecules to which the nucleic acid probe hybridizes under these conditions can be detected using, for example, X-ray film or any other detection means known in the art.

In one aspect, the nucleic acid probe is the mature polypeptide coding sequence of SEQ ID NO: 1, SEQ ID NO: 15 or SEQ ID NO: 20. In another aspect, the nucleic acid probe is a fragment thereof. In another aspect, the nucleic acid probe is a polynucleotide that encodes the polypeptide of SEQ ID NO: 2, SEQ ID NO: 16, SEQ ID NO: 21 or a fragment thereof. In another preferred aspect, the nucleic acid probe is SEQ ID NO: 1, SEQ ID NO: 15 or SEQ ID NO: 20.

For long probes of at least 100 nucleotides in length, high to very high stringency conditions are defined as prehybridization and hybridization at 42° C. in 5×SSPE, 0.3% SDS, 200 micrograms/ml sheared and denatured salmon sperm DNA, and either 25% formamide for very low and low stringencies, 35% formamide for medium and medium-high stringencies, or 50% formamide for high and very high stringencies, following standard Southern blotting procedures for 12 to 24 hours optimally. The carrier material is finally washed three times each for 15 minutes using 2×SSC, 0.2% SDS at 65° C. (high stringency), and at 70° C. (very high stringency).

For short probes of about 15 nucleotides to about 70 nucleotides in length, stringency conditions are defined as prehybridization and hybridization at about 5° C. to about 10° C. below the calculated $T_m$ using the calculation according to Bolton and McCarthy (1962, *Proc. Natl. Acad. Sci. USA* 48:1390) in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml following standard Southern blotting procedures for 12 to 24 hours optimally. The carrier material is finally washed once in 6×SCC plus 0.1% SDS for 15 minutes and twice each for 15 minutes using 6×SSC at 5° C. to 10° C. below the calculated $T_m$.

The present invention also relates to isolated polypeptides having protease activity encoded by polynucleotides having a sequence identity to the mature polypeptide coding sequence of SEQ ID NO: 1 of at least 84%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%.

The present invention also relates to isolated polypeptides having protease activity encoded by polynucleotides having a sequence identity to the mature polypeptide coding sequence of SEQ ID NO: 15 of at least 83%, e.g., at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%.

The present invention also relates to isolated polypeptides having protease activity encoded by polynucleotides having a sequence identity to the mature polypeptide coding sequence of SEQ ID NO: 20 of at least 85%, e.g., at least 86%, at least 87%, at least 88%, at least 89%, at least 90%, at least 91%, at least 92%, at least 93%, at least 94%, at least 95%, at least 96%, at least 97%, at least 98%, at least 99%, or 100%.

In another embodiment, the present invention relates to variants comprising a substitution, deletion, and/or insertion at one or more (several) positions of SEQ ID NO: 5, SEQ ID NO: 6, or the mature polypeptide of SEQ ID NO: 2 or SEQ ID NO: 4, or a homologous sequence thereof. The amino acid changes may be of a minor nature, that is conservative amino acid substitutions, insertions or deletions that do not significantly affect the folding and/or activity of the protein; small deletions, typically of one to about 30 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tag or HQ-tag, an antigenic epitope or a binding domain.

In another embodiment, the present invention relates to variants comprising a substitution, deletion, and/or insertion at one or more (several) positions of SEQ ID NO: 19, or the mature polypeptide of SEQ ID NO: 16 or SEQ ID NO: 18, or a homologous sequence thereof. The amino acid changes may be of a minor nature, that is conservative amino acid substitutions, insertions or deletions that do not significantly affect the folding and/or activity of the protein; small deletions, typically of one to about 30 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tag or HQ-tag, an antigenic epitope or a binding domain.

In another embodiment, the present invention relates to variants comprising a substitution, deletion, and/or insertion at one or more (several) positions of SEQ ID NO: 24, or the mature polypeptide of SEQ ID NO: 21 or SEQ ID NO: 23, or a homologous sequence thereof. The amino acid changes may be of a minor nature, that is conservative amino acid substitutions, insertions or deletions that do not significantly affect the folding and/or activity of the protein; small deletions, typically of one to about 30 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tag or HQ-tag, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, *In, The Proteins*, Academic Press, New York. The most commonly occurring exchanges that are expected not to alter the specific activity substantially are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in a parent polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for protease activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identities of essential amino acids can also be inferred from analysis of identities with polypeptides that are related to the parent polypeptide.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204), and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

The present invention also relates to variant polypeptides having protease activity and having at least 84%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to SEQ ID NO: 5, SEQ ID NO: 6, or the mature polypeptide of SEQ ID NO: 2 or SEQ ID NO: 4 comprising at least one substitution, deletion, and/or insertion of at least one or more (several) amino acids of SEQ ID NO: 5, SEQ ID NO: 6, or the mature polypeptide of SEQ ID NO: 2 or SEQ ID NO: 4 or a homologous sequence thereof.

The variant polypeptide of the invention may in one embodiment have at least 85% sequence identity to SEQ ID NO: 5.

The variant polypeptide of the invention may in one embodiment have at least 86% sequence identity to SEQ ID NO: 5.

The variant polypeptide of the invention may in one embodiment have at least 87% sequence identity to SEQ ID NO: 5.

The variant polypeptide of the invention may in one embodiment have at least 88% sequence identity to SEQ ID NO: 5.

The variant polypeptide of the invention may in one embodiment have at least 89% sequence identity to SEQ ID NO: 5.

The variant polypeptide of the invention may in one embodiment have at least 90% sequence identity to SEQ ID NO: 5.

The variant polypeptide of the invention may in one embodiment have at least 91% sequence identity to SEQ ID NO: 5.

The variant polypeptide of the invention may in one embodiment have at least 92% sequence identity to SEQ ID NO: 5.

The variant polypeptide of the invention may in one embodiment have at least 93% sequence identity to SEQ ID NO: 5.

The variant polypeptide of the invention may in one embodiment have at least 94% sequence identity to SEQ ID NO: 5.

The variant polypeptide of the invention may in one embodiment have at least 95% sequence identity to SEQ ID NO: 5.

The variant polypeptide of the invention may in one embodiment have at least 96% sequence identity to SEQ ID NO: 5.

The variant polypeptide of the invention may in one embodiment have at least 97% sequence identity to SEQ ID NO: 5.

The variant polypeptide of the invention may in one embodiment have at least 98% sequence identity to SEQ ID NO: 5.

The variant polypeptide of the invention may in one embodiment have at least 99% sequence identity to SEQ ID NO: 5.

The total number of amino acid substitutions, deletions and/or insertions of the mature polypeptide of SEQ ID NO: 5, SEQ ID NO: 6, or the mature polypeptide of SEQ ID NO: 2 or SEQ ID NO: 4 is not more than 20, e.g., 1, 2, 3, 4, 5, 6, 7, 8, 9, 10, 11, 12, 13, 14, 15, 16, 17, 18, 19 or 20.

The present invention also relates to variant polypeptides having protease activity and having at least 83%, e.g., at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to SEQ ID NO: 19, or the mature polypeptide of SEQ ID NO: 16 or SEQ ID NO: 18 comprising at least one substitution, deletion, and/or insertion of at least one or more (several) amino acids of SEQ ID NO: 19, or the mature polypeptide of SEQ ID NO: 16 or SEQ ID NO: 18 or a homologous sequence thereof.

The variant polypeptide of the invention may in one embodiment have at least 84% sequence identity to SEQ ID NO: 19.

The variant polypeptide of the invention may in one embodiment have at least 85% sequence identity to SEQ ID NO: 19.

The variant polypeptide of the invention may in one embodiment have at least 86% sequence identity to SEQ ID NO: 19.

The variant polypeptide of the invention may in one embodiment have at least 87% sequence identity to SEQ ID NO: 19.

The variant polypeptide of the invention may in one embodiment have at least 88% sequence identity to SEQ ID NO: 19.

The variant polypeptide of the invention may in one embodiment have at least 89% sequence identity to SEQ ID NO: 19.

The variant polypeptide of the invention may in one embodiment have at least 90% sequence identity to SEQ ID NO: 19.

The variant polypeptide of the invention may in one embodiment have at least 91% sequence identity to SEQ ID NO: 19.

The variant polypeptide of the invention may in one embodiment have at least 92% sequence identity to SEQ ID NO: 19.

The variant polypeptide of the invention may in one embodiment have at least 93% sequence identity to SEQ ID NO: 19.

The variant polypeptide of the invention may in one embodiment have at least 94% sequence identity to SEQ ID NO: 19.

The variant polypeptide of the invention may in one embodiment have at least 95% sequence identity to SEQ ID NO: 19.

The variant polypeptide of the invention may in one embodiment have at least 96% sequence identity to SEQ ID NO: 19.

The variant polypeptide of the invention may in one embodiment have at least 97% sequence identity to SEQ ID NO: 19.

The variant polypeptide of the invention may in one embodiment have at least 98% sequence identity to SEQ ID NO: 19.

The variant polypeptide of the invention may in one embodiment have at least 99% sequence identity to SEQ ID NO: 19.

The total number of amino acid substitutions, deletions and/or insertions of the mature polypeptide of SEQ ID NO: 19, or the mature polypeptide of SEQ ID NO: 16 or SEQ ID NO: 18 is not more than 20, e.g., 1, 2, 3, 4, 5, 6, 7, 8, 9, 10, 11, 12, 13, 14, 15, 16, 17, 18, 19 or 20.

The present invention also relates to variant polypeptides having protease activity and having at least 85%, e.g., at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to SEQ ID NO: 24, or the mature polypeptide of SEQ ID NO: 21 or SEQ ID NO: 23 comprising at least one substitution, deletion, and/or insertion of at least one or more (several) amino acids of SEQ ID NO: 24, or the mature polypeptide of SEQ ID NO: 21 or SEQ ID NO: 23 or a homologous sequence thereof.

The variant polypeptide of the invention may in one embodiment have at least 86% sequence identity to SEQ ID NO: 24.

The variant polypeptide of the invention may in one embodiment have at least 87% sequence identity to SEQ ID NO: 24.

The variant polypeptide of the invention may in one embodiment have at least 88% sequence identity to SEQ ID NO: 24.

The variant polypeptide of the invention may in one embodiment have at least 89% sequence identity to SEQ ID NO: 24.

The variant polypeptide of the invention may in one embodiment have at least 90% sequence identity to SEQ ID NO: 24.

The variant polypeptide of the invention may in one embodiment have at least 91% sequence identity to SEQ ID NO: 24.

The variant polypeptide of the invention may in one embodiment have at least 92% sequence identity to SEQ ID NO: 24.

The variant polypeptide of the invention may in one embodiment have at least 93% sequence identity to SEQ ID NO: 24.

The variant polypeptide of the invention may in one embodiment have at least 94% sequence identity to SEQ ID NO: 24.

The variant polypeptide of the invention may in one embodiment have at least 95% sequence identity to SEQ ID NO: 24.

The variant polypeptide of the invention may in one embodiment have at least 96% sequence identity to SEQ ID NO: 24.

The variant polypeptide of the invention may in one embodiment have at least 97% sequence identity to SEQ ID NO: 24.

The variant polypeptide of the invention may in one embodiment have at least 98% sequence identity to SEQ ID NO: 24.

The variant polypeptide of the invention may in one embodiment have at least 99% sequence identity to SEQ ID NO: 24.

The total number of amino acid substitutions, deletions and/or insertions of the mature polypeptide of SEQ ID NO: 24, or the mature polypeptide of SEQ ID NO: 21 or SEQ ID NO: 23 is not more than 20, e.g., 1, 2, 3, 4, 5, 6, 7, 8, 9, 10, 11, 12, 13, 14, 15, 16, 17, 18, 19 or 20.

The polypeptide may be hybrid polypeptide in which a portion of one polypeptide is fused at the N-terminus or the C-terminus of a portion of another polypeptide.

The polypeptide may be a fusion polypeptide or cleavable fusion polypeptide in which another polypeptide is fused at the N-terminus or the C-terminus of the polypeptide of the present invention. A fused polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fused polypeptide is under control of the same promoter(s) and terminator. Fusion proteins may also be constructed using intein technology in which fusions are created post-translationally (Cooper et al., 1993, *EMBO J.* 12: 2575-2583; Dawson et al., 1994, *Science* 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, *Proteins: Structure, Function, and Genetics* 6: 240-248; and Stevens, 2003, *Drug Discovery World* 4: 35-48.

The polypeptide may be expressed by a recombinant DNA sequence containing the coding for a His-tag or HQ-tag to give, after any post-translational modifications, the mature polypeptide containing all or part of the His- or HQ-tag. The HQ-tag, having the sequence—RHQHQHQ, may be fully or partly cleaved off the polypeptide during the post-translational modifications resulting in for example the additional amino acids-RHQHQ attached to the C-terminal of the mature polypeptide.

Carbohydrate molecules are often attached to a polypeptide from a fungal source during post-translational modification. In order to aid mass spectrometry analysis, the polypeptide can be incubated with an endoglycosidase to deglycosylate each N-linked position. For every deglycosylated N-linked site, one N-acetyl hexosamine remains on the protein backbone.

EMBODIMENTS

In certain embodiments of the invention, the protease of the invention exhibits beneficial thermal properties such as thermostability, steam stability, etc and/or pH properties, such as acid stability, pH optimum, etc.

An embodiment of the invention is isolated polypeptides having improved protease activity between pH 2 and 5, such as between pH 2 and 4, preferably between pH 3 and 5, or more preferably between pH 3 and 4, at 25° C. compared to protease 10R.

A further embodiment of the invention is isolated polypeptides having improved protease activity at, e.g., 60° C. or below, preferably 50° C. or below, more preferably 37° C. or below; between 25° C. and 60° C., preferably between 25° C. and 50° C.; or at 25° C. or at 37° C. compared to protease 10R.

An additional embodiment of the invention is improved protease activity on soybean-maze meal between pH 3.0 and 4.0 at 40° C. compared to protease 10R.

Another embodiment of the invention is improved proteolytic activity on broiler digesta expressed as increase in level of primary amines in crop and/or gizzard digesta after 3 or 1 hour incubation when compared to a non-protease treated blank sample and when compared to a sample treated with protease 10R.

Acidity/Alkalinity Properties

In certain embodiments of the invention the protease of the invention exhibits beneficial properties in respect of pH, such as acid stability, pH optimum, etc. Stability of the protease at a low pH is beneficial since the protease can have activity in the intestine after passing through the stomach. In one embodiment of the invention, the protease retains >70% activity, such as >95% activity after 2 hours at pH 3 as determined using the method described in Example 3.

Temperature-Activity

The temperature-activity profile of the protease may be determined as described in Example 3. Activity at low temperatures (30-40° C.) can be advantageous for the digestion of proteins in an animal.

In one embodiment, the invention comprises of a protease having a temperature activity profile at pH 4.0 with relative activity of 0.20 or higher at 25° C., or relative activity of 0.50 or higher at 37° C. when compared to the activity of the protease at 50° C. (cf. Example 3).

Thermostability

Thermostability may be determined as described in Example 6, i.e., using DSC measurements to determine the denaturation temperature, $T_d$, of the purified protease protein. The Td is indicative of the thermostability of the protein: The higher the $T_d$, the higher the thermostability. Accordingly, in a preferred embodiment, the protease of the invention has a $T_d$ which is higher than the $T_d$ of a reference protease, wherein $T_d$ is determined on purified protease samples (preferably with a purity of at least 90% or 95%, as determined by SDS-PAGE).

In preferred embodiments, the thermal properties such as heat-stability, temperature stability, thermostability, steam stability, and/or pelleting stability as provided by the residual activity, denaturation temperature $T_d$, or other parameter of the protease of the invention is higher than the corresponding value, such as the residual activity or $T_d$, of the protease of SEQ ID NO: 6, more preferably at least 101% thereof, or at least 102%, 103%, 104%, 105%, 106%, 107%, 108%, 109%, or at least 110% thereof. Even more preferably, the value of the parameter, such as residual activity or $T_d$, of the protease of the invention is at least 120%, 130%, 140%, 150%, 160%, 170%, 180%, or at least 190% of the value for the protease of SEQ ID NO: 6.

In preferred embodiments, the thermal properties such as heat-stability, temperature stability, thermostability, steam stability, and/or pelleting stability as provided by the residual activity, denaturation temperature $T_d$, or other parameter of the protease of the invention is higher than the corresponding value, such as the residual activity or $T_d$, of the protease of SEQ ID NO: 19, more preferably at least 101% thereof, or at least 102%, 103%, 104%, 105%, 106%, 107%, 108%, 109%, or at least 110% thereof. Even more preferably, the value of the parameter, such as residual activity or $T_d$, of the protease of the invention is at least 120%, 130%, 140%, 150%, 160%, 170%, 180%, or at least 190% of the value for the protease of SEQ ID NO: 19.

In preferred embodiments, the thermal properties such as heat-stability, temperature stability, thermostability, steam stability, and/or pelleting stability as provided by the residual activity, denaturation temperature $T_d$, or other parameter of the protease of the invention is higher than the corresponding value, such as the residual activity or $T_d$, of the protease of SEQ ID NO: 24, more preferably at least 101% thereof, or at least 102%, 103%, 104%, 105%, 106%, 107%, 108%, 109%, or at least 110% thereof. Even more preferably, the value of the parameter, such as residual activity or $T_d$, of the protease of the invention is at least 120%, 130%, 140%, 150%, 160%, 170%, 180%, or at least 190% of the value for the protease of SEQ ID NO: 24.

In still further particular embodiments, the thermostable protease of the invention has a melting temperature, $T_m$ (or a denaturation temperature, $T_d$), as determined using Differential Scanning calorimetry (DSC) as described in example 10 (i.e., in 20 mM sodium acetate, pH 4.0), of at least 50° C. In still further particular embodiments, the $T_m$ is at least 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or at least 100° C.

Steam Stability

Steam stability may be determined as described in Example 7 by determining the residual activity of protease molecules after steam treatment at 85° C. or 90° C. for a short time.

Pelleting Stability

Pelleting stability may be determined as described in Example 8 by using enzyme granulate pre-mixed with feed. From the mixer the feed is conditioned with steam to 95° C. After conditioning the feed is pressed to pellets and the residual activity determined.

Sources of Polypeptides Having Protease Activity

A polypeptide having protease activity of the present invention may be obtained from fungi of any genus. For purposes of the present invention, the term "obtained from" as used herein in connection with a given source shall mean that the polypeptide encoded by a polynucleotide is produced by the source or by a strain in which the polynucleotide from the source has been inserted. In one aspect, the polypeptide obtained from a given source is secreted extracellularly.

The polypeptide may be a fungal polypeptide. For example, the polypeptide may be a polypeptide having protease activity from within a phylum such as Basidiomycota. In one aspect, the polypeptide is a protease from a fungus of the class Agaricomycetes, such as from the order Polyporales, or from the family Coriolaceae, or from the genus *Meripilus* or from the genus *Trametes*.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these taxa are readily accessible to the public in a number of culture collections, such as the American Type Culture Collection (ATCC), Deutsche Sammlung von Mikroorganismen and Zellkulturen GmbH (DSMZ), Centraalbureau Voor Schimmelcultures (CBS), and *Agricultural Research* Service Patent Culture Collection, Northern Regional Research Center (NRRL).

The polypeptide may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding the polypeptide may then be obtained by similarly screening a genomic DNA or cDNA library of another microorganism or mixed DNA sample. Once a polynucleotide encoding a polypeptide has been detected with the probe(s), the polynucleotide can be isolated or cloned by utilizing techniques that are known to those of ordinary skill in the art (see, e.g., Sambrook et al., 1989, supra).

Polynucleotides

The present invention also relates to isolated polynucleotides encoding a polypeptide of the present invention.

The techniques used to isolate or clone a polynucleotide encoding a polypeptide are known in the art and include isolation from genomic DNA, preparation from cDNA, or a combination thereof. The cloning of the polynucleotides from such genomic DNA can be effected, e.g., by using the well-known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligation activated transcription (LAT) and polynucleotide-based amplification (NASBA) may be used. The polynucleotides may be cloned from a strain of *Bacillus* sp., or another or related organism from the order Bacillales and thus, for example, may be an allelic or species variant of the polypeptide encoding region of the polynucleotide.

The present invention also relates to isolated polynucleotides comprising or consisting of polynucleotides having a degree of sequence identity to the mature polypeptide coding sequence of SEQ ID NO: 1 of at least 84%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, which encode a polypeptide having protease activity.

The present invention also relates to isolated polynucleotides comprising or consisting of polynucleotides having a degree of sequence identity to the mature polypeptide coding sequence of SEQ ID NO: 15 of at least 83%, e.g., at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, which encode a polypeptide having protease activity.

The present invention also relates to isolated polynucleotides comprising or consisting of polynucleotides having a degree of sequence identity to the mature polypeptide coding sequence of SEQ ID NO: 20 of at least 85%, e.g., at least 86%, at least 87%, at least 88%, at least 89%, at least 90%, at least 91%, at least 92%, at least 93%, at least 94%, at least 95%, at least 96%, at least 97%, at least 98%, at least 99%, or 100%, which encode a polypeptide having protease activity.

Modification of a polynucleotide encoding a polypeptide of the present invention may be necessary for the synthesis of polypeptides substantially similar to the polypeptide. The term "substantially similar" to the polypeptide refers to non-naturally occurring forms of the polypeptide. These polypeptides may differ in some engineered way from the polypeptide isolated from its native source, e.g., variants that differ in specific activity, thermostability, pH optimum, or the like. The variant may be constructed on the basis of the polynucleotide presented as the mature polypeptide coding sequence of SEQ ID NO: 1, SEQ ID NO: 15 or SEQ ID NO: 20, e.g., a subsequence thereof, and/or by introduction of nucleotide substitutions that do not result in a change in the amino acid sequence of the polypeptide, but which correspond to the codon usage of the host organism intended for production of the enzyme, or by introduction of nucleotide substitutions that may give rise to a different amino acid sequence. For a general description of nucleotide substitution, see, e.g., Ford et al., 1991, *Protein Expression and Purification* 2: 95-107.

The present invention also relates to isolated polynucleotides encoding polypeptides of the present invention, which hybridize under very low stringency conditions, low stringency conditions, medium stringency conditions, medium-high stringency conditions, high stringency conditions, or very high stringency conditions with (i) the mature polypeptide coding sequence of SEQ ID NO: 1, (ii) the genomic DNA sequence comprising the mature polypeptide coding sequence of SEQ ID NO: 1, or (iii) the full-length complementary strand of (i) or (ii); or allelic variants and subsequences thereof (Sambrook et al., 1989, supra), as defined herein.

In one aspect, the polynucleotide comprises or consists of SEQ ID NO: 1, the mature polypeptide coding sequence of SEQ ID NO: 1, or a subsequence of SEQ ID NO: 1 that encodes a fragment of SEQ ID NO: 2 having protease activity, such as the polynucleotide of nucleotides 605 to 1702 of SEQ ID NO: 1.

The present invention also relates to isolated polynucleotides encoding polypeptides of the present invention, which hybridize under very low stringency conditions, low stringency conditions, medium stringency conditions, medium-high stringency conditions, high stringency conditions, or very high stringency conditions with (i) the mature polypeptide coding sequence of SEQ ID NO: 15, (ii) the genomic DNA sequence comprising the mature polypeptide coding sequence of SEQ ID NO: 15, or (iii) the full-length complementary strand of (i) or (ii); or allelic variants and subsequences thereof (Sambrook et al., 1989, supra), as defined herein.

In one aspect, the polynucleotide comprises or consists of SEQ ID NO: 15, the mature polypeptide coding sequence of SEQ ID NO: 15, or a subsequence of SEQ ID NO: 15 that encodes a fragment of SEQ ID NO: 16 having protease activity, such as the joined sequence of nucleotides 1207 to 1353, nucleotides 1412 to 1522, nucleotides 1577 to 1776, nucleotides 1832 to 1969, nucleotides 2031 to 2478 and nucleotides 2531 to 2584 of SEQ ID NO: 15.

The present invention also relates to isolated polynucleotides encoding polypeptides of the present invention, which hybridize under very low stringency conditions, low stringency conditions, medium stringency conditions, medium-high stringency conditions, high stringency conditions, or very high stringency conditions with (i) the mature polypeptide coding sequence of SEQ ID NO: 20, (ii) the genomic DNA sequence comprising the mature polypeptide coding sequence of SEQ ID NO: 20, or (iii) the full-length complementary strand of (i) or (ii); or allelic variants and subsequences thereof (Sambrook et al., 1989, supra), as defined herein.

In one aspect, the polynucleotide comprises or consists of SEQ ID NO: 20, the mature polypeptide coding sequence of SEQ ID NO: 20, or a subsequence of SEQ ID NO: 20 that encodes a fragment of SEQ ID NO: 21 having protease activity, such as the joined sequence of nucleotides 1206 to 1352, nucleotides 1414 to 1524, nucleotides 1580 to 1779, nucleotides 1833 to 1970, nucleotides 2032 to 2479 and nucleotides 2532 to 2585 of SEQ ID NO: 20.

Nucleic Acid Constructs

The present invention also relates to nucleic acid constructs comprising a polynucleotide of the present invention operably linked to one or more (several) control sequences that direct the expression of the coding sequence in a suitable host cell under conditions compatible with the control sequences.

A polynucleotide may be manipulated in a variety of ways to provide for expression of the polypeptide. Manipulation of the polynucleotide prior to its insertion into a vector may be desirable or necessary depending on the expression vector. The techniques for modifying polynucleotides utilizing recombinant DNA methods are well known in the art.

The control sequence may be a promoter sequence, a polynucleotide that is recognized by a host cell for expression of a polynucleotide encoding a polypeptide of the present invention. The promoter sequence contains transcriptional control sequences that mediate the expression of the polypeptide. The promoter may be any polynucleotide that shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* cryIIIA gene (Agaisse and Lereclus, 1994, *Molecular Microbiology* 13: 97-107), *E. coli* lac operon, *E. coli* trc promoter (Egon et al., 1988, *Gene* 69: 301-315), *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American* 242: 74-94; and in Sambrook et al., 1989, supra. Examples of tandem promoters are disclosed in WO 99/43835.

Examples of suitable promoters for directing the transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Daria (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a modified promoter including a gene encoding a neutral alpha-amylase in Aspergilli in which the untranslated leader has been replaced by an untranslated leader from a gene encoding triose phosphate isomerase in Aspergilli; non-limiting examples include modified promoters including the gene encoding neutral alpha-amylase in *Aspergillus niger* in which the untranslated leader has been replaced by an untranslated leader from the gene encoding triose phosphate isomerase in *Aspergillus nidulans* or *Aspergillus oryzae*); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomy-*

*ces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a suitable transcription terminator sequence, which is recognized by a host cell to terminate transcription. The terminator sequence is operably linked to the 3'-terminus of the polynucleotide encoding the polypeptide. Any terminator that is functional in the host cell of choice may be used in the present invention.

Preferred terminators for bacterial host cells are obtained from the genes for *Bacillus clausii* alkaline protease (aprH), *Bacillus licheniformis* alpha-amylase (amyL), and *Escherichia coli* ribosomal RNA (rrnB).

Preferred terminators for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cryIIIA gene (WO 94/25612) and a *Bacillus subtilis* SP82 gene (Hue et al., 1995, *Journal of Bacteriology* 177: 3465-3471).

The control sequence may also be a leader, a nontranslated region of an mRNA that is important for translation by the host cell. The leader is operably linked to the 5'-terminus of the polynucleotide encoding the polypeptide. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the polynucleotide and, when transcribed, is recognized by the host cell as a signal to add polyadenosine residues to transcribed mRNA. Any polyadenylation sequence that is functional in the host cell of choice may be used.

Preferred polyadenylation sequences for filamentous fungal host cells are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. The foreign signal peptide coding sequence may be required where the coding sequence does not naturally contain a signal peptide coding sequence. Alternatively, the foreign signal peptide coding sequence may simply replace the natural signal peptide coding sequence in order to enhance secretion of the polypeptide. However, any signal peptide coding sequence that directs the expressed polypeptide into the secretory pathway of a host cell of choice may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), *Bacillus subtilis* prsA and *Bascillus lentus*. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present at the N-terminus of a polypeptide, the propeptide sequence is positioned next to the N-terminus of a polypeptide and the signal peptide sequence is positioned next to the N-terminus of the propeptide sequence.

It may also be desirable to add regulatory sequences that allow the regulation of the expression of the polypeptide relative to the growth of the host cell. Examples of regulatory systems are those that cause the expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked with the regulatory sequence.

Expression Vectors

The present invention also relates to recombinant expression vectors comprising a polynucleotide of the present invention, a promoter, and transcriptional and translational stop signals. The various nucleotide and control sequences may be joined together to produce a recombinant expression vector that may include one or more (several) convenient restriction sites to allow for insertion or substitution of the polynucleotide encoding the polypeptide at such sites. Alternatively, the polynucleotide may be expressed by inserting the polynucleotide or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more (several) selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin, or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene.

The vector preferably contains an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANSI (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide of the present invention operably linked to one or more (several) control sequences that direct the production of a polypeptide of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any cell useful in the recombinant production of a polypeptide of the present invention, e.g., a prokaryote or a eukaryote.

The prokaryotic host cell may be any Gram-positive or Gram-negative bacterium. Gram-positive bacteria include, but are not limited to, *Bacillus, Clostridium, Enterococcus, Geobacillus, Lactobacillus, Lactococcus, Oceanobacillus, Staphylococcus, Streptococcus*, and *Streptomyces*. Gram-negative bacteria include, but are not limited to, *Campylobacter, E. coli, Flavobacterium, Fusobacterium, Helicobacter, Ilyobacter, Neisseria, Pseudomonas, Salmonella*, and *Ureaplasma*.

The bacterial host cell may be any *Bacillus* cell including, but not limited to, *Bacillus alkalophilus, Bacillus amyloliquefaciens, Bacillus brevis, Bacillus circulans, Bacillus clausii, Bacillus coagulans, Bacillus firmus, Geobacillus stearothermophilus, Bacillus lautus, Bacillus lentus, Bacillus licheniformis, Bacillus megaterium, Bacillus pumilus, Bacillus stearothermophilus, Bacillus subtilis*, and *Bacillus thuringiensis* cells.

The bacterial host cell may also be any *Streptococcus* cell including, but not limited to, *Streptococcus equisimilis, Streptococcus pyogenes, Streptococcus uberis*, and *Streptococcus equi* subsp. *Zooepidemicus* cells.

The bacterial host cell may also be any *Streptomyces* cell including, but not limited to, *Streptomyces achromogenes, Streptomyces avermitilis, Streptomyces coelicolor, Streptomyces griseus*, and *Streptomyces lividans* cells.

The introduction of DNA into a *Bacillus* cell may, for instance, be effected by protoplast transformation (see, e.g., Chang and Cohen, 1979, *Mol. Gen. Genet.* 168: 111-115), by using competent cells (see, e.g., Young and Spizizen, 1961, *J. Bacteriol.* 81: 823-829, or Dubnau and Davidoff-Abelson, 1971, *J. Mol. Biol.* 56: 209-221), by electroporation (see, e.g., Shigekawa and Dower, 1988, *Biotechniques* 6: 742-751), or by conjugation (see, e.g., Koehler and Thorne, 1987, *J. Bacteriol.* 169: 5271-5278). The introduction of DNA into an *E. coli* cell may, for instance, be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may, for instance, be effected by protoplast transformation and electroporation (see, e.g., Gong et al., 2004, *Folia Microbiol.* (*Praha*) 49: 399-405), by conjugation (see, e.g., Mazodier et al., 1989, *J. Bacteriol.* 171: 3583-3585), or by transduction (see, e.g., Burke et al., 2001, *Proc. Natl. Acad. Sci. USA* 98: 6289-6294). The introduction of DNA into a *Pseudomonas* cell may, for instance, be effected by electroporation (see, e.g., Choi et al., 2006, *J. Microbiol. Methods* 64: 391-397) or by conjugation (see, e.g., Pinedo and Smets, 2005, Appl. *Environ. Microbiol.* 71: 51-57). The introduction of DNA into a *Streptococcus* cell may, for instance, be effected by natural competence (see, e.g., Perry and Kuramitsu, 1981, *Infect. Immun.* 32: 1295-1297), by protoplast transformation (see, e.g., Catt and Jollick, 1991, *Microbios* 68: 189-207), by electroporation (see, e.g., Buckley et al., 1999, *Appl. Environ. Microbiol.* 65: 3800-3804) or by conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota (as defined by Hawksworth et al., *In, Ainsworth and Bisby's Dictionary of The Fungi,* 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, F. A., Passmore, S. M., and Davenport, R. R., eds, *Soc. App. Bacteriol. Symposium Series No.* 9, 1980).

The yeast host cell may be a *Candida, Hansenula, Kluyveromyces, Pichia, Saccharomyces, Schizosaccharomyces*, or *Yarrowia* cell such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis*, or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes*, or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium suiphureum, Fusarium torulosum, Fusarium trichothecioides, Fusarium venenatum, Humicola insolens, Humicola lanuginose,*

*Mucor miehei, Myceliophthora thermophila, Neurospora crassa, Penicillium purpurogenum, Phanerochaete chrysosporium, Phiebia radiata, Pleurotus eryngii, Thielavia terrestris, Trametes villosa, Trametes versicolor, Trichoderma harzianum, Trichoderma koningii, Trichoderma longibrachiatum, Trichoderma reesei*, or *Trichoderma viride* cell. A specifically preferred host cell is an *Aspergillus oryzae* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023 and Yelton et al., 1984, *Proc. Natl. Acad. Sci. USA* 81: 1470-1474. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present invention also relates to methods of producing a polypeptide of the present invention, comprising: (a) cultivating a cell, which in its wild-type form produces the polypeptide, under conditions conducive for production of the polypeptide; and (b) recovering the polypeptide. In a preferred aspect, the cell is of the genus *Bacillus*. In a more preferred aspect, the cell is *Bacillus* sp. 19138.

The present invention also relates to methods of producing a polypeptide of the present invention, comprising: (a) cultivating a recombinant host cell of the present invention under conditions conducive for production of the polypeptide; and (b) recovering the polypeptide.

The host cells are cultivated in a nutrient medium suitable for production of the polypeptide using methods well known in the art. For example, the cell may be cultivated by shake flask cultivation, and small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

More details are provided in the Section on "Nucleic Acid Constructs, Expression Vectors, Recombinant Host Cells, and Methods for Production of Proteases" below.

The polypeptide may be detected using methods known in the art that are specific for the polypeptides. These detection methods may include use of specific antibodies, formation of an enzyme product, or disappearance of an enzyme substrate. For example, an enzyme assay may be used to determine the activity of the polypeptide.

The polypeptide may be recovered using methods known in the art. For example, the polypeptide may be recovered from the nutrient medium by conventional procedures including, but not limited to, centrifugation, filtration, extraction, spray-drying, evaporation, or precipitation.

The polypeptide may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, J.-C. Janson and Lars Ryden, editors, VCH Publishers, New York, 1989) to obtain substantially pure polypeptides.

In an alternative aspect, the polypeptide is not recovered, but rather a host cell of the present invention expressing a polypeptide is used as a source of the polypeptide.

Plants

The present invention also relates to plants, e.g., a transgenic plant, plant part, or plant cell, comprising an isolated polynucleotide of the present invention so as to express and produce the polypeptide in recoverable quantities. The polypeptide may be recovered from the plant or plant part. Alternatively, the plant or plant part containing the polypeptide may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, Poa), forage grass such as *Festuca, Lolium*, temperate grass, such as *Agrostis*, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana.*

Examples of plant parts are stem, callus, leaves, root, fruits, seeds, and tubers as well as the individual tissues comprising these parts, e.g., epidermis, mesophyll, parenchyme, vascular tissues, meristems. Specific plant cell compartments, such as chloroplasts, apoplasts, mitochondria, vacuoles, peroxisomes and cytoplasm are also considered to be a plant part. Furthermore, any plant cell, whatever the tissue origin, is considered to be a plant part. Likewise, plant parts such as specific tissues and cells isolated to facilitate the utilization of the invention are also considered plant parts, e.g., embryos, endosperms, aleurone and seeds coats.

Also included within the scope of the present invention are the progeny of such plants, plant parts, and plant cells.

The transgenic plant or plant cell expressing a polypeptide may be constructed in accordance with methods known in the art. In short, the plant or plant cell is constructed by incorporating one or more (several) expression constructs encoding a polypeptide into the plant host genome or chloroplast genome and propagating the resulting modified plant or plant cell into a transgenic plant or plant cell.

The expression construct is conveniently a nucleic acid construct that comprises a polynucleotide encoding a polypeptide operably linked with appropriate regulatory sequences required for expression of the polynucleotide in the plant or plant part of choice. Furthermore, the expression construct may comprise a selectable marker useful for identifying host cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences, is determined, for example, on the basis of when, where, and how the polypeptide is desired to be expressed. For instance, the expression of the gene encoding a polypeptide may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiology* 86: 506.

For constitutive expression, the 35S-CaMV, the maize ubiquitin 1, and the rice actin 1 promoter may be used (Franck et al., 1980, *Cell* 21: 285-294; Christensen et al., 1992, *Plant Mol. Biol.* 18: 675-689; Zhang et al., 1991, *Plant Cell* 3: 1155-1165). Organ-specific promoters may be, for example, a promoter from storage sink tissues such as seeds, potato tubers, and fruits (Edwards and Coruzzi, 1990, *Ann. Rev. Genet.* 24: 275-303), or from metabolic sink tissues such as meristems (Ito et al., 1994, *Plant Mol. Biol.* 24: 863-878), a seed specific promoter such as the glutelin, prolamin, globulin, or albumin promoter from rice (Wu et al., 1998, *Plant Cell Physiol.* 39: 885-889), a *Vicia faba* promoter from the legumin B4 and the unknown seed protein gene from *Vicia faba* (Conrad et al., 1998, *J. Plant Physiol.* 152: 708-711), a promoter from a seed oil body protein (Chen et al., 1998, *Plant Cell Physiol.* 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, *Plant Physiol.* 102: 991-1000), the chlorella virus adenine methyltransferase gene promoter (Mitra and Higgins, 1994, *Plant Mol. Biol.* 26: 85-93), the aldP gene promoter from rice (Kagaya et al., 1995, *Mol. Gen. Genet.* 248: 668-674), or a wound inducible promoter such as the potato pin2 promoter (Xu et al., 1993, *Plant Mol. Biol.* 22: 573-588). Likewise, the promoter may be inducible by abiotic treatments such as temperature, drought, or alterations in salinity or induced by exogenously applied substances that activate the promoter, e.g., ethanol, oestrogens, plant hormones such as ethylene, abscisic acid, and gibberellic acid, and heavy metals.

A promoter enhancer element may also be used to achieve higher expression of a polypeptide in the plant. For instance, the promoter enhancer element may be an intron that is placed between the promoter and the polynucleotide encoding a polypeptide. For instance, Xu et al., 1993, supra, disclose the use of the first intron of the rice actin 1 gene to enhance expression.

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535; Shimamoto et al., 1989, *Nature* 338: 274).

Presently, *Agrobacterium tumefaciens*-mediated gene transfer is the method of choice for generating transgenic dicots (for a review, see Hooykas and Schilperoort, 1992, *Plant Mol. Biol.* 19: 15-38) and can also be used for transforming monocots, although other transformation methods are often used for these plants. Presently, the method of choice for generating transgenic monocots is particle bombardment (microscopic gold or tungsten particles coated with the transforming DNA) of embryonic calli or developing embryos (Christou, 1992, *Plant J.* 2: 275-281; Shimamoto, 1994, *Curr. Opin. Biotechnol.* 5: 158-162; Vasil et al., 1992, *Bio/Technology* 10: 667-674). An alternative method for transformation of monocots is based on protoplast transformation as described by Omirulleh et al., 1993, *Plant Mol. Biol.* 21: 415-428. Additional transformation methods for use in accordance with the present disclosure include those described in U.S. Pat. Nos. 6,395,966 and 7,151,204 (both of which are herein incorporated by reference in their entirety).

Following transformation, the transformants having incorporated the expression construct are selected and regenerated into whole plants according to methods well known in the art. Often the transformation procedure is designed for the selective elimination of selection genes either during regeneration or in the following generations by using, for example, co-transformation with two separate T-DNA constructs or site-specific excision of the selection gene by a specific recombinase.

In addition to direct transformation of a particular plant genotype with a construct prepared according to the present invention, transgenic plants may be made by crossing a plant having the construct to a second plant lacking the construct. For example, a construct encoding a polypeptide can be introduced into a particular plant variety by crossing, without the need for ever directly transforming a plant of that given variety. Therefore, the present invention encompasses not only a plant directly regenerated from cells which have been transformed in accordance with the present invention, but also the progeny of such plants. As used herein, progeny may refer to the offspring of any generation of a parent plant prepared in accordance with the present invention. Such progeny may include a DNA construct prepared in accordance with the present invention, or a portion of a DNA construct prepared in accordance with the present invention. Crossing results in the introduction of a transgene into a plant line by cross pollinating a starting line with a donor plant line. Non-limiting examples of such steps are further articulated in U.S. Pat. No. 7,151,204.

Plants may be generated through a process of backcross conversion. For example, plants include plants referred to as a backcross converted genotype, line, inbred, or hybrid.

Genetic markers may be used to assist in the introgression of one or more transgenes of the invention from one genetic background into another. Marker assisted selection offers advantages relative to conventional breeding in that it can be used to avoid errors caused by phenotypic variations. Further, genetic markers may provide data regarding the relative degree of elite germplasm in the individual progeny of a particular cross. For example, when a plant with a desired trait which otherwise has a non-agronomically desirable genetic background is crossed to an elite parent, genetic markers may be used to select progeny which not only possess the trait of interest, but also have a relatively large proportion of the desired germplasm. In this way, the number of generations required to introgress one or more traits into a particular genetic background is minimized.

The present invention also relates to methods of producing a polypeptide of the present invention comprising: (a) cultivating a transgenic plant or a plant cell comprising a polynucleotide encoding the polypeptide under conditions conducive for production of the polypeptide; and (b) recovering the polypeptide.

Compositions

The present invention also relates to compositions comprising a protease of the present invention. Preferably, the compositions are enriched in such a protease. The term "enriched" indicates that the protease activity of the composition has been increased, e.g., with an enrichment factor of at least 1.1.

In one aspect, the composition comprises an isolated polypeptide having protease activity, selected from the group consisting of:

(a) a polypeptide having at least 60% sequence identity to the polypeptide of SEQ ID NO: 5, SEQ ID NO: 6, or the mature polypeptide of SEQ ID NO: 2 or SEQ ID NO: 4;

(b) a polypeptide having at least 60% sequence identity to the polypeptide of SEQ ID NO: 19, or the mature polypeptide of SEQ ID NO: 16 or SEQ ID NO: 18;

(c) a polypeptide having at least 60% sequence identity to the polypeptide of SEQ ID NO: 24, or the mature polypeptide of SEQ ID NO: 21 or SEQ ID NO: 23;

(d) a polypeptide encoded by a polynucleotide that hybridizes under medium stringency conditions, medium-high stringency conditions, high stringency conditions, or very high stringency conditions with (i) the mature polypeptide coding sequence of SEQ ID NO: 1, (ii) the mature polypeptide coding sequence of SEQ ID NO: 3, (iii) the mature polypeptide coding sequence of SEQ ID NO: 15, (iv) the mature polypeptide coding sequence of SEQ ID NO: 17, (v) the mature polypeptide coding sequence of SEQ ID NO: 20, (vi) the mature polypeptide coding sequence of SEQ ID NO: 22, (vii) the full-length complementary strand of (i), (ii), (iii), (iv), (v) or (vi);

(e) a polypeptide encoded by a polynucleotide having at least 84% sequence identity to the mature polypeptide coding sequence of SEQ ID NO: 1 or SEQ ID NO: 3;

(f) a polypeptide encoded by a polynucleotide having at least 83% sequence identity to the mature polypeptide coding sequence of SEQ ID NO: 15 or SEQ ID NO: 17;

(g) a polypeptide encoded by a polynucleotide having at least 85% sequence identity to the mature polypeptide coding sequence of SEQ ID NO: 20 or SEQ ID NO: 22;

(h) a variant of the polypeptide of SEQ ID NO: 5, SEQ ID NO: 6, SEQ ID NO: 19 or SEQ ID NO: 24, or the mature polypeptide of SEQ ID NO: 2, SEQ ID NO: 4, SEQ ID NO: 16, SEQ ID NO: 18, SEQ ID NO: 21 or SEQ ID NO: 23 comprising a substitution, deletion, and/or insertion at one or more (several) positions; and (i) a fragment of a polypeptide of (a), (b), (c), (d), (e), (f), (g) or (h) having protease activity.

An embodiment of the invention is a composition comprising a polypeptide having at least 70% sequence identity to the polypeptide of SEQ ID NO: 5, SEQ ID NO: 6, or the mature polypeptide of SEQ ID NO: 2 or SEQ ID NO: 4.

An embodiment of the invention is a composition comprising a polypeptide having at least 75% sequence identity to the polypeptide of SEQ ID NO: 5, SEQ ID NO: 6, or the mature polypeptide of SEQ ID NO: 2 or SEQ ID NO: 4.

An embodiment of the invention is a composition comprising a polypeptide having at least 80% sequence identity to the polypeptide of SEQ ID NO: 5, SEQ ID NO: 6, or the mature polypeptide of SEQ ID NO: 2 or SEQ ID NO: 4.

An embodiment of the invention is a composition comprising a polypeptide having at least 85% sequence identity to the polypeptide of SEQ ID NO: 5, SEQ ID NO: 6, or the mature polypeptide of SEQ ID NO: 2 or SEQ ID NO: 4.

An embodiment of the invention is a composition comprising a polypeptide having at least 87% sequence identity to the polypeptide of SEQ ID NO: 5, SEQ ID NO: 6, or the mature polypeptide of SEQ ID NO: 2 or SEQ ID NO: 4.

An embodiment of the invention is a composition comprising a polypeptide having at least 90% sequence identity to the polypeptide of SEQ ID NO: 5, SEQ ID NO: 6, or the mature polypeptide of SEQ ID NO: 2 or SEQ ID NO: 4.

An embodiment of the invention is a composition comprising a polypeptide having at least 91% sequence identity to the polypeptide of SEQ ID NO: 5, SEQ ID NO: 6, or the mature polypeptide of SEQ ID NO: 2 or SEQ ID NO: 4.

An embodiment of the invention is a composition comprising a polypeptide having at least 92% sequence identity to the polypeptide of SEQ ID NO: 5, SEQ ID NO: 6, or the mature polypeptide of SEQ ID NO: 2 or SEQ ID NO: 4.

An embodiment of the invention is a composition comprising a polypeptide having at least 93% sequence identity to the polypeptide of SEQ ID NO: 5, SEQ ID NO: 6, or the mature polypeptide of SEQ ID NO: 2 or SEQ ID NO: 4.

An embodiment of the invention is a composition comprising a polypeptide having at least 94% sequence identity to the polypeptide of SEQ ID NO: 5, SEQ ID NO: 6, or the mature polypeptide of SEQ ID NO: 2 or SEQ ID NO: 4.

An embodiment of the invention is a composition comprising a polypeptide having at least 95% sequence identity to the polypeptide of SEQ ID NO: 5, SEQ ID NO: 6, or the mature polypeptide of SEQ ID NO: 2 or SEQ ID NO: 4.

An embodiment of the invention is a composition comprising a polypeptide having at least 96% sequence identity to the polypeptide of SEQ ID NO: 5, SEQ ID NO: 6, or the mature polypeptide of SEQ ID NO: 2 or SEQ ID NO: 4.

An embodiment of the invention is a composition comprising a polypeptide having at least 97% sequence identity to the polypeptide of SEQ ID NO: 5, SEQ ID NO: 6, or the mature polypeptide of SEQ ID NO: 2 or SEQ ID NO: 4.

An embodiment of the invention is a composition comprising a polypeptide having at least 98% sequence identity to the polypeptide of SEQ ID NO: 5, SEQ ID NO: 6, or the mature polypeptide of SEQ ID NO: 2 or SEQ ID NO: 4.

An embodiment of the invention is a composition comprising a polypeptide having at least 99% sequence identity to the polypeptide of SEQ ID NO: 5, SEQ ID NO: 6, or the mature polypeptide of SEQ ID NO: 2 or SEQ ID NO: 4.

An embodiment of the invention is a composition comprising a polypeptide having 100% sequence identity to the polypeptide of SEQ ID NO: 5, SEQ ID NO: 6, or the mature polypeptide of SEQ ID NO: 2 or SEQ ID NO: 4.

In one aspect, the composition comprises or consists of the amino acid sequence of SEQ ID NO: 5, SEQ ID NO: 6, or the mature polypeptide of SEQ ID NO: 2 or SEQ ID NO: 4 or an allelic variant thereof; or is a fragment thereof having protease activity. In another aspect, the composition comprises or consists of the mature polypeptide of SEQ ID NO: 2 or SEQ ID NO: 4. In a further aspect, the composition comprises or consists of the polypeptide of SEQ ID NO: 5 or SEQ ID NO: 6. In another aspect, the composition comprises or consists of amino acids 1 to 366 of SEQ ID NO: 2, amino acids 1 to 366 of SEQ ID NO: 4, amino acids 1 to 366 of SEQ ID NO: 5 or amino acids 1 to 366 of SEQ ID NO: 6.

In an embodiment, the variant comprising a substitution, deletion, and/or insertion of one or more (several) amino acids of SEQ ID NO: 3 has at least 60%, e.g., at least 70%, at least 75%, at least 80%, at least 86%, at least 87%, at least 88%, at least 89%, at least 90%, at least 91%, at least 92%, at least 93%, at least 94%, at least 95%, at least 96%, at least 97%, at least 98%, at least 99%, but less than 100% sequence identity to SEQ ID NO: 5, SEQ ID NO: 6, or the mature polypeptide of SEQ ID NO: 2 or SEQ ID NO: 4.

An embodiment of the invention is a composition comprising a polypeptide having at least 70% sequence identity to the polypeptide of SEQ ID NO: 19, or the mature polypeptide of SEQ ID NO: 16 or SEQ ID NO: 18.

An embodiment of the invention is a composition comprising a polypeptide having at least 75% sequence identity to the polypeptide of SEQ ID NO: 19, or the mature polypeptide of SEQ ID NO: 16 or SEQ ID NO: 18.

An embodiment of the invention is a composition comprising a polypeptide having at least 80% sequence identity to the polypeptide of SEQ ID NO: 19, or the mature polypeptide of SEQ ID NO: 16 or SEQ ID NO: 18.

An embodiment of the invention is a composition comprising a polypeptide having at least 85% sequence identity to the polypeptide of SEQ ID NO: 19, or the mature polypeptide of SEQ ID NO: 16 or SEQ ID NO: 18.

An embodiment of the invention is a composition comprising a polypeptide having at least 87% sequence identity to the polypeptide of SEQ ID NO: 19, or the mature polypeptide of SEQ ID NO: 16 or SEQ ID NO: 18.

An embodiment of the invention is a composition comprising a polypeptide having at least 90% sequence identity to the polypeptide of SEQ ID NO: 19, or the mature polypeptide of SEQ ID NO: 16 or SEQ ID NO: 18.

An embodiment of the invention is a composition comprising a polypeptide having at least 91% sequence identity to the polypeptide of SEQ ID NO: 19, or the mature polypeptide of SEQ ID NO: 16 or SEQ ID NO: 18.

An embodiment of the invention is a composition comprising a polypeptide having at least 92% sequence identity to the polypeptide of SEQ ID NO: 19, or the mature polypeptide of SEQ ID NO: 16 or SEQ ID NO: 18.

An embodiment of the invention is a composition comprising a polypeptide having at least 93% sequence identity to the polypeptide of SEQ ID NO: 19, or the mature polypeptide of SEQ ID NO: 16 or SEQ ID NO: 18.

An embodiment of the invention is a composition comprising a polypeptide having at least 94% sequence identity to the polypeptide of SEQ ID NO: 19, or the mature polypeptide of SEQ ID NO: 16 or SEQ ID NO: 18.

An embodiment of the invention is a composition comprising a polypeptide having at least 95% sequence identity to the polypeptide of SEQ ID NO: 19, or the mature polypeptide of SEQ ID NO: 16 or SEQ ID NO: 18.

An embodiment of the invention is a composition comprising a polypeptide having at least 96% sequence identity to the polypeptide of SEQ ID NO: 19, or the mature polypeptide of SEQ ID NO: 16 or SEQ ID NO: 18.

An embodiment of the invention is a composition comprising a polypeptide having at least 97% sequence identity to the polypeptide of SEQ ID NO: 19, or the mature polypeptide of SEQ ID NO: 16 or SEQ ID NO: 18.

An embodiment of the invention is a composition comprising a polypeptide having at least 98% sequence identity to the polypeptide of SEQ ID NO: 19, or the mature polypeptide of SEQ ID NO: 16 or SEQ ID NO: 18.

An embodiment of the invention is a composition comprising a polypeptide having at least 99% sequence identity to the polypeptide of SEQ ID NO: 19, or the mature polypeptide of SEQ ID NO: 16 or SEQ ID NO: 18.

An embodiment of the invention is a composition comprising a polypeptide having 100% sequence identity to the polypeptide of SEQ ID NO: 19, or the mature polypeptide of SEQ ID NO: 16 or SEQ ID NO: 18.

In one aspect, the composition comprises or consists of the amino acid sequence of SEQ ID NO: 19, or the mature polypeptide of SEQ ID NO: 16 or SEQ ID NO: 18 or an allelic variant thereof; or is a fragment thereof having protease activity. In another aspect, the composition comprises or consists of the mature polypeptide of SEQ ID NO: 16 or SEQ ID NO: 18. In a further aspect, the composition comprises or consists of the polypeptide of SEQ ID NO: 19. In another aspect, the composition comprises or consists of amino acids 1 to 366 of SEQ ID NO: 16, amino acids 1 to 366 of SEQ ID NO: 18, or amino acids 1 to 366 of SEQ ID NO: 19.

In an embodiment, the variant comprising a substitution, deletion, and/or insertion of one or more (several) amino acids of SEQ ID NO: 19 has at least 60%, e.g., at least 70%, at least 75%, at least 80%, at least 86%, at least 87%, at least 88%, at least 89%, at least 90%, at least 91%, at least 92%, at least 93%, at least 94%, at least 95%, at least 96%, at least 97%, at least 98%, at least 99%, but less than 100% sequence identity to SEQ ID NO: 19, or the mature polypeptide of SEQ ID NO: 16 or SEQ ID NO: 18.

An embodiment of the invention is a composition comprising a polypeptide having at least 70% sequence identity to the polypeptide of SEQ ID NO: 24, or the mature polypeptide of SEQ ID NO: 21 or SEQ ID NO: 23.

An embodiment of the invention is a composition comprising a polypeptide having at least 75% sequence identity to the polypeptide of SEQ ID NO: 24, or the mature polypeptide of SEQ ID NO: 21 or SEQ ID NO: 23.

An embodiment of the invention is a composition comprising a polypeptide having at least 80% sequence identity to the polypeptide of SEQ ID NO: 24, or the mature polypeptide of SEQ ID NO: 21 or SEQ ID NO: 23.

An embodiment of the invention is a composition comprising a polypeptide having at least 85% sequence identity to the polypeptide of SEQ ID NO: 24, or the mature polypeptide of SEQ ID NO: 21 or SEQ ID NO: 23.

An embodiment of the invention is a composition comprising a polypeptide having at least 87% sequence identity to the polypeptide of SEQ ID NO: 24, or the mature polypeptide of SEQ ID NO: 21 or SEQ ID NO: 23.

An embodiment of the invention is a composition comprising a polypeptide having at least 90% sequence identity to the polypeptide of SEQ ID NO: 24, or the mature polypeptide of SEQ ID NO: 21 or SEQ ID NO: 23.

An embodiment of the invention is a composition comprising a polypeptide having at least 91% sequence identity to the polypeptide of SEQ ID NO: 24, or the mature polypeptide of SEQ ID NO: 21 or SEQ ID NO: 23.

An embodiment of the invention is a composition comprising a polypeptide having at least 92% sequence identity to the polypeptide of SEQ ID NO: 24, or the mature polypeptide of SEQ ID NO: 21 or SEQ ID NO: 23.

An embodiment of the invention is a composition comprising a polypeptide having at least 93% sequence identity to the polypeptide of SEQ ID NO: 24, or the mature polypeptide of SEQ ID NO: 21 or SEQ ID NO: 23.

An embodiment of the invention is a composition comprising a polypeptide having at least 94% sequence identity to the polypeptide of SEQ ID NO: 24, or the mature polypeptide of SEQ ID NO: 21 or SEQ ID NO: 23.

An embodiment of the invention is a composition comprising a polypeptide having at least 95% sequence identity to the polypeptide of SEQ ID NO: 24, or the mature polypeptide of SEQ ID NO: 21 or SEQ ID NO: 23.

An embodiment of the invention is a composition comprising a polypeptide having at least 96% sequence identity to the polypeptide of SEQ ID NO: 24, or the mature polypeptide of SEQ ID NO: 21 or SEQ ID NO: 23.

An embodiment of the invention is a composition comprising a polypeptide having at least 97% sequence identity to the polypeptide of SEQ ID NO: 24, or the mature polypeptide of SEQ ID NO: 21 or SEQ ID NO: 23.

An embodiment of the invention is a composition comprising a polypeptide having at least 98% sequence identity to the polypeptide of SEQ ID NO: 24, or the mature polypeptide of SEQ ID NO: 21 or SEQ ID NO: 23.

An embodiment of the invention is a composition comprising a polypeptide having at least 99% sequence identity to the polypeptide of SEQ ID NO: 24, or the mature polypeptide of SEQ ID NO: 21 or SEQ ID NO: 23.

An embodiment of the invention is a composition comprising a polypeptide having 100% sequence identity to the polypeptide of SEQ ID NO: 24, or the mature polypeptide of SEQ ID NO: 21 or SEQ ID NO: 23.

In one aspect, the composition comprises or consists of the amino acid sequence of SEQ ID NO: 24, or the mature polypeptide of SEQ ID NO: 21 or SEQ ID NO: 23 or an allelic variant thereof; or is a fragment thereof having protease activity. In another aspect, the composition comprises or consists of the mature polypeptide of SEQ ID NO: 21 or SEQ ID NO: 23. In a further aspect, the composition comprises or consists of the polypeptide of SEQ ID NO: 24. In another aspect, the composition comprises or consists of amino acids 1 to 366 of SEQ ID NO: 21, amino acids 1 to 366 of SEQ ID NO: 23, or amino acids 1 to 366 of SEQ ID NO: 24.

In an embodiment, the variant comprising a substitution, deletion, and/or insertion of one or more (several) amino acids of SEQ ID NO: 24 has at least 60%, e.g., at least 70%, at least 75%, at least 80%, at least 86%, at least 87%, at least 88%, at least 89%, at least 90%, at least 91%, at least 92%, at least 93%, at least 94%, at least 95%, at least 96%, at least 97%, at least 98%, at least 99%, but less than 100% sequence identity to SEQ ID NO: 24, or the mature polypeptide of SEQ ID NO: 21 or SEQ ID NO: 23

In a preferred embodiment, the composition is an animal feed composition which further comprises one or more amylases, phytases, xylanases, galactanases, alpha-galactosidases, proteases, phospholipases, beta-glucanases, or any mixture thereof.

In another preferred embodiment, the composition is an animal feed additive which further comprises at least one fat-soluble vitamin, and/or at least one water-soluble vitamin, and/or at least one trace mineral. The animal feed additive may further comprise one or more amylases, phytases, xylanases, galactanases, alpha-galactosidases, proteases, phospholipases, beta-glucanases, or any mixture thereof.

The composition may comprise a protease of the present invention as the major enzymatic component, e.g., a mono-component composition. Alternatively, the composition may comprise multiple enzymatic activities, such as an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, haloperoxidase, invertase, laccase, lipase, mannosidase, oxidase, pectinolytic enzyme, peptidoglutaminase, peroxidase, phytase, polyphenoloxidase, proteolytic enzyme, ribonuclease, transglutaminase, or xylanase. The additional enzyme(s) may be produced, for example, by microorganisms such as bacteria or fungi or by plants or by animals. The compositions may be prepared in accordance with methods known in the art and may be in the form of a liquid or a dry composition. For instance, the composition may be in the form of a granulate or a microgranulate. The protease may be stabilized in accordance with methods known in the art.

Uses

The present invention is also directed to methods for using the polypeptides having protease activity, or compositions thereof, for, e.g., animal feed.

Use in Animal Feed

The present invention is also directed to methods for using the proteases having protease activity in animal feed, as well as to feed compositions and feed additives comprising the proteases of the invention.

The term animal includes all animals. Examples of animals are non-ruminants, and ruminants. Ruminant animals include, for example, animals such as sheep, goats, and cattle, e.g., beef cattle, cows, and young calves. In a particular embodiment, the animal is a non-ruminant animal. Non-ruminant animals include mono-gastric animals, e.g., pigs or swine (including, but not limited to, piglets, growing pigs, and sows); poultry such as turkeys, ducks and chicken (including but not limited to broiler chicks, layers); horses (including but not limited to hotbloods, coldbloods and warm bloods), young calves; and fish (including but not limited to salmon, trout, tilapia, catfish and carps; and crustaceans (including but not limited to shrimps and prawns).

The term feed or feed composition means any compound, preparation, mixture, or composition suitable for, or intended for intake by an animal.

In the use according to the invention the protease can be fed to the animal before, after, or simultaneously with the diet. The latter is preferred.

In a particular embodiment, the protease, in the form in which it is added to the feed, or when being included in a feed additive, is well-defined. Well-defined means that the protease preparation is at least 50% pure as determined by Size-exclusion chromatography (see Example 12 of WO 01/58275). In other particular embodiments, the protease preparation is at least 60, 70, 80, 85, 88, 90, 92, 94, or at least 95% pure as determined by this method.

A well-defined protease preparation is advantageous. For instance, it is much easier to dose correctly to the feed a protease that is essentially free from interfering or contaminating other proteases. The term dose correctly refers in particular to the objective of obtaining consistent and constant results, and the capability of optimising dosage based upon the desired effect.

For the use in animal feed, however, the protease need not be that pure; it may, e.g., include other enzymes, in which case it could be termed a protease preparation.

The protease preparation can be (a) added directly to the feed (or used directly in a protein treatment process), or (b) it can be used in the production of one or more intermediate compositions such as feed additives or premixes that is subsequently added to the feed (or used in a treatment process). The degree of purity described above refers to the purity of the original protease preparation, whether used according to (a) or (b) above.

Protease preparations with purities of this order of magnitude are in particular obtainable using recombinant methods of production, whereas they are not so easily obtained and also subject to a much higher batch-to-batch variation when the protease is produced by traditional fermentation methods.

Such protease preparation may of course be mixed with other enzymes.

The protein may be an animal protein, such as meat and bone meal, feather meal, and/or fish meal; or it may be a vegetable protein.

The term vegetable proteins as used herein refers to any compound, composition, preparation or mixture that includes at least one protein derived from or originating from a vegetable, including modified proteins and protein-derivatives. In particular embodiments, the protein content of the vegetable proteins is at least 10, 20, 30, 40, 50, or 60% (w/w).

Vegetable proteins may be derived from vegetable protein sources, such as legumes and cereals, for example materials from plants of the families Fabaceae (Leguminosae), Cruciferaceae, Chenopodiaceae, and Poaceae, such as soy bean meal, lupin meal and rapeseed meal.

In a particular embodiment, the vegetable protein source is material from one or more plants of the family Fabaceae, e.g., soybean, lupine, pea, or bean.

In another particular embodiment, the vegetable protein source is material from one or more plants of the family Chenopodiaceae, e.g., beet, sugar beet, spinach or *quinoa.*

Other examples of vegetable protein sources are rapeseed, sunflower seed, cotton seed, and cabbage.

Soybean is a preferred vegetable protein source.

Other examples of vegetable protein sources are cereals such as barley, wheat, rye, oat, maize (corn), rice, triticale, and sorghum.

In a particular embodiment of a treatment process, the protease(s) in question is affecting (or acting on, or exerting its hydrolyzing or degrading influence on) the proteins, such as vegetable proteins or protein sources. To achieve this, the protein or protein source is typically suspended in a solvent, eg an aqueous solvent such as water, and the pH and temperature values are adjusted paying due regard to the characteristics of the enzyme in question. For example, the treatment may take place at a pH-value at which the activity of the actual protease is at least 5%, 10%, 20%, 30%, 40%, 50%, 60%, 70%, 80%, or at least 90%. Likewise, for example, the treatment may take place at a temperature at which the activity of the actual protease is at least 5%, 10%, 20%, 30%, 40%, 50%, 60%, 70%, 80%, or at least 90%. The above percentage activity indications are relative to the maximum activities. The enzymatic reaction is continued until the desired result is achieved, following which it may or may not be stopped by inactivating the enzyme, e.g., by a heat-treatment step.

In another particular embodiment of a treatment process of the invention, the protease action is sustained, meaning, e.g., that the protease is added to the proteins, but its hydrolyzing influence is so to speak not switched on until later when desired, once suitable hydrolyzing conditions are established, or once any enzyme inhibitors are inactivated, or whatever other means could have been applied to postpone the action of the enzyme.

In one embodiment, the treatment is a pre-treatment of animal feed or proteins for use in animal feed, i.e., the proteins are hydrolyzed before intake.

The term improving the nutritional value of an animal feed means improving the availability of nutrients in the feed. In this invention improving the nutritional values refers in particular to improving the availability of the protein fraction of the feed, thereby leading to increased protein extraction, higher protein yields, and/or improved protein utilization. When the nutritional value of the feed is increased, the protein and/or amino acid digestibility is increased and the growth rate and/or weight gain and/or feed conversion (i.e., the weight of ingested feed relative to weight gain) of the animal might be improved.

The protease can be added to the feed in any form, be it as a relatively pure protease or in admixture with other components intended for addition to animal feed, i.e., in the form of animal feed additives, such as the so-called premixes for animal feed.

In a further aspect, the present invention relates to compositions for use in animal feed, such as animal feed, and animal feed additives, e.g., premixes.

Apart from the protease of the invention, the animal feed additives of the invention contain at least one fat-soluble vitamin, and/or at least one water soluble vitamin, and/or at least one trace mineral, and/or at least one macro mineral.

Further, optional, feed-additive ingredients are colouring agents, e.g., carotenoids such as beta-carotene, astaxanthin, and lutein; stabilisers; growth improving additives and aroma compounds/flavorings, e.g., creosol, anethol, deca-, undeca- and/or dodeca-lactones, ionones, irone, gingerol, piperidine, propylidene phatalide, butylidene phatalide, capsaicin and/or tannin; antimicrobial peptides; polyunsaturated fatty acids (PUFAs); reactive oxygen generating species; also, a support may be used that may contain, for example, 40-50% by weight of wood fibres, 8-10% by weight of stearine, 4-5% by weight of curcuma powder, 4-58% by weight of rosemary powder, 22-28% by weight of limestone, 1-3% by weight of a gum, such as gum arabic, 5-50% by weight of sugar and/or starch and 5-15% by weight of water.

A feed or a feed additive of the invention may also comprise at least one other enzyme selected from amongst phytase (EC 3.1.3.8 or 3.1.3.26); xylanase (EC 3.2.1.8); galactanase (EC 3.2.1.89); alpha-galactosidase (EC 3.2.1.22); further protease (EC 3.4); phospholipase A1 (EC 3.1.1.32); phospholipase A2 (EC 3.1.1.4); lysophospholipase (EC 3.1.1.5); phospholipase C (3.1.4.3); phospholipase D (EC 3.1.4.4); amylase such as, for example, alpha-amylase (EC 3.2.1.1); lysozyme (EC 3.2.1.17); and/or beta-glucanase (EC 3.2.1.4 or EC 3.2.1.6).

In a particular embodiment, the feed or a feed additive of the invention also comprises a phytase (EC 3.1.3.8 or 3.1.3.26).

In a particular embodiment, the feed or a feed additive of the invention also comprises a xylanase (EC 3.2.1.8).

A feed or a feed additive of the invention may also comprise at least one probiotic or direct fed microbial (DFM) optionally together with one or more other enzymes selected from amongst phytase (EC 3.1.3.8 or 3.1.3.26); xylanase (EC 3.2.1.8); galactanase (EC 3.2.1.89); alpha-galactosidase (EC 3.2.1.22); further protease (EC 3.4), phospholipase A1 (EC 3.1.1.32); phospholipase A2 (EC 3.1.1.4); lysophospholipase (EC 3.1.1.5); phospholipase C (3.1.4.3); phospholipase D (EC 3.1.4.4); amylase such as, for example, alpha-amylase (EC 3.2.1.1); and/or beta-glucanase (EC 3.2.1.4 or EC 3.2.1.6).

The direct fed microbial may be a bacterium from one or more of the following genera: *Lactobacillus, Lactococcus, Streptococcus, Bacillus, Pediococcus, Enterococcus, Leuconostoc, Carnobacterium, Propionibacterium, Bifidobacterium, Clostridium* and *Megasphaera* or any combination thereof, preferably from *Bacillus subtilis, Bacillus licheniformis, Bacillus amyloliquefaciens, Enterococcus faecium, Enterococcus* spp, and *Pediococcus* spp, *Lactobacillus* spp, *Bifidobacterium* spp, *Lactobacillus acidophilus, Pediococsus acidilactici, Lactococcus lactis, Bifidobacterium bifidum, Propionibacterium thoenii, Lactobacillus farciminus, Lactobacillus rhamnosus, Clostridium butyricum, Bifido-*

*bacterium animalis* ssp. *animalis, Lactobacillus reuteri, Bacillus cereus, Lactobacillus salivarius* ssp. *salivarius, Megasphaera elsdenii, Propionibacteria* sp and more preferably from *Bacillus subtilis* strains 3A-P4 (PTA-6506); 15A-P4 (PTA-6507); 22C-P1 (PTA-6508); 2084 (NRRL B-500130); LSSA01 (NRRL-B-50104); BS27 (NRRL B-501 05); BS 18 (NRRL B-50633); and BS 278 (NRRL B-50634).

In a particular embodiment, these other enzymes are well-defined (as defined above for protease preparations).

Examples of antimicrobial peptides (AMP's) are CAP18, Leucocin A, Tritrpticin, Protegrin-1, Thanatin, Defensin, Lactoferrin, Lactoferricin, and Ovispirin such as Novispirin (Robert Lehrer, 2000), Plectasins, and Statins, including the compounds and polypeptides disclosed in WO 03/044049 and WO 03/048148, as well as variants or fragments of the above that retain antimicrobial activity.

Examples of antifungal polypeptides (AFP's) are the *Aspergillus giganteus*, and *Aspergillus niger* peptides, as well as variants and fragments thereof which retain antifungal activity, as disclosed in WO 94/01459 and WO 02/090384.

Examples of polyunsaturated fatty acids are C18, C20 and C22 polyunsaturated fatty acids, such as arachidonic acid, docosohexaenoic acid, eicosapentaenoic acid and gamma-linoleic acid.

Examples of reactive oxygen generating species are chemicals such as perborate, persulphate, or percarbonate; and enzymes such as an oxidase, an oxygenase or a syntethase.

Usually fat- and water-soluble vitamins, as well as trace minerals form part of a so-called premix intended for addition to the feed, whereas macro minerals are usually separately added to the feed. Either of these composition types, when enriched with a protease of the invention, is an animal feed additive of the invention.

In a particular embodiment, the animal feed additive of the invention is intended for being included (or prescribed as having to be included) in animal diets or feed at levels of 0.01 to 10.0%; more particularly 0.05 to 5.0%; or 0.2 to 1.0% (% meaning g additive per 100 g feed). This is so in particular for premixes.

The following are non-exclusive lists of examples of these components:

Examples of fat-soluble vitamins are vitamin A, vitamin D3, vitamin E, and vitamin K, e.g., vitamin K3.

Examples of water-soluble vitamins are vitamin B12, biotin and choline, vitamin B1, vitamin B2, vitamin B6, niacin, folic acid and panthothenate, e.g., Ca-D-panthothenate.

Examples of trace minerals are manganese, zinc, iron, copper, iodine, selenium, and cobalt.

Examples of macro minerals are calcium, phosphorus and sodium.

The nutritional requirements of these components (exemplified with poultry and piglets/pigs) are listed in Table A of WO 01/58275. Nutritional requirement means that these components should be provided in the diet in the concentrations indicated.

In the alternative, the animal feed additive of the invention comprises at least one of the individual components specified in Table A of WO 01/58275. At least one means either of, one or more of, one, or two, or three, or four and so forth up to all thirteen, or up to all fifteen individual components. More specifically, this at least one individual component is included in the additive of the invention in such an amount as to provide an in-feed-concentration within the range indicated in column four, or column five, or column six of Table A.

In a still further embodiment, the animal feed additive of the invention comprises at least one of the below vitamins, preferably to provide an in-feed-concentration within the ranges specified in the below Table 1 (for piglet diets, and broiler diets, respectively).

TABLE 1

Typical vitamin recommendations

| Vitamin | Piglet diet | Broiler diet |
|---|---|---|
| Vitamin A | 10,000-15,000 IU/kg feed | 8-12,500 IU/kg feed |
| Vitamin D3 | 1800-2000 IU/kg feed | 3000-5000 IU/kg feed |
| Vitamin E | 60-100 mg/kg feed | 150-240 mg/kg feed |
| Vitamin K3 | 2-4 mg/kg feed | 2-4 mg/kg feed |
| Vitamin B1 | 2-4 mg/kg feed | 2-3 mg/kg feed |
| Vitamin B2 | 6-10 mg/kg feed | 7-9 mg/kg feed |
| Vitamin B6 | 4-8 mg/kg feed | 3-6 mg/kg feed |
| Vitamin B12 | 0.03-0.05 mg/kg feed | 0.015-0.04 mg/kg feed |
| Niacin (Vitamin B3) | 30-50 mg/kg feed | 50-80 mg/kg feed |
| Pantothenic acid | 20-40 mg/kg feed | 10-18 mg/kg feed |
| Folic acid | 1-2 mg/kg feed | 1-2 mg/kg feed |
| Biotin | 0.15-0.4 mg/kg feed | 0.15-0.3 mg/kg feed |
| Choline chloride | 200-400 mg/kg feed | 300-600 mg/kg feed |

The present invention also relates to animal feed compositions. Animal feed compositions or diets have a relatively high content of protein. Poultry and pig diets can be characterised as indicated in Table B of WO 01/58275, columns 2-3. Fish diets can be characterised as indicated in column 4 of this Table B. Furthermore, such fish diets usually have a crude fat content of 200-310 g/kg.

WO 01/58275 corresponds to U.S. Ser. No. 09/779,334 which is hereby incorporated by reference.

An animal feed composition according to the invention has a crude protein content of 50-800 g/kg, and furthermore comprises at least one protease as claimed herein.

Furthermore, or in the alternative (to the crude protein content indicated above), the animal feed composition of the invention has a content of metabolisable energy of 10-30 MJ/kg; and/or a content of calcium of 0.1-200 g/kg; and/or a content of available phosphorus of 0.1-200 g/kg; and/or a content of methionine of 0.1-100 g/kg; and/or a content of methionine plus cysteine of 0.1-150 g/kg; and/or a content of lysine of 0.5-50 g/kg.

In particular embodiments, the content of metabolisable energy, crude protein, calcium, phosphorus, methionine, methionine plus cysteine, and/or lysine is within any one of ranges 2, 3, 4 or 5 in Table B of WO 01/58275 (R. 2-5).

Crude protein is calculated as nitrogen (N) multiplied by a factor 6.25, i.e., Crude protein (g/kg)=N (g/kg)×6.25. The nitrogen content is determined by the Kjeldahl method (A.O.A.C., 1984, Official Methods of Analysis 14th ed., Association of Official Analytical Chemists, Washington D.C.).

Metabolisable energy can be calculated on the basis of the NRC publication Nutrient requirements in swine, ninth revised edition 1988, subcommittee on swine nutrition, committee on animal nutrition, board of agriculture, national research council. National Academy Press, Washington, D.C., pp. 2-6, and the European Table of Energy Values for Poultry Feed-stuffs, Spelderholt centre for poultry research and extension, 7361 DA Beekbergen, The Netherlands. Grafisch bedrijf Ponsen & looijen bv, Wageningen. ISBN 90-71463-12-5.

The dietary content of calcium, available phosphorus and amino acids in complete animal diets is calculated on the basis of feed tables such as Veevoedertabel 1997, gegevens over chemische samenstelling, verteerbaarheid en voederwaarde van voedermiddelen, Central Veevoederbureau, Runderweg 6, 8219 pk Lelystad. ISBN 90-72839-13-7.

In a particular embodiment, the animal feed composition of the invention contains at least one vegetable protein as defined above.

The animal feed composition of the invention may also contain animal protein, such as Meat and Bone Meal, Feather meal, and/or Fish Meal, typically in an amount of 0-25%. The animal feed composition of the invention may also comprise Dried Destillers Grains with Solubles (DDGS), typically in amounts of 0-30%.

In still further particular embodiments, the animal feed composition of the invention contains 0-80% maize; and/or 0-80% sorghum; and/or 0-70% wheat; and/or 0-70% Barley; and/or 0-30% oats; and/or 0-40% soybean meal; and/or 0-25% fish meal; and/or 0-25% meat and bone meal; and/or 0-20% whey.

Animal diets can, e.g., be manufactured as mash feed (non-pelleted) or pelleted feed. Typically, the milled feedstuffs are mixed and sufficient amounts of essential vitamins and minerals are added according to the specifications for the species in question. Enzymes can be added as solid or liquid enzyme formulations. For example, for mash feed a solid or liquid enzyme formulation may be added before or during the ingredient mixing step. For pelleted feed, the (liquid or solid) protease/enzyme preparation may also be added before or during the feed ingredient step. Typically, a liquid protease/enzyme preparation is added after the pelleting step. The enzyme may also be incorporated in a feed additive or premix.

The final enzyme concentration in the diet is within the range of 0.01-200 mg enzyme protein per kg diet, for example in the range of 0.5-25 mg enzyme protein per kg animal diet.

The protease should of course be applied in an effective amount, i.e., in an amount adequate for improving hydrolysis, digestibility, and/or improving nutritional value of feed. It is at present contemplated that the enzyme is administered in one or more of the following amounts (dosage ranges): 0.01-200; 0.01-100; 0.5-100; 1-50; 5-100; 10-100; 0.05-50; or 0.10-10—all these ranges being in mg protease protein per kg feed (ppm).

For determining mg protease protein per kg feed, the protease is purified from the feed composition, and the specific activity of the purified protease is determined using a relevant assay (see under protease activity, substrates, and assays). The protease activity of the feed composition as such is also determined using the same assay, and on the basis of these two determinations, the dosage in mg protease protein per kg feed is calculated.

The same principles apply for determining mg protease protein in feed additives. Of course, if a sample is available of the protease used for preparing the feed additive or the feed, the specific activity is determined from this sample (no need to purify the protease from the feed composition or the additive).

Nucleic Acid Constructs, Expression Vectors, Recombinant Host Cells, and Methods for Production of Proteases The present invention also relates to nucleic acid constructs, expression vectors and recombinant host cells comprising such polynucleotides encoding the proteases of the invention.

The present invention also relates to methods of producing a protease, comprising: (a) cultivating a recombinant host cell comprising such polynucleotide; and (b) recovering the protein.

The protein may be native or heterologous to a host cell. The term "protein" is not meant herein to refer to a specific length of the encoded product and, therefore, encompasses peptides, oligopeptides, and proteins. The term "protein" also encompasses two or more polypeptides combined to form the encoded product. The proteins also include hybrid polypeptides and fused polypeptides.

Preferably, the protein is a protease. For example, the protein may be a hydrolase, such as a proteolytic enzyme or protease.

The gene may be obtained from any prokaryotic, eukaryotic, or other source.

The present invention is further described by the following examples that should not be construed as limiting the scope of the invention.

EXAMPLES

Materials and Methods

Media

DAP4C-1 medium was composed of 0.5 g yeast extract, 10 g maltose, 20 g dextrose, 11 g magnesium sulphate heptahydrate, 1 g dipotassium phosphate, 2 g citric acid monohydrate, 5.2 g potassium phosphate tribasic monohydrate, 1 ml Dowfax 63N10 (antifoaming agent), 2.5 g calcium carbonate, supplemented with 1 ml KU6 metal solution, and deionised water to 1000 ml.

KU6 metal solution was composed of 6.8 g $ZnCl_2$, 2.5 g $CuSO_4.5H_2O$, 0.13 g $NiCl_2$, 13.9 g $FeSO_4.7H_2O$, 8.45 g $MnSO_4.H_2O$, 3 g $C_6H_8O_7.H_2O$, and deionised water to 1000 ml.

LB plates were composed of 10 g of Bacto-tryptone, 5 g of yeast extract, 10 g of sodium chloride, 15 g of Bacto-agar, and deionised water to 1000 ml.

LB medium was composed of 10 g of Bacto-tryptone, 5 g of yeast extract, and 10 g of sodium chloride, and deionised water to 1000 ml.

COVE-Sucrose-T plates were composed of 342 g of sucrose, 20 g of agar powder, 20 ml of COVE salt solution, and deionised water to 1000 ml. The medium was sterilized by autoclaving at 15 psi for 15 minutes (Bacteriological Analytical Manual, 8th Edition, Revision A, 1998). The medium was cooled to 60° C. and 10 mM acetamide, Triton X-100 (50 μl/500 ml) was added.

COVE-N-Agar tubes were composed of 218 g Sorbitol, 10 g Dextrose, 2.02 g $KNO_3$, 25 g Agar, 50 ml Cove salt solution, and deionised water up to 1000 ml.

COVE salt solution was composed of 26 g of $MgSO_4.7H_2O$, 26 g of KCL, 26 g of $KH_2PO_4$, 50 ml of COVE trace metal solution, and deionised water to 1000 ml.

COVE trace metal solution was composed of 0.04 g of $Na_2B_4O_7.10H_2O$, 0.4 g of $CuSO_4.5H_2O$, 1.2 g of $FeSO_4.7H_2O$, 0.7 g of $MnSO_4.H_2O$, 0.8 g of $Na_2MoO_4.2H_2O$, 10 g of $ZnSO_4.7H_2O$, and deionised water to 1000 ml.

Protease Assays

Kinetic Suc-AAPF-pNA Assay:

pNA substrate: Suc-AAPF-pNA (Bachem L-1400).

Temperature: Room temperature (25° C.)

Assay buffers: 100 mM succinic acid, 100 mM HEPES, 100 mM CHES, 100 mM CABS, 1 mM $CaCl_2$, 150 mM KCl, 0.01% Triton X-100 adjusted to pH-values 2.0, 3.0, 4.0, 5.0, 6.0, 7.0, 8.0, 9.0, 10.0, and 11.0 with HCl or NaOH.

20 μl protease sample (diluted in 0.01% Triton X-100) was mixed with 100 μl assay buffer. The assay was started by adding 100 μl pNA substrate (50 mg dissolved in 1.0 ml DMSO and further diluted 45× with 0.01% Triton X-100). The increase in $OD_{405}$ was monitored as a measure of the protease activity.

Endpoint Suc-AAPF-pNA Assay:

pNA substrate: Suc-AAPF-pNA (Bachem L-1400).

Temperature: controlled (assay temperature).

Assay buffer: 100 mM succinic acid, 100 mM HEPES, 100 mM CHES, 100 mM CABS, 1 mM $CaCl_2$, 150 mM KCl, 0.01% Triton X-100, pH 4.0

200 μl pNA substrate (50 mg dissolved in 1.0 ml DMSO and further diluted 45× with the Assay buffer) were pipetted in an Eppendorf tube and placed on ice. 20 μl protease sample (diluted in 0.01% Triton X-100) was added. The assay was initiated by transferring the Eppendorf tube to an Eppendorf thermomixer, which was set to the assay temperature. The tube was incubated for 15 minutes on the Eppendorf thermomixer at its highest shaking rate (1400 rpm). The incubation was stopped by transferring the tube back to the ice bath and adding 600 μl 500 mM $H_3BO_3$/NaOH, pH 9.7. The tube was mixed and 200 μl mixture was transferred to a microtiter plate, which was read at $OD_{405}$. A buffer blind was included in the assay (instead of enzyme). $OD_{405}$(Sample)−$OD_{405}$(Blind) was a measure of protease activity.

Protazyme AK Assay:

Substrate: Protazyme AK tablet (cross-linked and dyed casein; from Megazyme)

Temperature: controlled (assay temperature).

Assay buffer: 100 mM succinic acid, 100 mM HEPES, 100 mM CHES, 100 mM CABS, 1 mM $CaCl_2$, 150 mM KCl, 0.01% Triton X-100, pH 6.5.

A Protazyme AK tablet was suspended in 2.0 ml 0.01% Triton X-100 by gentle stirring. 500 μl of this suspension and 500 μl assay buffer were dispensed in an Eppendorf tube and placed on ice. 20 μl protease sample (diluted in 0.01% Triton X-100) was added. The assay was initiated by transferring the Eppendorf tube to an Eppendorf thermomixer, which was set to the assay temperature. The tube was incubated for 15 minutes on the Eppendorf thermomixer at its highest shaking rate (1400 rpm). The incubation was stopped by transferring the tube back to the ice bath. Then the tube was centrifuged in an ice cold centrifuge for a few minutes and 200 μl supernatant was transferred to a microtiter plate, which was read at $OD_{650}$. A buffer blind was included in the assay (instead of enzyme). $OD_{650}$(Sample)−$OD_{650}$(Blind) was a measure of protease activity.

Kinetic Suc-AAPX-pNA Assay:

pNA substrates: Suc-AAPA-pNA (Bachem L-1775)
Suc-AAPR-pNA (Bachem L-1720)
Suc-AAPD-pNA (Bachem L-1835)
Suc-AAPI-pNA (Bachem L-1790)
Suc-AAPM-pNA (Bachem L-1395)
Suc-AAPV-pNA (Bachem L-1770)
Suc-AAPL-pNA (Bachem L-1390)
Suc-AAPE-pNA (Bachem L-1710)
Suc-AAPK-pNA (Bachem L-1725)
Suc-AAPF-pNA (Bachem L-1400)

Temperature: Room temperature (25° C.)

Assay buffer: 100 mM succinic acid, 100 mM HEPES, 100 mM CHES, 100 mM CABS, 1 mM $CaCl_2$, 150 mM KCl, 0.01% Triton X-100, pH 4.0 or pH 9.0.

20 μl protease (diluted in 0.01% Triton X-100) was mixed with 100 μl assay buffer. The assay was started by adding 100 μl pNA substrate (50 mg dissolved in 1.0 ml DMSO and further diluted 45× with 0.01% Triton X-100). The increase in $OD_{405}$ was monitored as a measure of the protease activity.

o-Phthaldialdehyde (OPA) Assay:

This assay detects primary amines and hence cleavage of peptide bonds by a protease can be measured as the difference in absorbance between a protease treated sample and a control sample. The assay is conducted essentially according to Nielsen et al. (Nielsen et al., 2001, Improved method for determining food protein degree of hydrolysis, *J. Food Sci.* 66: 642-646).

500 μl of sample is filtered through a 100 kDa Microcon centrifugal filter (60 min, 11,000 rpm, 5° C.). The samples are diluted appropriately (e.g., 10, 50 or 100 times) in deionizer water and 25 μl of each sample is loaded into a 96 well microtiter plate (5 replicates). 200 μl OPA reagent (100 mM di-sodium tetraborate decahydrate, 3.5 mM sodium dodecyl sulphate (SDS), 5.7 mM di-thiothreitol (DDT), 6 mM o-phthaldialdehyde) is dispensed into all wells, the plate is shaken (10 sec, 750 rpm) and absorbance measured at 340 nm.

Strain

The strain *Meripilus giganteus* was isolated from a fruiting body collected in Denmark in 1993 by Novozymes.

An in-house *Trametes* cf. *versicolor* strain identified by ITS (Internal Transcribed Spacer) sequencing was used as the source of the protease gene SEQ ID NO: 15.

A second *Trametes vesicolor* strain sequenced by Genome Canada (fungalgenomics.ca) was used to identify the protease gene SEQ ID NO: 20.

*Escherichia coli* Top-10 strain purchased from Invitrogen (Life Technologies, Carlsbad, Calif., USA) was used to propagate the expression vectors.

*Aspergillus oryzae* MT3568 strain was used for heterologous expression of the gene encoding polypeptides having homology with polypeptides with protease activity. *A. oryzae* MT3568 is an amdS (acetamidase) disrupted gene derivative of *Aspergillus oryzae* JaL355 (WO 02/40694) in which pyrG auxotrophy was restored by disrupting the *A. oryzae* acetamidase (amdS) gene with the pyrG gene.

Example 1: Recombinant Expression of the S53 Protease 3 from *Meripilus giganteus* (SEQ ID NO: 3)

In order to obtain material for testing and characterization of the S53 Protease 3 from *Meripilus giganteus*, the DNA sequence from Seq ID NO: 1 was cloned in an *Aspergillus* expression vector and expressed in *Aspergillus oryzae.*

The S53 Protease 3 gene from *Meripilus giganteus* was sub-cloned into the *Aspergillus* expression vector pMStr100 (WO 2010/009400) by amplifying the coding region without the stop codon of the DNA in Seq ID NO: 1 from the cDNA plasmid clone, pA2PR22, with standard PCR techniques using the following primers:

```
597
                                   (SEQ ID NO: 13)
TAGGGATCCTCACGATGGTCGCCACCAGCT

598
                                   (SEQ ID NO: 14)
CAGGCCGACCGCGGTGAG
```

The PCR product was restricted with BamHI and ligated into the BamHI and NruI sites of pMStr100, resulting in an in-frame fusion with the C-terminal tag sequence RHQHQHQH (stop) in the expression vector. The S53 Protease 3 gene in the resulting *Aspergillus* expression construct, pMStr121, was sequenced, and the protease coding portion of the sequence was confirmed to agree with the original coding sequence of SEQ ID NO: 1. The in-frame fusion to the tag encoding sequence was also confirmed, resulting in the sequence in SEQ ID NO: 3, which encodes the peptide sequence in SEQ ID NO: 4.

The *Aspergillus oryzae* strain BECh2 (WO 00/39322) was transformed with pMStr121 using standard techniques as described by Christensen et al., 1988, *Biotechnology* 6: 1419-1422 and WO 2004/032648. To identify transformants producing the recombinant protease, the transformants and BECh2 were cultured in 10 ml of YP+2% glucose medium at 30° C. and 200 rpm. Samples were taken after 3 days growth and resolved with SDS-PAGE to identify recombinant protease production. A novel band between 35 and 50 kDa was observed in cultures of transformants that was not observed in cultures of the untransformed BECh2. Several transformants that appeared to express the recombinant protease at high levels were further cultured in 100 ml of YP+2% glucose medium in 500 ml shake flasks at 30° C. and 200 rpm. Samples were taken after 2, 3, and 4 days growth and expression levels compared by resolving the samples with SDS-PAGE. A single transformant that expressed the recombinant protease at relatively high levels was selected and designated EXP01737. EXP01737 was isolated twice by dilution streaking conidia on selective medium containing 0.01% TRITON® X-100 to limit colony size and fermented in YP+2% glucose medium in shake flasks as described above to provide material for purification. The shake flask cultures were harvested after 4 days growth and fungal mycelia was removed by filtering the fermentation broth through Miracloth (Calbiochem) then purified as described in example 2.

YP+2% Glucose Medium

| |
|---|
| 10 g yeast extract |
| 20 g peptone |
| water to 1 L |
| autoclave at 121° C., 20 minutes |
| add 100 ml 20% sterile glucose solution |

Example 2: Purification of the S53 Protease 3 from *Meripilus giganteus* with C-Terminal HQ-Tag The culture broth was centrifuged (20000×g, 20 min) and the supernatant was carefully decanted from the precipitate. The supernatant was filtered through a Nalgene 0.2 μm filtration unit in order to remove the rest of the *Aspergillus* host cells. The 0.2 μm filtrate was transferred to 10 mM Succinic acid/NaOH, pH 3.5 on a G25 Sephadex column (from GE Healthcare). The G25 sephadex transferred enzyme was applied to a Q-sepharose FF column (from GE Healthcare) equilibrated in 10 mM Succinic acid/NaOH, pH 3.5. The run-through and wash with 10 mM Succinic acid/NaOH, pH 3.5 was collected and contained the S53 protease (activity confirmed using the Kinetic Suc-AAPF-pNA assay at pH 4). The pH of the run-through and wash fraction was adjusted to pH 3.25 with 1 M HCl while mixing the fraction thoroughly. The pH-adjusted solution was applied to a SP-sepharose FF column (from GE Healthcare) equilibrated in 10 mM Succinic acid/NaOH, pH 3.25. After washing the column extensively with the equilibration buffer, the protease was eluted with a linear NaCl gradient (0→0.5 M) in the same buffer over ten column volumes. Fractions from the column were analysed for protease activity (using the Kinetic Suc-AAPF-pNA assay at pH 4) and peak-fractions were pooled. Solid ammonium sulphate was added to the pool to 2.0 M final $(NH_4)_2SO_4$ concentration. The enzyme solution was applied to a Phenyl-Toyopearl column (from TosoHaas) equilibrated in 10 mM Succinic acid/NaOH, 2.0 M $(NH_4)_2SO_4$, pH 3.25. After washing the column extensively with the equilibration buffer, the S53 protease was eluted with a linear gradient between the equilibration buffer and 10 mM Succinic acid/NaOH, pH 3.25 over ten column volumes. Fractions from the column were analyzed for protease activity (using the Kinetic Suc-AAPF-pNA assay at pH 4). Fractions with high activity were pooled and transferred to 10 mM Succinic acid/NaOH, pH 3.5 on a G25 sephadex column (from GE Healthcare). The G25 sephadex transferred protease was applied to a SP-sepharose HP column (from GE Healthcare) equilibrated in 10 mM Succinic acid/NaOH, pH 3.5. After washing the column extensively with the equilibration buffer, the protease was eluted with a linear NaCl gradient (0→0.5 M) in the same buffer over five column volumes. Fractions constituting the major peak from the column were pooled as the purified product. The purified product was analysed by SDS-PAGE and one major band was seen on the gel and three minor bands. EDMAN N-terminal sequencing of the bands showed that all the bands were related to the S53 protease and therefore we expect that the minor bands represents nicking of some of the S53 protease molecules. The purified product was used for further characterization.

Example 3: Characterization of the S53 Protease 3 from *Meripilus giganteus* with C-Terminal HQ-Tag The Kinetic Suc-AAPF-pNA assay was used for obtaining the pH-activity profile and the pH-stability profile (residual activity after 2 hours at indicated pH-values). For the pH-stability profile the protease was diluted 10× in the different assay buffers to reach the pH-values of these buffers and then incubated for 2 hours at 37° C. After incubation, the pH of the protease incubations was transferred to the same pH-value, before assay for residual activity, by dilution in the pH 4.0 Assay buffer. The Endpoint Suc-AAPF-pNA assay was used for obtaining the temperature-activity profile at pH 4.0. The Kinetic Suc-AAPX-pNA assay and ten different Suc-AAPX-pNA substrates were used for obtaining the P1-specificity of the enzyme at pH 4.0.

The results are shown in tables 2-5 below. Data for Protease 10R are included in the tables. For table 2, the activities are relative to the optimal pH for the enzymes. For table 3, the activities are residual activities relative to samples, which were kept at stable conditions (5° C., pH 4.0 for the S53 protease 3 from *Meripilus giganteus* (from example 2); 5° C., pH 9.0 for Protease 10R). For table 4, the activities are relative to the optimal temperature for the enzyme (pH 4.0 for the S53 protease 3 from *Meripilus*

*giganteus* (from example 2); pH 6.5 for Protease 10R). For table 5, the activities are relative to the best substrate for the enzymes (Suc-AAPL-pNA for the S53 protease 3 from *Meripilus giganteus* (from example 2)). The Protazyme AK assay was used for obtaining the temperature-activity profile at pH 6.5 for Protease 10R.

The pH-activity on the Suc-AAPF-pNA substrate, the pH-stability profile (residual activity after 2 hours at 37° C.), the temperature activity profile on Suc-AAPF-pNA at pH 4.0 and the P1-specificity on 10 Suc-AAPF-pNA substrates at pH 4.0 for the S53 protease 3 from *Meripilus giganteus* (from example 2) compared with the data for Protease 10R are also shown in FIGS. 1-4. For Protease 10R, the temperature activity profile is on Protazyme AK at pH 6.5 and the P1-specificity is at pH 9.0.

TABLE 2 pH-activity profile at 25° C. as determined using the kinetic Suc-AAPF-pNA assay

| pH | S53 protease 3 from *Meripilus giganteus* (from example 2) | Protease 10R |
|---|---|---|
| 2 | 0.38 | — |
| 3 | 0.95 | 0.00 |
| 4 | 1.00 | 0.02 |
| 5 | 0.27 | 0.07 |
| 6 | 0.02 | 0.21 |
| 7 | 0.00 | 0.44 |
| 8 | 0.00 | 0.67 |
| 9 | 0.00 | 0.88 |
| 10 | 0.00 | 1.00 |
| 11 | 0.00 | 0.93 |

TABLE 3 pH-stability profile (residual activity after 2 hours at 37° C.) as determined using the kinetic Suc-AAPF-pNA assay

| pH | S53 protease 3 from *Meripilus giganteus* (from example 2) | Protease 10R |
|---|---|---|
| 2 | 0.01 | 0.78 |
| 3 | 0.99 | 1.03 |
| 4 | 0.96 | 0.99 |
| 5 | 0.94 | 1.00 |
| 6 | 0.87 | 1.03 |
| 7 | 0.69 | 1.01 |
| 8 | 0.01 | 0.98 |
| 9 | 0.01 | 0.99 |
| 10 | 0.01 | 0.99 |
| 11 | 0.01 | 0.86 |
| After 2 hours at 5° C. | 1.00 (at pH 4) | 1.00 (at pH 9) |

TABLE 4

Temperature activity profile at pH 4.0 or pH 6.5 as determined using the endpoint Suc-AAPF-pNA assay

| Temp (° C.) | S53 protease 3 from *Meripilus giganteus* (from example 2, pH 4) | Protease 10R (pH 6.5) |
|---|---|---|
| 15 | 0.07 | 0.01 |
| 25 | 0.23 | 0.02 |
| 37 | 0.58 | 0.06 |
| 50 | 1.00 | 0.13 |
| 60 | 0.44 | 0.35 |
| 70 | 0.08 | 0.96 |
| 80 | — | 1.00 |
| 90 | — | 0.18 |

TABLE 5

P1-specificity on 10 Suc-AAPX-pNA substrates at pH 4.0 or pH 9.0 at 37° C. as determined using the kinetic Suc-AAPX-pNA assay

| Suc-AAPX-pNA | S53 protease 3 from *Meripilus giganteus* (from example 2, pH 4) | Protease 10R (pH 9) |
|---|---|---|
| Suc-AAPA-pNA | 0.01 | 0.13 |
| Suc-AAPR-pNA | 0.00 | 0.09 |
| Suc-AAPD-pNA | 0.06 | 0.00 |
| Suc-AAPI-pNA | 0.00 | 0.00 |
| Suc-AAPM-pNA | 0.53 | 0.78 |
| Suc-AAPV-pNA | 0.00 | 0.01 |
| Suc-AAPL-pNA | 1.00 | 0.18 |
| Suc-AAPE-pNA | 0.05 | 0.00 |
| Suc-AAPK-pNA | 0.00 | 0.08 |
| Suc-AAPF-pNA | 0.99 | 1.00 |

Other Characteristics for the S53 Protease 3 from *Meripilus giganteus* (from Example 2)

Determination of the N-terminal sequence was: AIPASCASTI.

The relative molecular weight as determined by SDS-PAGE was approx. $M_r$ =43 kDa.

Confirmation of C-Terminal HQ-Tag Attached to Mature Sequence

This sample was buffer exchanged with 50 mM sodium acetate buffer pH 5.5 using a Vivaspin ultrafiltration unit fitted with a 10 kDa cut off filter. Following buffer exchange, 2 μL of endoglycosidase H was added and the sample was then incubated at 5° C. overnight. Note: For every deglycosylated N-linked site one N-acetyl hexosamine residue remains on the protein backbone increasing the molecular weight with 203.19 Da per site. The sample was then analyzed by mass-spectrometry.

The molecular weight determined by intact molecular weight analysis of the major peak was: 38088.6 Da, corresponding to within 1.8 Da of the mature sequence plus-RHQHQ plus a single acetyl hexosamine and one non-crosslinked cysteine residue.

The molecular weight determined by intact molecular weight analysis of the secondary peak was: 37961 Da, corresponding to within 2.3 Da of the mature sequence plus-RHQH plus a single acetyl hexosamine and one non-crosslinked cysteine residue.

The mature sequence (from EDMAN N-terminal sequencing data and intact molecular weight analysis):

```
                                              (SEQ ID NO: 6)
AIPASCASTITPACLQAIYGIPTTKATQSSNKLAVSGFIDQFANKADLKS

FLAQFRKDISSSTTFSLQTLDGGENDQSPSEAGIEANLDIQYTVGLATGV

PTTFISVGDDFQDGNLEGFLDIINFLLGESNPPQVLTTSYGQNENTISAK

LANQLCNAYAQLGARGTSILFASGDGGVSGSQSAHCSNFVPTFPSGCPFM
```

-continued

```
TSVGATQGVSPETAAAFSSGGFSNVFGIPSYQASAVSGYLSALGSTNSGK

FNRSGRGFPDVSTQGVDFQIVSGGQTIGVDGTSCASPTFASVISLVNDRL

IAAGKSPLGFLNPFLYSSAGKAALNDVTSGSNPGCSTNGFPAKAGWDPVT

GLGTPNFAKLLTAVGLRHQHQ.
```

The calculated molecular weight from this mature sequence is 37882.6 Da.

Example 4: Soybean-Maize Meal Activity Assay

An end-point assay using soybean-maize meal as substrate was used for obtaining the activity profile of the proteases at pH 3-7.

Substrate: Soybean meal-maize meal mixed in a 30:70 ratio.

Assay buffers: 9 buffers containing 100 mM succinic acid, 100 mM HEPES, 100 mM CHES, 100 mM CAPS, 1 mM $CaCl_2$, 150 mM KCl, 0.01% Triton X-100 were prepared and adjusted using HCl or NaOH to a pH value such that after soybean-maize meal substrate (1 g) had been mixed with assay buffer (10 mL) to give a slurry, the final pH of the slurry was one of the following pH's: 3.0, 4.0, 5.0, 6.0, 7.0, 8.0, 9.0, 10.0 and 11.0.

Substrate slurry (2 mL) was mixed for 30 min before protease addition and incubated for 3 hours at 40° C. (500 rpm). Protease (200 mg enzyme protein/kg dry matter) was dissolved in 100 μl 100 mM sodium acetate buffer (9.565 g/L NaOAc, 1.75 g/L acetic acid, 5 mM $CaCl_2$, 0.01% BSA, 0.01% Tween20, pH 6.0) and added. Samples were centrifuged (10 min, 4000 rpm, 0° C.) and the supernatants collected for analysis using the o-Phthaldialdehyde (OPA) assay.

The results are shown in Table 6 below. The proteolytic activity of the S53 protease 3 from *Meripilus giganteus* (from example 2) on soybean-maize meal is at its highest at pH 3 and decreases with increasing pH. At pH 5, the S53 protease 3 from *Meripilus giganteus* (from example 2) is as active on soybean-maize meal as Protease 10R, whereas at pH 3 and pH 4 the S53 protease 3 from *Meripilus giganteus* (from example 2) is much more active than Protease 10R. These results indicate that the S53 protease 3 from *Meripilus giganteus* (from example 2) could be efficient for obtaining protein hydrolysis in the upper gastro-intestinal tract of monogastric animals such as, e.g., pigs and poultry leading to improved utilization of feed protein in these species.

TABLE 6

Protease activity (OD340 × dilution factor) on soybean-maize meal at pH 3.0, 4.0, 5.0, 6.0 and 7.0

| | S53 protease 3 from *Meripilus giganteus* (from example 2) | | Protease 10R | |
|---|---|---|---|---|
| pH | Average | Standard deviation | Average | Standard deviation |
| 3.0 | 3.02 | 0.08 | 0.22 | 0.06 |
| 4.0 | 1.31 | 0.06 | 0.30 | 0.10 |
| 5.0 | 0.64 | 0.03 | 0.71 | 0.01 |
| 6.0 | 0.19 | 0.04 | 1.81 | 0.14 |
| 7.0 | 0.02 | 0.04 | 2.92 | 0.11 |

Figure 1:
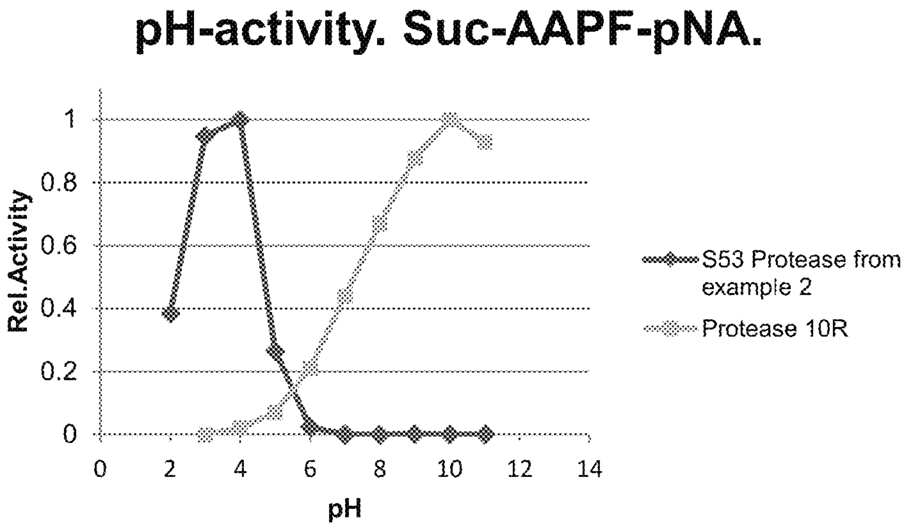
FIG. 1 shows the pH-activity profile of the S53 protease 3 from *Meripilus giganteus* (SEQ ID NO: 3) (from example 2) compared to protease 10R on the Suc-AAPF-pNA substrate at 25° C.
Figure 2:
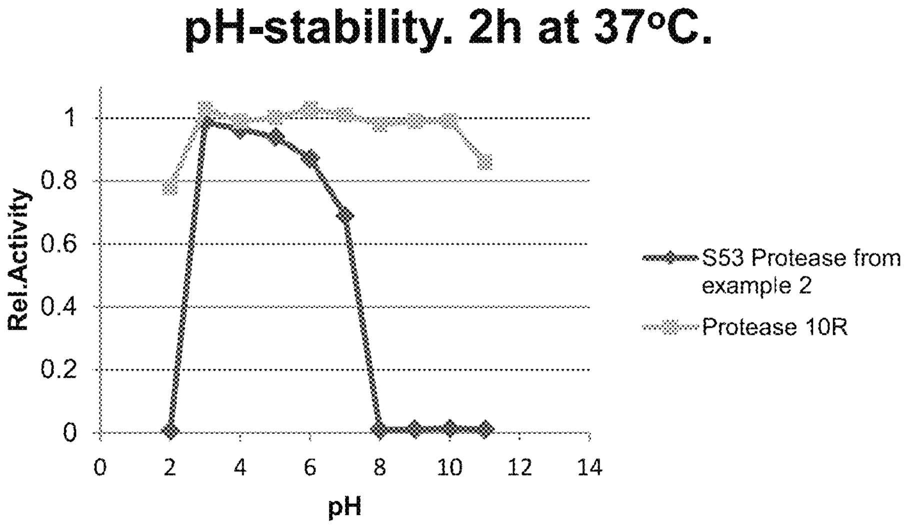
FIG. 2 shows the pH-stability profile of the S53 protease 3 from *Meripilus giganteus* (SEQ ID NO: 3) (from example 2) compared to protease 10R (residual activity after 2 hours at 37° C.).
Figure 3:
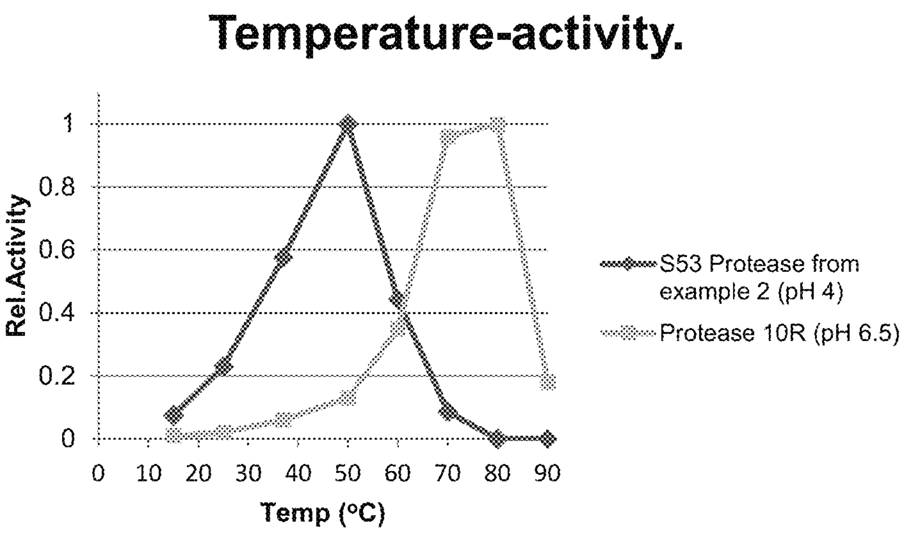
FIG. 3 shows the temperature activity profile of the S53 protease 3 from *Meripilus giganteus* (SEQ ID NO: 3) (from example 2) at pH 4.0 compared to protease 10R on Protazyme AK at pH 6.5.
Figure 4:
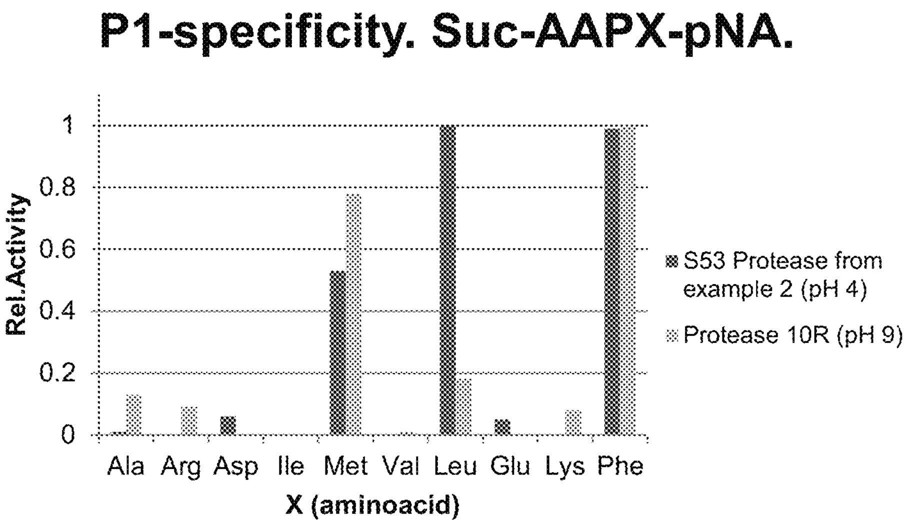
FIG. 4 shows the P1-specificity of the S53 protease 3 from *Meripilus giganteus* (SEQ ID NO: 3) (from example 2) at pH 4 compared to protease 10R at pH 9.0 on 10 Suc-AAPX-pNA substrates, 25° C.
Figure 5:
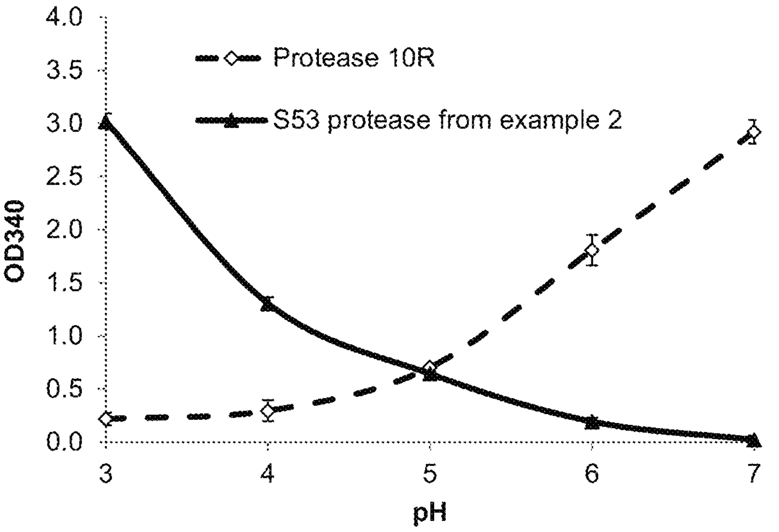
FIG. 5 shows the activity ($OD_{340}$× dilution factor) on soybean-maize meal of the S53 protease 3 from *Meripilus giganteus* (SEQ ID NO: 3) (from example 2) compared to protease 10R.

FIG. 5 shows the activity ($OD_{340}$× dilution factor) on soybean-maize meal of the S53 protease 3 from *Meripilus giganteus* (from example 2) compared to the 10R protease.

Example 5: Proteolytic Activity on Crop, Gizzard and Ileum Digesta from Broiler Chickens Crop, gizzard and ileum digesta material from 21 day old broiler chickens fed a corn-soy diet was collected; freeze dried and ground using a small coffee mill. The ground samples were suspended (47% w/v) in the following buffers and left to hydrate at 4° C. overnight (no stirring):

Crop buffer: 100 mM HEPES, 1 mM $CaCl_2.2H_2O$, 150 mM KCl, 0.01% Triton X-100, adjusted to pH 5 using HCl Gizzard buffer: 100 mM succinic acid, 1 mM $CaCl_2.2H_2O$, 150 mM KCl, 0.01% Triton X-100, adjusted to pH 1.67 using HCl Ileum buffer: 100 mM HEPES, 1 mM $CaCl_2.2H_2O$, 150 mM KCl, 0.01% Triton X-100, adjusted to pH 7.2 using HCl The resulting pH was: pH 5 in crop samples; pH 3 in gizzard samples; and pH 7 in ileum samples. The suspensions were heated to 40° C. and 1 ml was dispensed into tubes kept at 40° C. Three tubes representing blank ($T_0$) were immediately centrifuged (3000×g, 0° C., 10 min) and the supernatants frozen. Either enzyme (200 mg enzyme protein/kg substrate) in 50 μL 100 mM sodium acetate buffer (9.565 g/l NaOAc, 1.75 g/l acetic acid, 5 mM $CaCl_2$, 0.01% BSA, 0.01% Tween20, pH 6.0) or just sodium acetate buffer (50 μL) for the blank samples was added to the tubes and crop and ileum samples were incubated for 3 hours ($T_3$) while the gizzard samples were incubated for 1 hour ($T_1$) at 40° C. while shaking (500 rpm). The samples were centrifuged (3000×g, 0° C., 10 min) and supernatants recovered and frozen. The proteolytic activity was determined by analyzing primary amines using the o-phthaldialdehyde (OPA) assay.

The results are shown in Table 7. For each of the digesta types (crop, gizzard and ileum) there was a significant difference between the level of primary amines in the blank $T_0$ sample and the blank samples incubated for 1 or 3 hours. This difference can be ascribed to activity of proteases present in the substrate and originating from either the diet raw materials or the animal. During incubation of the crop and gizzard digesta the S53 protease 3 from *Meripilus giganteus* (from example 2) further increased the level of primary amines compared to the blank sample, demonstrating that the protease had a proteolytic activity on this substrate under the given conditions. The S53 protease 3 from *Meripilus giganteus* (from example 2) performed significantly better during crop and gizzard incubation than Protease 10R, indicating that the S53 protease 3 from *Meripilus giganteus* (from example 2) could be more efficient for feed protein hydrolysis in the upper gastro-intestinal tract of poultry leading to improved protein digestibility. As expected the S53 protease 3 from *Meripilus giganteus* (from example 2) did not significantly increase the level of free amines during ileum incubation at pH 7.

TABLE 7

Proteolytic activity of the S53 protease 3 from *Meripilus giganteus* (from example 2) compared to Protease 10R when incubated with broiler digesta and expressed as level of primary amines measured by the OPA assay ($OD_{340}$ × dilution factor)

| Treatment | Crop (3 hours) | Gizzard (1 hour) | Ileum (3 hours) |
|---|---|---|---|
| Blank ($T_0$) | 2.21 ± $0.02^d$ | 2.95 ± $0.02^c$ | 9.37 ± $0.08^c$ |
| Blank | 3.54 ± $0.02^c$ | 3.94 ± $0.08^b$ | 14.40 ± $0.66^{ab}$ |

TABLE 7-continued

Proteolytic activity of the S53 protease 3 from *Meripilus giganteus* (from example 2) compared to Protease 10R when incubated with broiler digesta and expressed as level of primary amines measured by the OPA assay ($OD_{340}$ × dilution factor)

| Treatment | Crop (3 hours) | Gizzard (1 hour) | Ileum (3 hours) |
|---|---|---|---|
| S53 protease 3 from *Meripilus giganteus* (from example 2) | 4.13 ± $0.03^{a}$ | 4.37 ± $0.05^{a}$ | 14.20 ± $0.19^{ab}$ |
| Protease 10R | 3.85 ± $0.07^{b}$ | 3.87 ± $0.21^{b}$ | 14.74 ± $0.15^{a}$ |

[a,b,c]Values within a column that are not connected by the same superscript letters are statistically different as determined by the Tukey Kramer test (α = 0.05) provided by the ANOVA procedure (SAS Institute Inc.).

Figure 6:
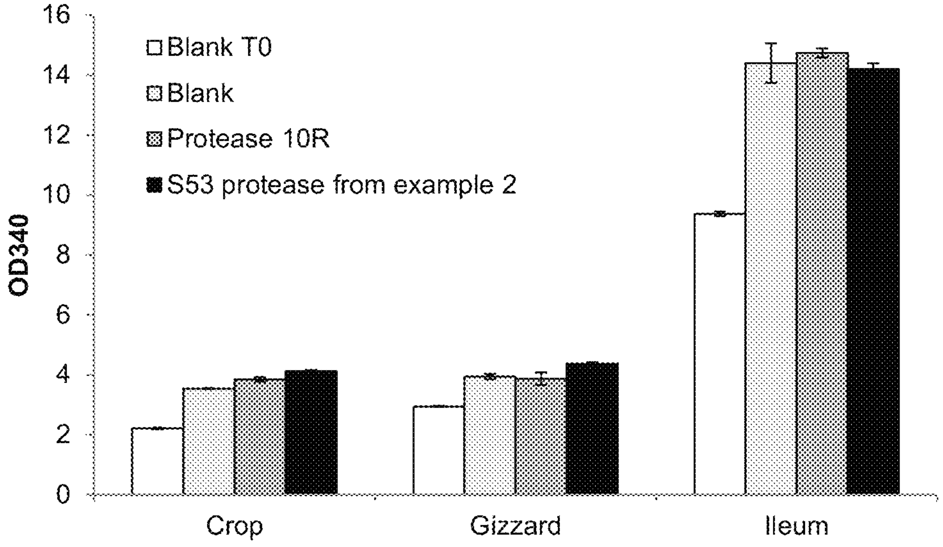
FIG. 6 shows the level of free amines ($OD_{340}$× dilution factor) in Blank To samples, Blank samples and samples incubated with the S53 protease 3 from *Meripilus giganteus* (SEQ ID NO: 3) (from example 2) or protease 10R.
Figure 7:
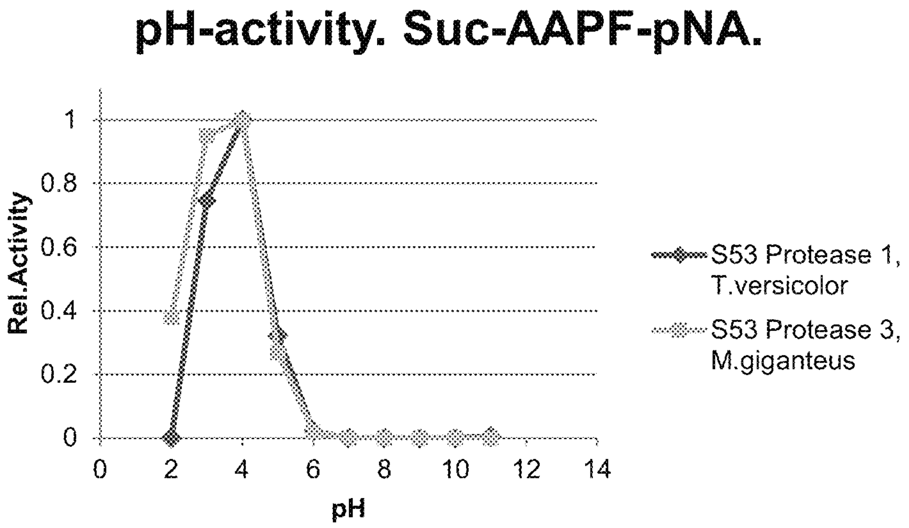
FIG. 7 shows the pH-activity profile of the S53 protease 1 isolated from *Trametes* cf. *versicolor* (SEQ ID NO: 16) compared to the S53 protease 3 from *Meripilus giganteus* (SEQ ID NO: 3) (from example 2) on the Suc-AAPF-pNA substrate at 25° C.
Figure 8:
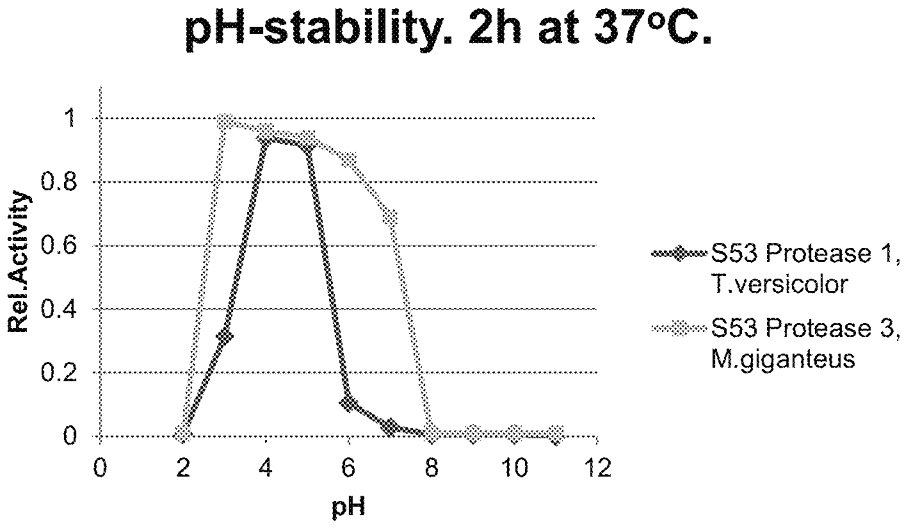
FIG. 8 shows the pH-stability profile of the S53 protease 1 isolated from *Trametes* cf. *versicolor* (SEQ ID NO: 16)

FIG. 6 shows the level of free amines ($OD_{340}$× dilution factor) in blank $T_0$ samples, blank samples and samples incubated with the S53 protease 3 from *Meripilus giganteus* (from example 2) or the 10R protease. The substrate for the incubation was digesta material from the crop, gizzard or ileum of broiler chickens.

Example 6: Thermostability

An aliquot of the protein sample of protease (purified as described in Example 2 or 12) is either desalted or buffer-changed into 20 mM Na-acetate, pH 4.0 using a prepacked PD-10 column or dialysed against 2×500 ml 20 mM Na-acetate, pH 4.0 at 4° C. in a 2-3 h step followed by an overnight step. The sample is 0.45 μm filtered and diluted with buffer to approx. 2 A280 units. The dialysis buffer is used as reference in Differential Scanning calorimetry (DSC). The samples are degassed using vacuum suction and stirring for approx. 10 minutes.

A DSC scan is performed on a MicroCal VP-DSC at a constant scan rate of 1.5° C./min from 20-90° C. Data-handling is performed using the MicroCal Origin software (version 4.10), and the denaturation temperature, $T_d$ (also called the melting temperature, $T_m$) is defined as the temperature at the apex of the peak in the thermogram.

Example 7: Steam Stability

Residual activity of the protease after steam treatment may be evaluated using the following assay.

In these experiments, a modified set-up is used whereby the steam is provided from a steam generator and led into the box. The samples placed on a plate are inserted into the box through a drawer when the temperature has reached ca. 93-94° C. Upon the insertion of the samples the temperature drops 4° C. Incubation is performed for 30 seconds while the temperature remains approximately constant at 90° C. Thereafter the plate is quickly removed from the box, the samples placed on ice, re-suspended and evaluated with respect to protease activity using, e.g., the Suc-AAPF-pNA or o-Phthaldialdehyde (OPA) assay. Each enzyme sample is compared to a similar sample that had not been steam treated in order to calculate residual activity.

Example 8: Pelleting Stability Tests

The enzyme granulation is performed in a manner as described in U.S. Pat. No. 4,106,991, Example 1. The obtained granulate is dried in a fluid bed to a water content below 1% and sifted to obtain a product with the particle range 250 μm to 850 μm. Finally, the product is coated with palm oil and calcium carbonate in a manner as described in U.S. Pat. No. 4,106,991, Example 22.

Approximately 50 g enzyme granulate is pre-mixed with 10 kg feed for 10 minutes in a small horizontal mixer. This premix is mixed with 90 kg feed for 10 minutes in a larger horizontal mixer. From the mixer, the feed is led to the conditioner (a cascade mixer with steam injection) at a rate of approximately 300 kg/hour. The conditioner heats up the feed to 95° C. (measured at the outlet) by injecting steam. The residence time in the conditioner is 30 seconds. From the conditioner, the feed is led to a Simon Heesen press equipped with 3.0×35 mm horizontal die and pressed to pellets with a length of around 15 mm. After the press, the pellets are placed in an air cooler and cooled for 15 minutes.

The protease activity is measured using the Suc-AAPF-pNA assay prior to pelleting and in the feed pellets after pelleting. Pelleting stability is determined by comparing the protease activity in pelleted feed relative to the activity in non-pelleted feed.

Example 9: Cloning of Two Protease Genes from *Trametes* cf. *Versicolor* and *Trametes versicolor*

Based on the gene sequences identified, SEQ ID NO: 15 from a *Trametes* cf. *versicolor* strain (see strain section) and SEQ ID NO: 20 from a *Trametes versicolor* strain (see strain section) two synthetic coding DNA sequences (CDS) with codon optimization for *Aspergillus oryzae* expression were designed (SEQ ID NO: 17 and SEQ ID NO: 22, respectively). Those two CDS sequences were synthesized by GeneArt® (Life Technologies, Carlsbad, Calif., USA) in a pMA-T vector at a 5 μg scale with two flanking sites BamHI in 5' and HindIII in 3' compatible with the expression vector pDAu109 (WO 2005/042735). 1 μg of those plasmids was subsequently digested with the restriction enzymes BamHI and HindIII from NEB (New England Biolabs, Frankfurt am Main Germany) following manufacturer's recommendations, and the resulting fragments were separated by 1% agarose gel electrophoresis using TAE buffer. The 1.7 kb fragment corresponding to the synthetic protease genes were excised from the gel and purified using a GFX® PCR DNA and Gel Band Purification Kit (GE Healthcare, HiHerød, Denmark) following the manufacturer's instructions. 100 ng of those inserts were cloned in the expression vector pDAu109 (WO 2005/042735) previously digested with BamHI and HindIII by ligation with a T4 ligase from NEB (New England Biolabs, Frankfurt am Main Germany) following the manufacturer's instructions.

A 2.5 μl volume of the diluted ligation mixture was used to transform *E. coli* TOP10 chemically competent cells (Life Technologies, Carlsbad, Calif., USA). Three colonies were selected from LB agar plates containing 100 μg of ampicillin per ml for each construct and cultivated overnight in 3 ml of LB medium supplemented with 100 μg of ampicillin per ml. Plasmid DNA was purified using a Qiagen Spin Miniprep kit (Cat. 27106) (QIAGEN GmbH, Hilden, Germany) according to the manufacturer's instructions. The *Trametes* cf. *versicolor* and *Trametes* versicolorprotease synthetic sequences were verified by Sanger sequencing before heterologous expression. The plasmids designated as MDQM0673-1 and MDQM0584-1 (holding the CDS SEQ ID NO: 17 and SEQ ID NO: 22, respectively) were selected for protoplast transformation and heterologous expression of its encoded proteases in an *Aspergillus oryzae* host cell MT3568 (described in the strain chapter).

Example 10: Transformation of *Aspergillus oryzae* with the Gene Encoding Proteases from *Trametes* cf. *Versicolor* and *Trametes versicolor* and Selection of the Best Transformants Protoplasts of *Aspergillus oryzae* MT3568 (see strains chapter) were prepared according to WO 95/02043. One hundred μl of protoplasts were mixed with 2.5-10 μg of either of the *Aspergillus* expression vectors MDQM0673-1 and MDQM0584-1 (Example 9), 250 μl of 60% PEG 4000 (Applichem, Darmstadt, Germany) (polyethylene glycol, molecular weight 4,000), 10 mM $CaCl_2$, and 10 mM Tris-HCl pH 7.5 and gently mixed. The mixture was incubated at 37° C. for 30 minutes and the protoplasts were spread onto COVE plates for selection. After incubation for 4-7 days at 37° C. spores of eight transformants were inoculated into 0.5 ml of DAP4C-1 medium supplemented lactic acid and with diammonium phosphate in 96 deep well plates. After 4 days cultivation at 30° C., the culture broths were analyzed by SDS-PAGE using Novex® 4-20% Tris-Glycine Gel (Invitrogen Corporation, Carlsbad, Calif., USA) to identify the transformants producing the largest amount of recombinant protease from *Trametes versicolor.*

Based on the band intensity of the SDS-PAGE gel, spores of the best transformant were spread on COVE-Sucrose-T plates containing 0.01% TRITON® X-100 in order to isolate single colonies. The spreading was repeated twice in total on COVE-Sucrose-T plates, and then a single colony was spread on a COVE-N-Agar tube until sporulation.

Example 11: Fermentation of *Aspergillus oryzae* Transformed with the Gene Encoding Proteases from *Trametes* cf. *Versicolor* and *Trametes versicolor*

150 ml of DAP4C-1 medium supplemented with 5 ml of 20% lactic acid and 3.5 ml of 50% diammonium phosphate and spores from the best transformants were cultivated in shake flasks during 4 days at a temperature of 30° C. under 100 rpm agitation. Culture broths were harvested by filtration using a 0.2 μm filter device and used for further characterization.

Example 12: Purification of the S53 Protease 1 from *Trametes* cf *Versicolor*

The culture broth was centrifuged (20000×g, 20 min) and the supernatant was carefully decanted from the precipitate. The supernatant was filtered through a Nalgene 0.2 μm filtration unit in order to remove the rest of the *Aspergillus* host cells. The 0.2 μm filtrate was transferred to 10 mM Succinic acid/NaOH, pH 3.5 on a G25 Sephadex column (from GE Healthcare). The G25 sephadex transferred enzyme was applied to a SP-sepharose FF column (from GE Healthcare) equilibrated in 10 mM Succinic acid/NaOH, pH 3.5. After washing the column extensively with the equilibration buffer, the protease was eluted with a linear NaCl gradient (0→1.0 M) in the same buffer over ten column volumes. Fractions from the column were analysed for protease activity (using the Kinetic Suc-AAPF-pNA assay at pH 4) and peak-fractions were analysed by SDS-PAGE. Fractions with one band only on the coomassie stained SDS-PAGE gel were pooled as the purified product. The purified product was used for further characterization.

Example 13: Characterization of the S53 Protease 1 from *Trametes* cf *Versicolor* (SEQ ID NO: 19)

The Kinetic Suc-AAPF-pNA assay was used for obtaining the pH-activity profile. The Endpoint Suc-AAPF-pNA assay was used for obtaining the pH-stability profile (residual activity after 2 hours at indicated pH-values) and the temperature-activity profile at pH 4.0. For the pH-stability profile the protease was diluted 7× in the different Assay buffers to reach the pH-values of these buffers and then incubated for 2 hours at 37° C. After incubation, the pH of the protease incubations was transferred to the same pH-value, before assay for residual activity, by dilution in the pH 4.0 Assay buffer. The Kinetic Suc-AAPX-pNA assay and ten different Suc-AAPX-pNA substrates were used for obtaining the P1-specificity of the enzyme at pH 4.0.

The results are shown in Tables 8-11 below. Data for S53 protease 3 from *Meripilus giganteus* (from example 2) and protease 10R are included in the tables. For Table 8, the activities are relative to the optimal pH for the enzymes. For Table 9, the activities are residual activities relative to samples, which were kept at stable conditions (5° C., pH 4.0). For Table 10, the activities are relative to the optimal temperature at pH 4.0 for the enzyme. For Table 11, the activities are relative to the best substrate for the enzymes (Suc-AAPL-pNA for the S53 protease 1 from *Trametes* cf *versicolor*).

TABLE 8 pH-activity profile at 25° C. as determined using the kinetic Suc-AAPF-pNA assay

| pH | S53 protease 1 from *Trametes* cf *versicolor* (from example 12) | S53 protease 3 from *Meripilus giganteus* (from example 2) | Protease 10R |
|---|---|---|---|
| 2 | 0.00 | 0.38 | — |
| 3 | 0.75 | 0.95 | 0.00 |
| 4 | 1.00 | 1.00 | 0.02 |
| 5 | 0.32 | 0.27 | 0.07 |
| 6 | 0.02 | 0.02 | 0.21 |
| 7 | 0.00 | 0.00 | 0.44 |
| 8 | 0.00 | 0.00 | 0.67 |
| 9 | 0.00 | 0.00 | 0.88 |
| 10 | 0.00 | 0.00 | 1.00 |
| 11 | 0.00 | 0.00 | 0.93 |

TABLE 9 pH-stability profile (residual activity after 2 hours at 37° C.) as determined using the kinetic Suc-AAPF-pNA assay

| pH | S53 protease 1 from *Trametes* cf *versicolor* (from example 12) | S53 protease 3 from *Meripilus giganteus* (from example 2) | Protease 10R |
|---|---|---|---|
| 2 | 0.01 | 0.01 | 0.78 |
| 3 | 0.31 | 0.99 | 1.03 |
| 4 | 0.94 | 0.96 | 0.99 |
| 5 | 0.92 | 0.94 | 1.00 |
| 6 | 0.10 | 0.87 | 1.03 |
| 7 | 0.03 | 0.69 | 1.01 |
| 8 | 0.01 | 0.01 | 0.98 |
| 9 | 0.01 | 0.01 | 0.99 |
| 10 | 0.01 | 0.01 | 0.99 |
| 11 | 0.00 | 0.01 | 0.86 |
| After 2 hours at 5° C. | 1.00 (at pH 4) | 1.00 (at pH 4) | 1.00 (at pH 9) |

TABLE 10

Temperature activity profile at pH 4.0 or pH 6.5 as determined using the endpoint Suc-AAPF-pNA assay

| Temp (° C.) | S53 protease 1 from *Trametes* cf *versicolor* (from example 12, pH 4) | S53 protease 3 from *Meripilus giganteus* (from example 2, pH 4) | Protease 10R (pH 6.5) |
|---|---|---|---|
| 15 | 0.16 | 0.07 | 0.01 |
| 25 | 0.36 | 0.23 | 0.02 |

TABLE 10-continued

| Temperature activity profile at pH 4.0 or pH 6.5 as determined using the endpoint Suc-AAPF-pNA assay | | | |
|---|---|---|---|
| Temp (° C.) | S53 protease 1 from *Trametes* cf *versicolor* (from example 12, pH 4) | S53 protease 3 from *Meripilus giganteus* (from example 2, pH 4) | Protease 10R (pH 6.5) |
| 37 | 1.00 | 0.58 | 0.06 |
| 50 | 0.79 | 1.00 | 0.13 |
| 60 | 0.16 | 0.44 | 0.35 |
| 70 | 0.08 | 0.08 | 0.96 |
| 80 | — | — | 1.00 |
| 90 | — | — | 0.18 |

TABLE 11

| P1-specificity on 10 Suc-AAPX-pNA substrates at pH 4.0 or pH 9.0 at 37° C. as determined using the kinetic Suc-AAPX-pNA assay | | | |
|---|---|---|---|
| Suc-AAPX-pNA | S53 protease 1 from *Trametes* cf *versicolor* (from example 12, pH 4) | S53 protease 3 from *Meripilus giganteus* (from example 2, pH 4) | Protease 10R (pH 9) |
| Suc-AAPA-pNA | 0.01 | 0.01 | 0.13 |
| Suc-AAPR-pNA | 0.00 | 0.00 | 0.09 |
| Suc-AAPD-pNA | 0.04 | 0.06 | 0.00 |
| Suc-AAPI-pNA | 0.00 | 0.00 | 0.00 |
| Suc-AAPM-pNA | 0.46 | 0.53 | 0.78 |
| Suc-AAPV-pNA | 0.00 | 0.00 | 0.01 |
| Suc-AAPL-pNA | 1.00 | 1.00 | 0.18 |
| Suc-AAPE-pNA | 0.03 | 0.05 | 0.00 |
| Suc-AAPK-pNA | 0.00 | 0.00 | 0.08 |
| Suc-AAPF-pNA | 0.81 | 0.99 | 1.00 |

The pH-activity on the Suc-AAPF-pNA substrate, the pH-stability profile (residual activity after 2 hours at 37° C.), the temperature activity profile on Suc-AAPF-pNA at pH 4.0 and the P1-specificity on 10 Suc-AAPF-pNA substrates at pH 4.0 for the S53 protease 1 from *Trametes* cf *versicolor* compared with the data for the S53 protease 3 from *Meripilus giganteus* are also shown as FIGS. 1-4 below.

Other Characteristics for the S53 Protease 1 from *Trametes* cf *Versicolor*

Determination of the N-terminal sequence was: AIPASCASTI.

The relative molecular weight as determined by SDS-PAGE was approx. $M_r$ =42 kDa.

Confirmation of the Mature Sequence for the S53 Protease 1 from *Trametes* cf *Versicolor*

The purified sample was buffer exchanged with 50 mM sodium acetate buffer pH 5.5 using a Vivaspin ultrafiltration unit fitted with a 10 kDa cut off filter. Following buffer exchange, Endoglycosidase H was added and the sample was incubated at 30° C. for 3 hours. Note: For each deglycosylated N-linked site one N-acetyl hexosamine residue remains on the protein backbone increasing the molecular weight with 203.19 Da per site. The sample was then analyzed by mass-spectrometry.

The molecular weight determined by intact molecular weight analysis of the major peak was: 37467.6 Da, corresponding to within 0.41 Da of the mature sequence plus a single acetyl hexosamine and one non-crosslinked cysteine residue.

The mature sequence (from EDMAN N-terminal sequencing data and Intact MS data):

```
                                              (SEQ ID NO: 19)
AVPASCASTITPACLQALYGIPTTKATQSSNKLAVSGFIDQFANSADLKT

FLGKFRTDISSSTTFTLQTLDGGSNSQSSSQAGVEANLDIQYTVGLASAV

PTIFISVGDDFQDGDLEGFLDIINFLLNESAPPQVLTTSYGQNENTISAK

LANQLCNAYAQLGARGTSILFASGDGGVSGSQSSSCSKFVPTFPSGCPFM

TSVGATQGINPETAADFSSGGFSNVFARPSYQSTAVSSYLTALGSTNSGK

FNTSGRAFPDIATQGVDFEIVVSGRTEGVDGTSCASPTLAAIISLLNDRL

IAAGKSPLGFLNPFLYSAAGTAALTDITSGSNPGCNTNGFPAKAGWDPVT

GLGTPNFAKLLTAVGL.
```

The calculated molecular weight from this mature sequence is 37263.0 Da.

What is claimed is:

1. A variant of the polypeptide of SEQ ID NO: 5, said variant comprising a substitution, deletion, and/or insertion at one or more positions, wherein the variant has protease activity and is at least 90% identical to the polypeptide of SEQ ID NO: 5.

2. The variant of claim 1, which is at least 95% identical to the polypeptide of SEQ ID NO: 5.

3. The variant of claim 1, which is at least 97% identical to the polypeptide of SEQ ID NO: 5.

4. The variant of claim 1, which is at least 98% identical to the polypeptide of SEQ ID NO: 5.

5. The variant of claim 1, which is at least 99% identical to the polypeptide of SEQ ID NO: 5.

* * * * *